United States Patent [19]

Stein et al.

[11] Patent Number: 5,036,051
[45] Date of Patent: Jul. 30, 1991

[54] GLAUCOMA TREATMENT

[75] Inventors: Herman H. Stein, Highland Park; Jacob J. Plattner, Libertyville, both of Ill.

[73] Assignee: Abbott Laboratories, Abbott Park, Ill.

[21] Appl. No.: 488,810

[22] Filed: Mar. 2, 1990

Related U.S. Application Data

[60] Division of Ser. No. 240,567, Sep. 8, 1988, Pat. No. 4,927,807, Continuation-in-part of Ser. No. 105,636, Oct. 6, 1987, abandoned.

[51] Int. Cl.$^5$ .................. A61K 37/00; A61K 31/535; A61K 31/415; A61K 31/24
[52] U.S. Cl. .................... 514/18; 514/236.2; 514/400; 514/538; 514/540; 514/542; 514/601; 514/605; 514/613; 514/617; 514/625; 514/913
[58] Field of Search ................ 514/18, 236.2, 400, 514/538, 540, 542, 601, 605, 613, 617, 625, 913

[56] References Cited

U.S. PATENT DOCUMENTS

| 4,442,089 | 4/1984 | Horowitz | 424/177 |
| 4,587,258 | 5/1986 | Gold et al. | 514/412 |
| 4,845,079 | 7/1989 | Luly et al. | 514/18 |

FOREIGN PATENT DOCUMENTS

| EP114333 | 8/1984 | European Pat. Off. . |
| EP174162 | 3/1986 | European Pat. Off. . |
| WO87/00055 | 1/1987 | PCT Int'l Appl. . |
| WO87/02581 | 5/1987 | PCT Int'l Appl. . |
| WO87/02585 | 5/1987 | PCT Int'l Appl. . |

Primary Examiner—Frederick E. Waddell
Assistant Examiner—Zohreh A. Fay
Attorney, Agent, or Firm—Steven R. Crowley; Steven F. Weinstock

[57] ABSTRACT

A method and a composition for treating or reducing and/or controlling intraocular pressure comprising administering an effective amount of a renin inhibiting compound of the formula:

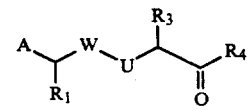

where A is a substituent; W is CO or CHOH and U is $CH_2$ or $NR_2$ wherein $R_2$ is hydrogen or loweralkyl; with the proviso that when W is CHOH then U is $CH_2$; $R_1$ is loweralkyl, cycloalkyl methyl, benzyl, (alpha, alpha)-dimethylbenzyl, 4-hydroxybenzyl, 4-methoxybenzyl, halobenzyl, (1-naphthyl)methyl, (2-naphthyl)methyl, 1-bezyloxyethyl, phenethyl, phenoxy, thiophenoxy or anilino; $R_3$ is loweralkyl, loweralkenyl, ((alkoxy)alkoxy)loweralkyl, (thioalkoxy)alkyl, benzyl or heterocyclic ring substituted methyl; and $R_4$ is substituted hydroxyalkyamino.

7 Claims, No Drawings

GLAUCOMA TREATMENT

TECHNICAL FIELD

This is a division of U.S. patent application Ser. No. 240,567, filed Sept. 8, 1988 now U.S. Pat. No. 4,927,807 which is a continuation in part of U.S. patent application Ser. No. 105,636, filed Oct. 6, 1987.

The present invention relates to compositions, kits and methods of using novel renin inhibiting compounds, separately or in combination with beta adrenergic antagonist agents, steroidal antiinflammatory agents, or angiotensin converting enzyme inhibiting compounds for the treatment of glaucoma or reducing and/or controlling intraocular pressure.

BACKGROUND ART

Glaucoma is a condition characterized by an increase in intraocular pressure. Increased intraocular pressure can lead to optic nerve damage and defects in the visual field. Blindness can result if the condition is left untreated.

For some time two categories of drugs have been used to treat increased intraocular pressure. The first category is known as miotic agents and comprises cholinergic stimulating agents, such as pilocarpine, and cholinesterase antagonists, such as demacarium bromide and echothiopate iodide. Miotic agents are used to facilitate outflow of the aqueous humor.

Pilocarpine has been used topically to treat glaucoma for many years and has no adverse systemic effects. However, localized adverse effects are known. Ciliary spasms may lead to debilitating myopia. Irritation and allergic reactions may require discontinuation of use. Of special concern is the known ability of miotic agents to cause retinal detachment.

The cholinesterase antagonists may have systemic adverse effects including salivation, urinary incontinence, diarrhea, profuse sweating, muscle weakness, respiratory difficulties and cardiac irregularities. Localized effects include irritation, induced myopia and lens opacities.

The second category of drugs used to treat increased intraocular pressure act by inhibiting the secretion of aqueous humor by the ciliary processes. Epinephrine, beta adrenergic antagonists such as timolol and carbonic anhydrase inhibitors such as acetazolamine are members of this second category.

Topical epinephrine must be used with caution in individuals with hyperthyroidism, hypertension, cardiac disease and bronchial asthma, due to possible systemic effects. Topical beta-adrenergic antagonists must also be used with caution due to a variety of systemic effects. Timolol must be used cautiously in patients with asthma, chronic obstructive pulmonary disease or sinus bradycardia. Carbonic anhydrase inhibitors are administered systemically when intraocular pressure cannot be controlled with known topical agents. Agents such as acetazolamide often cause numbness and tingling, drowsiness and loss of appetite.

Recently it has been disclosed (U.S. Pat. No. 4587258, E. H. Gold et al., issued May 6, 1986; U.S. Pat. No. 4442089, Z. P. Horovitz, issued Apr. 10, 1984; PCT Patent Application No. W087/02585, R. W. Watkins et al., published May 7, 1987; PCT Patent Application No. W087/00055, R. W. Watkins et al., published Jan. 15, 1987; European Patent Application No. EP174162, G. Allan et al., published Mar. 12, 1986; European Patent Application No. EP114333, R. W. Watkins, published Aug. 1, 1984) that angiotensin converting enzyme (ACE) inhibitors are useful for treating glaucoma.

When renin is released into the blood from the kidney, the renin-angiotensin system is activated, leading to vasoconstriction and conservation of sodium, both of which result in increased blood pressure. The renin acts on a circulating protein, angiotensinogen, to cleave out a fragment called angiotensin I (AI). AI itself has only slight pharmacologic activity but, after additional cleavage by a second enzyme, angiotensin converting enzyme (ACE), forms the potent molecule angiotensin II (AII). The major pharmacological effects of AII are vasoconstriction and stimulation of the adrenal cortex to release aldosterone, a hormone which causes sodium retention. AII is cleaved by an aminopeptidase to form angiotensin III (AIII), which, compared to AII, is a less potent vasoconstrictor but a more potent inducer of aldosterone release.

The renin-angiotensin system has been modulated or manipulated, in the past, with ACE inhibitors to reduce blood pressure. However, ACE acts on several substrates other than angiotensin I (AI), most notably the kinins which cause such undesirable side effects as pain, "leaky" capillaries, prostaglandin release and a variety of behavioral and neurologic effects. Further, ACE inhibition leads to the accumulation of AI. Although AI has much less vasoconstrictor activity than AII, its presence may negate some of the hypotensive effects of the blockade of AII synthesis.

Most recently it has been disclosed (PCT Patent Application No. W08702581, R. W. Watkins et al., published May 7, 1987) that renin inhibitors are useful for treating glaucoma. There are no known side effects which result when renin is inhibited from acting on its substrate. While much research effort has been directed to developing renin inhibitors, there is still a need for more potent renin inhibitors.

Thus, methods and compositions for treating glaucoma or reducing and/or controlling intraocular pressure which have reduced potential for localized and systemic adverse effects, as well as increased potency, are desirable.

DISCLOSURE OF THE INVENTION

The present invention relates to the use of novel organic compounds and compositions which inhibit renin for treating glaucoma or reducing and/or controlling intraocular pressure. The present invention also relates to the use of novel organic compounds and compositions which inhibit renin in combination with a beta adrenergic antagonist agent or an angiotensin converting enzyme inhibiting compound for treating glaucoma or reducing and/or controlling intraocular pressure.

The present invention also relates to pharmaceutical compositions for treating glaucoma or reducing and/or controlling intraocular pressure comprising renin inhibiting compounds in a pharmaceutically acceptable vehicle. The present invention also relates to pharmaceutical compositions for treating glaucoma or reducing and/or controlling intraocular pressure comprising novel renin inhibiting compounds in combination with a beta adrenergic antagonist agent or an angiotensin converting enzyme inhibiting compound in a pharmaceutically acceptable vehicle.

The present invention also relates to pharmaceutical compositions for treating the increase in intraocular pressure associated with the administration of steroidal antiinflammatory agents comprising novel renin inhibiting compounds in combination with a steroidal antiinflammatory compound in a pharmaceutically acceptable vehicle.

The present invention also relates to a kit comprising in individual containers in a single package a novel renin inhibiting compound in a suitable pharmaceutical vehicle and a steroidal antiinflammatory compound in a suitable pharmaceutical vehicle and/or a beta adrenergic antagonist agent in a suitable pharmaceutical vehicle or an angiotensin converting enzyme inhibiting compound in a suitable pharmaceutical vehicle.

The novel renin inhibiting compounds of the invention and methods for making them have been disclosed in copending U.S. patent application Ser. No. 946,881 filed Jan. 1, 1987; U.S. patent application Ser. No. 946,883 filed Jan. 9, 1987; U.S. patent application Ser. No. 946,882 filed Jan. 9, 1987; U.S. patent application Ser. No. 946,884 filed Jan. 9, 1987; U.S. patent application Ser. No. 943,566 filed Dec. 31, 1986; U.S. patent application Ser. No. 943,567 filed Dec. 31, 1986; U.S. patent application Ser. No. 0097,553 filed Sept. 16, 1987; U.S. patent application Ser. No. 231,869 filed Aug. 16, 1988; and U.S. patent application Ser. No. 132,356 filed Dec. 18, 1987, which are hereby incorporated by reference.

The novel renin inhibiting compounds of the invention and methods for making them have also been disclosed in European Patent Application No. 230266, published July 29, 1987; European Patent Application No. 229667, published July 22, 1987; PCT Patent Application No. WO87/04349, published July 30, 1987; PCT Patent Application No. WO88/05050, published July 14, 1988; and Biochem. Biophys. Res. Comm. 139, 982 (1986).

The novel renin inhibiting compounds of the invention are selected from the group consisting of:

$$A\diagdown_{R_1}\diagup W\diagdown_U\diagdown\underset{R_3}{\overset{|}{C}}\diagdown\underset{\overset{\|}{O}}{C}\diagdown\underset{R_6}{\overset{R_5}{\overset{|}{N}}}\diagdown\underset{R_8}{\overset{HO}{\overset{|}{C}}}\underset{R_9}{\overset{R_7}{|}}\diagdown V\diagdown R_{10}. \quad (1)$$

wherein A is hydrogen, loweralkyl, arylalkyl, $-OR_{20}$ wherein $R_{20}$ is hydrogen, or loweralkyl, $-NR_{21}R_{22}$ wherein $R_{21}$ and $R_{22}$ are independently selected from hydrogen and loweralkyl; or A is $$R_{23}\diagdown\underset{\overset{\|}{O}}{C}\diagdown B- \text{ or } R_{23}\diagdown\underset{\overset{\|}{O}}{\overset{\|}{\underset{\|}{S}}}\diagdown B-$$

wherein B is NH, O, CH$_2$ or NHCH$_2$; and $R_{23}$ is loweralkyl, alkoxy, arylalkoxy, arylalkoxyalkyl, amino, alkylamino, dialkylamino, carboxyalkyl, alkoxycarbonylalkyl, (dihydroxyalkyl)(alkyl)amino, aminoalkyl, N-protected aminoalkyl, (heterocyclic)alkyl, or a substituted or unsubstituted heterocyclic;

W is C=O, CH$_2$ or CHOH;

U is CH$_2$ or NR$_2$, wherein R$_2$ is hydrogen or loweralkyl, provided that when W is CHOH then U is CH$_2$;

R$_1$ is loweralkyl, cycloalkylalkyl, benzyl, 4-methoxybenzyl, 4 hydroxybenzyl, halobenzyl, (1-naphthyl)methyl, (2-naphthyl)methyl, (4 imidazolyl)methyl, (alpha,alpha) dimethylbenzyl, 1 benzyloxyethyl, phenethyl, phenoxy, thiophenoxy or anilino; provided that when R$_1$ is phenoxy, thiophenoxy or anilino, then B is CH$_2$ or A is hydrogen;

R$_3$ is loweralkyl, (thioalkoxy)alkyl, benzyl or heterocyclic ring substituted methyl;

R$_5$ is hydrogen or loweralkyl;

R$_6$ is loweralkyl, cycloalkylmethyl, or benzyl;

R$_7$, R$_8$ and R$_9$ are hydrogen or loweralkyl and may be the same or different;

V is NH, O, S, SO, SO$_2$, or CH$_2$;

R$_{10}$ is loweralkyl, cycloalkyl, (cycloalkyl)alkyl, aryl, arylalkyl or an N-protecting group, or V and R$_{10}$ taken together are N$_3$; with the proviso that R$_{10}$ may be an N-protecting group only when V is NH;

$$A_b\diagdown_{R_{16}}\diagup W_b\diagdown_{U_b}\diagdown\underset{R_{3b}}{\overset{|}{C}}\diagdown\underset{\overset{\|}{O}}{C}\diagdown\underset{R_{6b}}{\overset{R_{5b}}{\overset{|}{N}}}\diagdown R_{13b}\diagdown R_{14b}\diagdown R_{15b}\diagdown L_b\diagdown R_{10b}. \quad (2)$$

wherein A$_b$ is hydrogen, loweralkyl, arylalkyl, OR$_{20b}$ or SR$_{20b}$ wherein R$_{20b}$ is hydrogen, loweralkyl or aminoalkyl, NR$_{21b}$R$_{22b}$ wherein R$_{21b}$ and R$_{22b}$ are independently selected from hydrogen, loweralkyl, aminoalkyl, cyanoalkyl and hydroxyalkyl; or A$_b$ is $$R_{23b}\diagdown\underset{\overset{\|}{O}}{C}\diagdown B_b- \text{ or } R_{23b}\diagdown\underset{\overset{\|}{O}}{\overset{\|}{\underset{\|}{S}}}\diagdown B_b-$$

wherein B$_b$ is NH, alkylamino, S, O, CH$_2$, or CHOH; and R$_{23b}$ is loweralkyl, cycloalkyl, aryl, arylalkyl, alkoxy, alkenyloxy, hydroxyalkoxy, dihydroxyalkoxy, arylalkoxy, arylalkoxyalkyl, amino, alkylamino, dialkylamino, (hydroxyalkyl)(alkyl)amino, (dihydroxyalkyl)(alkyl)amino, aminoalkyl, N-protected aminoalkyl, alkylaminoalkyl, carboxyalkyl, alkoxycarbonylalkyl, (N-protected)(alkyl)aminoalkyl, dialkylaminoalkyl, (heterocyclic)alkyl, or a substituted or unsubstituted heterocyclic;

W$_b$ is C=O or CHOH;

U$_b$ is CH$_2$ or wherein R$_{2b}$ is hydrogen or loweralkyl, provided that when W$_b$ is CHOH then U$_b$ is CH$_2$;

R$_{1b}$ is loweralkyl, cycloalkylalkyl, benzyl, 4-methoxybenzyl, 4-hydroxybenzyl, halobenzyl, (1-naphthyl)methyl, (2-naphthyl)methyl, (4-imidazolyl)methyl, (alpha,alpha)-dimethylbenzyl, 1-benzyloxyethyl, phenethyl, phenoxy, thiophenoxy or anilino; provided that when R$_{1b}$ is phenoxy, thiophenoxy or anilino, then B$_b$ is CH$_2$ or CHOH or A$_b$ is hydrogen;

R$_{3b}$ is loweralkyl, loweralkenyl, benzyl or heterocyclic ring substituted methyl;

R$_{5b}$ is hydrogen or loweralkyl;

R$_{6b}$ is loweralkyl, cycloalkylmethyl, or benzyl;

R$_{10b}$ is loweralkyl, cycloalkyl, (cycloalkyl)alkyl, aryl, arylalkyl or an N-protecting group, or L$_b$ and R$_{10b}$ taken together can be N$_3$, with the proviso that when L$_b$ is NH then R$_{10b}$ is an N-protecting group;

R$_{13b}$ is CHOH or CO;

R$_{14b}$ is CH$_2$, CF$_2$ or CF with the proviso that when R$_{13b}$ is CO then R$_{14b}$ is CF$_2$;

R$_{15b}$ is CH$_2$, CHR$_{25b}$ wherein R$_{25b}$ is loweralkyl, cycloalkyl, cycloalkylalkyl, aryl or arylalkyl, or R$_{14b}$ and R$_{15b}$ taken together can be

with the proviso that when $R_{14}$ is $CF_2$ then $R_{15}$ is $CH_2$;

$L_b$ is O, S, SO, $SO_2$, $NR_{26b}$ wherein $R_{26b}$ is hydrogen or loweralkyl, or $NR_{27b}C(O)$ wherein $R_{27b}$ is hydrogen or loweralkyl;

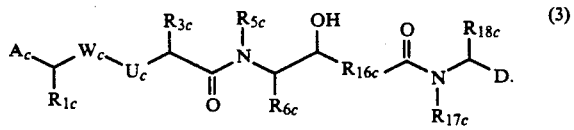

wherein $A_c$ is

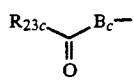

wherein $B_c$ is NH, or $CH_2$; and $R_{23c}$ is loweralkyl, alkoxy, or a substituted or unsubstituted heterocyclic;

$W_c$ is C=O;

$U_c$ is $NR_{2c}$, wherein $R_{2c}$ is hydrogen or loweralkyl;

$R_{1c}$ is loweralkyl, cycloalkylalkyl, benzyl, 4-methoxybenzyl, 4-hydroxybenzyl, halobenzyl, (1-naphthyl)methyl, (2-naphthyl)methyl, (4-imidazolyl)methyl, (alpha,alpha) dimethylbenzyl, 1-benzyloxyethyl, or phenethyl;

$R_{3c}$ is loweralkyl, benzyl or heterocyclic ring substituted methyl;

$R_{5c}$ is hydrogen or loweralkyl;

$R_{6c}$ is loweralkyl, cycloalkylmethyl, benzyl, or $CH_2R_{24c}$, where $R_{24c}$ is selected from 1,3-dioxan-2-yl; 1,3-dioxolan-2-yl, 1,3-dithiolan-2-yl or 1,3-dithian-2-yl;

$R_{16c}$ is $CH_2$, $CF_2$ or $CHR_{63c}$ where $R_{63c}$ is loweralkyl, hydroxy, hydroxyalkyl, alkoxy, allyl, arylalkoxy or thioalkyl;

$R_{17c}$ is hydrogen or loweralkyl;

$R_{18c}$ is loweralkyl or lipophilic or aromatic amino acid side chain;

$D_c$ is hydrogen, loweralkyl or $-CH_2OR_{28c}$, wherein $R_{28c}$ is hydrogen, loweralkyl or arylalkyl;

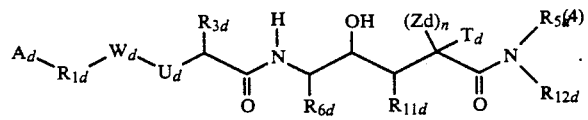

wherein $A_d$ is hydrogen, loweralkyl, arylalkyl, $-OR_{20d}$ or $SR_{20d}$ wherein $R_{20d}$ is hydrogen, loweralkyl or aminoalkyl, $-NR_{21d}R_{22d}$ wherein $R_{21d}$ and $R_{22d}$ are independently selected from hydrogen, loweralkyl, aminoalkyl, cyanoalkyl and hydroxyalkyl; or $A_d$ is

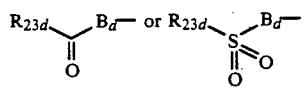

wherein $B_d$ is NH, alkylamino, S, O, $CH_2$, or $NHCH_2$, and $R_{23d}$ is loweralkyl, cycloalkyl, aryl, arylalkyl, alkoxy, alkenyloxy, hydroxyalkoxy, dihydroxyalkoxy, arylalkoxy, arylalkoxyalkyl, amino, alkylamino, dialkylamino, (hydroxyalkyl)(alkyl)amino, ((dialkylamino)alkyl)(alkyl)amino, (dihydroxyalkyl)(alkyl)amino, aminoalkyl, N-protected aminoalkyl, alkylaminoalkyl, carboxyalkyl, alkoxycarbonylalkyl, (N-protected)(alkyl)aminoalkyl, dialkylaminoalkyl, (heterocyclic)alkyl-, or a substituted or unsubstituted heterocyclic;

$W_d$ is C=O or CHOH;

$U_d$ is $CH_2$ or wherein $R_{2d}$ is hydrogen or loweralkyl, provided that when $W_d$ is CHOH then $U_d$ is $CH_2$;

$R_{1d}$ is $CHR_{24d}$ wherein $R_{24d}$ is loweralkyl, cycloalkylalkyl, benzyl, 4-methoxybenzyl, 4-hydroxybenzyl, halobenzyl, (1-naphthyl)methyl, (2-naphthyl)methyl, (4-imidazoyl)methyl, (alpha, alpha) dimethylbenzyl, 1-benzyloxyethyl, or phenethyl, or $R_{1d}$ is C=$CHR_{25d}$ wherein $R_{25d}$ is aryl;

$R_{3d}$ is loweralkyl, alkenyl, benzyl or heterocyclic ring substituted methyl;

$R_{5d}$ is hydrogen or loweralkyl;

$R_{6d}$ is loweralkyl, cycloalkylmethyl, or benzyl;

$R_{11d}$ is hydrogen or hydroxy;

n is 0 or 1; when n is 0 then $T_d$ is alkylidene or alkylidene oxide; and when n is 1 then $Z_d$ is hydrogen or hydroxy and $T_d$ is loweralkyl, hydroxyalkyl, aminoalkyl, haloalkyl, or azidoalkyl;

$R_{2d}$ is hydrogen, loweralkyl, cycloalkylalkyl, arylalkyl, aminoalkyl, or dialkylaminoalkyl;

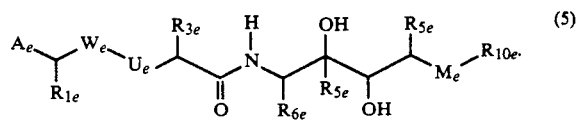

wherein $A_e$ is hydrogen, loweralkyl, arylalkyl, $-OR_{20e}$ or $SR_{20e}$ wherein $R_{20e}$ is hydrogen, loweralkyl or aminoalkyl, $-NR_{21e}R_{22e}$ wherein $R_{21e}$ and $R_{22e}$ are independently selected from hydrogen, loweralkyl, aminoalkyl, cyanoalkyl and hydroxyalkyl; or $A_e$ is wherein $B_e$ is NH, alkylamino, S, O, $CH_2$, or CHOH; and $R_{23e}$ is loweralkyl, cycloalkyl, aryl, arylalkyl, alkoxy, alkenyloxy, hydroxyalkoxy, dihydroxyalkoxy, arylalkoxy, arylalkoxyalkyl, amino, alkylamino, dialkylamino, (hydroxyalkyl)(alkyl)amino, (dihydroxyalkyl)(alkyl)amino, aminoalkyl, N-protected aminoalkyl, alkylaminoalkyl, carboxyalkyl, alkoxycarbonylalkyl, (N-protected)(alkyl)aminoalkyl, dialkylaminoalkyl, (heterocyclic)alkyl, or a substituted or unsubstituted heterocyclic;

$W_e$ is C=O;

$U_e$ is wherein $R_{2e}$ is hydrogen or loweralkyl;

$R_{1e}$ is loweralkyl, cycloalkylalkyl, benzyl, methoxybenzyl, 4-hydroxybenzyl, halobenzyl, (1-naphthyl)methyl, (2-naphthyl)methyl, (4-imidazolyl-)methyl, (alpha,alpha) dimethylbenzyl, 1-benzyloxyethyl, phenethyl, phenoxy, thiophenoxy or anilino, provided that when $R_{1e}$ is phenoxy, thiophenoxy or anilino, then $B_e$ is $CH_2$ or CHOH or $A_e$ is hydrogen;

$R_{3e}$ is loweralkyl, benzyl or heterocyclic ring substituted methyl;

$R_{5e}$ is hydrogen or loweralkyl;

$R_{6e}$ is loweralkyl, cycloalkylmethyl, or benzyl;

$M_e$ is O, NH or S;

$R_{10e}$ is hydrogen, loweralkyl, cycloalkyl, (cycloalkyl)alkyl, aryl, arylalkyl or an N-protecting group;

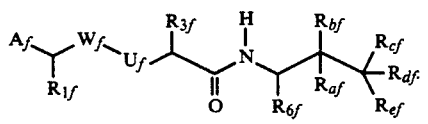 (6)

wherein $A_f$ is hydrogen, loweralkyl, arylalkyl, $-OR_{10f}$ or $-SR_{10f}$ wherein $R_{10f}$ is hydrogen, loweralkyl or aminoalkyl, $-NR_{11f}R_{12f}$ wherein $R_{11f}$ and $R_{12f}$ are independently selected from hydrogen, loweralkyl, aminoalkyl, cyanoalkyl, hydroxyalkyl, carboxyalkyl, alkoxycarbonylalkyl, (amino)carboxyalkyl, ((N-protected)amino)carboxyalkyl, (alkylamino)carboxyalkyl, ((N-protected)alkylamino)carboxyalkyl, (dialkylamino)carboxyalkyl, (amino)alkoxycarbonylalkyl, ((N-protected)amino)alkoxycarbonylalkyl, (alkyamino)alkoxycarbonylalkyl, ((N-protected)alkylamino)alkoxycarbonylalkyl and (dialkylamino)alkoxycarbonylalkyl; or $A_f$ is

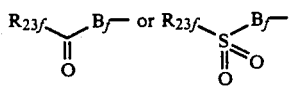

wherein $B_f$ is NH, alkylamino, S, O, CH$_2$ or CHOH and $R_{23f}$ is loweralkyl, cycloalkyl, aryl, arylalkyl, alkoxy, alkenyloxy, hydroxyalkoxy, dihydroxyalkoxy, arylalkoxy, arylalkoxyalkyl, amino, alkylamino, dialkylamino, (hydroxyalkyl)(alkyl)amino, (dihydroxyalkyl)(alkyl)amino, aminoalkyl, N-protected-aminoalkyl, alkylaminoalkyl, (N-protected)(alkyl)aminoalkyl, dialkylaminoalkyl, carboxyalkoxyalkyl, (alkoxycarbonyl)alkoxyalkyl, carboxyalkyl, carboxyalkylamino, alkoxycarbonylalkyl, alkoxycarbonylalkylamino, (amino)carboxyalkyl, (amino)carboxyalkylamino, ((N-protected)amino)carboxyalkyl, ((N-protected)amino)-carboxyalkyamino, (alkylamino)carboxyalkyl, (alkylamino)carboxyalkylamino, ((N-protected)alkylamino)-carboxyalkyl, ((N-protected)alkylamino)carboxyalkylamino, (dialkylamino)carboxyalkyl, (dialkylamino)carboxyalkylamino, (amino)alkoxycarbonylalkyl, (amino)alkoxycarbonylalkylamino, ((N-protected)amino)alkoxycarbonylalkyl, ((N-protected)amino) alkoxycarbonylalkylamino, (alkylamino)alkoxycarbonylalkyl, (alkylamino)alkoxycarbonylalkylamino, ((N-protected)alkylamino)- alkoxycarbonylalkyl, ((N-protected)alkylamino)alkoxycarbonyl-alkylamino, (dialkylamino)alkoxycarbonylalkyl, (dialkylamino)alkoxycarbonylalkylamino, aminocycloalkyl, aminoalkylamino, dialkylaminoalkyl(alkyl)amino, arylalkylamino, arylalkyl(alkyl)amino, alkoxyalkyl(alkyl)amino, (polyalkyoxy)alkyl(alkyl)amino, di-(alkoxyalkyl)amino, di-(hydroxyalkyl)amino, di-((polyalkoxy)alkyl)amino, polyalkoxy, (polyalkoxy)alkyl, (heterocyclic)alkyl or a substituted or unsubstituted heterocyclic wherein saturated heterocyclics may be unsubstituted, monosubstituted or disubstituted with hydroxy, oxo, amino, alkylamino, dialkylamino, alkoxy, polyalkoxy or loweralkyl; unsaturated heterocyclics may be unsubstituted or monosubstituted with hydroxy, amino, alkylamino, dialkylamino, alkoxy, polyalkoxy or loweralkyl;

$W_f$ is C=O or CHOH;

$U_f$ is CH$_2$ or NR$_2$, provided that when $W_f$ is CHOH then $U_f$ is CH$_2$;

$R_{1f}$ is loweralkyl, cycloalkylmethyl, benzyl, 4-methoxybenzyl, halobenzyl, (1-naphthyl)methyl, (2-naphthyl)methyl, (4-imidazolyl)methyl, (alpha,alpha) dimethylbenzyl, 1-benzyloxyethyl, phenethyl, phenoxy, thiophenoxy or anilino; provided that when $R_{1f}$ is phenoxy, thiophenoxy or anilino, then $B_f$ is CH$_2$ or CHOH or $A_f$ is hydrogen;

$R_{2f}$ is hydrogen or loweralkyl;

$R_{3f}$ is loweralkyl, loweralkenyl, ((alkoxy)alkoxy)loweralkyl, (thioalkoxy)alkyl, benzyl or heterocyclic ring substituted methyl;

$R_{6f}$ is loweralkyl, cycloalkylmethyl or benzyl;

$R_{af}$ is vinyl, formyl, hydroxymethyl or hydrogen;

$R_{df}$ is hydrogen or loweralkyl;

$R_{bf}$ and $R_{ef}$ are independently selected from OH and NH$_2$; and $R_{cf}$ is hydrogen, loweralkyl, vinyl or arylalkyl;

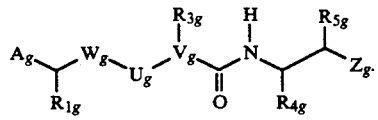 (7)

wherein $A_g$ is hydrogen, loweralkyl, aminoalkyl, (alkyl)aminoalkyl, dialkylaminoalkyl, (alkoxy)aminoalkyl, (alkoxy)(alkyl)aminoalkyl, phenylalkyl, (substituted phenyl)alkyl wherein the phenyl ring is substituted with one, two or three substituents independently selected from loweralkoxy, loweralkyl, amino, alkylamino, dialkylamino, hydroxy, halo, mercapto, nitro, thioalkoxy, carboxaldehyde, carboxy, alkoxycarbonyl and carboxamide, naphthylalkyl, (substituted naphthyl)alkyl wherein the naphthyl ring is substituted with one, two or three substituents independently selected from loweralkoxy, loweralkyl, amino, alkylamino, dialkylamino, hydroxy, halo, mercapto, nitro, thioalkoxy, carboxaldehyde, carboxy, alkoxycarbonyl and carboxamide, substituted or unsubstituted heterocyclic, where saturated heterocyclics may be unsubstituted, monosubstituted or disubstituted with hydroxy, oxo, amino, alkylamino, dialkylamino, alkoxy, polyalkoxy, loweralkyl, haloalkyl or polyhaloalkyl; unsaturated heterocyclics may be unsubstituted or monosubstituted with hydroxy, amino, alkylamino, dialkylamino, alkoxy, polyalkoxy, loweralkyl, haloalkyl or polyhaloalkyl, or $A_g$ is (unsubstituted heterocyclic)alkyl or (substituted heterocyclic)alkyl wherein unsubstituted or substituted heterocyclic is as defined above, or $A_g$ is $-OR_{7g}$ or $-SR_{7g}$ wherein $R_{7g}$ is hydrogen, loweralkyl, aminoalkyl, (alkyl)aminoalkyl, dialkylaminoalkyl, (alkoxy)aminoalkyl, (alkoxy)(alkyl)aminoalkyl, phenylalkyl, (substituted phenyl)alkyl wherein substituted phenyl is as defined above, naphthylalkyl, (substituted naphthyl)alkyl wherein the substituted naphthyl is as defined above, substituted or unsubstituted heterocyclic as defined above, (unsubstituted heterocyclic)alkyl or (substituted heterocyclic)alkyl wherein unsubstituted or substituted heterocyclic is as defined above, (unsubstituted heterocyclic)C(O)- or (substituted heterocyclic)C(O)- wherein unsubstituted or substituted heterocyclic is as defined above; or $A_g$ is $-NR_{8g}R_{9g}$ wherein $R_{8g}$ and $R_{9g}$ are independently selected from hydrogen, hydroxy, alkoxy, loweralkyl, aminoalkyl, cyanoalkyl and hydroxyalkyl; or $A_g$ is

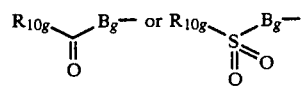

wherein $B_g$ is NH, alkylamino, S, O, CH$_2$, NHCH$_2$ or CH(OR$_{52g}$) wherein $R_{52g}$ is hydrogen, loweralkyl or loweralkylcarbonyl, and R$_{10g}$ is hydrogen, loweralkyl, cycloalkyl, phenyl, substituted phenyl as defined above, naphthyl, substituted naphthyl as defined above, alkoxy, alkenyloxy, hydroxyalkoxy, dihydroxyalkoxy, phenylalkoxy, (substituted phenyl)alkoxy wherein substituted phenyl is as defined above, naphthylalkoxy, (substituted naphthyl)alkoxy wherein substituted naphthyl is as defined above, phenylalkoxyalkyl, (substituted phenyl)alkoxyalkyl wherein substituted phenyl is as defined above, naphthylalkoxyalkyl, (substituted naphthyl)alkoxyalkyl wherein substituted naphthyl is as defined above, thioalkoxyalkyl, loweralkylsulfinylalkyl, loweralkylsulfonylalkyl, phenylthioalkyl, (substituted phenyl)thioalkyl wherein substituted phenyl is as defined above, naphthylthioalkyl, (substituted naphthyl)thioalkyl wherein substituted naphthyl is as defined above, phenylsulfonylalkyl, (substituted phenyl)sulfonylalkyl wherein substituted phenyl is as defined above, naphthylsulfonylalkyl, (substituted naphthyl)sulfonylalkyl wherein substituted naphthyl is as defined above, amino, alkylamino, dialkylamino, (hydroxyalkyl)(alkyl)amino, (dihydroxyalkyl)(alkyl)amino, aminoalkyl, alkoxycarbonylalkyl, carboxyalkyl, (N-protected)aminoalkyl, alkylaminoalkyl, (N-protected)(alkyl)aminoalkyl, dialkylaminoalkyl, (heterocyclic)alkyl, a substituted or unsubstituted heterocyclic as defined above, aminocycloalkyl, aminoalkylamino, (dialkylaminoalkyl)(alkyl)amino, phenylalkylamino, (substituted phenyl)alkylamino wherein substituted phenyl is as defined above, naphthylalkylamino, (substituted naphthyl)alkylamino wherein substituted naphthyl is as defined above, (phenylalkyl)(alkyl)amino, ((substituted phenyl)alkyl)(alkyl)amino wherein substituted phenyl is as defined above, (naphthylalkyl)(alkyl)amino, ((substituted naphthyl)alkyl)(alkyl)amino wherein substituted naphthyl is as defined above, alkoxyalkyl(alkyl)amino, (polyalkoxy)alkyl(alkyl)amino, di-(alkoxyalkyl)amino, di-(hydroxyalkyl)amino, di-((polyalkoxy)alkyl)amino, ((heterocyclic)alkyl)(alkyl)amino, ((heterocyclic)alkyl)amino, (heterocyclic)(alkyl)amino, (alkylaminoalkyl)(alkyl)amino, (dialkylaminoalkyl)(alkyl)amino, ((alkoxy)(alkyl)aminoalkyl)(alkyl)amino, ((alkoxy)aminoalkyl)(alkyl)amino, polyalkoxy or (polyalkoxy)alkyl; or A$_g$ is R$_{41g}$CH(OH)CH$_2$- or R$_{41g}$CH(OH)CH(OH)- wherein R$_{41g}$ is loweralkyl, cycloalkyl, phenyl, substituted phenyl as defined above, naphthyl, substituted naphthyl as defined above, phenylalkyl, (substituted phenyl)alkyl wherein substituted phenyl is as defined above, naphthylalkyl, (substituted naphthyl)alkyl wherein substituted naphthyl is as defined above, phenylalkoxyalkyl, (substituted phenyl)alkoxyalkyl wherein substituted phenyl is as defined above, naphthylalkoxyalkyl, (substituted naphthyl)alkoxyalkyl wherein substituted naphthyl is as defined above, thioalkoxyalkyl, loweralkylsulfinylalkyl, loweralkylsulfonylalkyl, phenylthioalkyl, (substituted phenyl)thioalkyl wherein substituted phenyl is as defined above, naphthylthioalkyl, (substituted naphthyl)thioalkyl wherein substituted naphthyl is as defined above, phenylsulfonylalkyl, (substituted phenyl)sulfonylalkyl wherein substituted phenyl is as defined above, naphthylsulfonylalkyl, (substituted naphthyl)sulfonylalkyl wherein substituted naphthyl is as defined above, aminoalkyl, alkoxycarbonylalkyl, carboxyalkyl, (N-protected)aminoalkyl, alkylaminoalkyl, (N-protected)(alkyl)aminoalkyl, dialkylaminoalkyl, heterocyclicalkyl, a substituted or unsubstituted heterocyclic as defined above, aminocycloalkyl or (polyalkoxy)alkyl;

W$_g$ is C=O, CHOH or NR$_{2g}$ wherein R$_{2g}$ is hydrogen or loweralkyl;

U$_g$ is C=O, CH$_2$ or NR$_{2g}$ wherein R$_{2g}$ is hydrogen or loweralkyl, with the proviso that when W$_g$ is CHOH then U$_g$ is CH$_2$ and with the proviso that U$_g$ is C=O or CH$_2$ when W$_g$ is NR$_{2g}$;

V$_g$ is CH, C(OH) or C(halogen) with the proviso that V$_g$ is CH when U$_g$ is NR$_{2g}$;

R$_{1g}$ is loweralkyl, cycloalkylalkyl, benzyl, (alpha, alpha)-dimethylbenzyl, 4-methoxybenzyl, halobenzyl, 4-hydroxybenzyl, (1-naphthyl)methyl, (2-naphthyl)methyl, (unsubstituted heterocyclic)methyl, (substituted heterocyclic)methyl wherein unsubstituted or substituted heterocyclic is as defined above, phenethyl, 1-benzyloxyethyl, phenoxy, thiophenoxy or anilino, provided that B$_g$ is CH$_2$ or CHOH or A$_g$ is hydrogen when R$_{1g}$ is phenoxy, thiophenoxy or anilino;

R$_{3g}$ is loweralkyl, loweralkenyl, ((alkoxy)alkoxy)alkyl, carboxyalkyl, (thioalkoxy)alkyl, azidoalkyl, aminoalkyl, (alkyl)aminoalkyl, dialkylaminoalkyl, (alkoxy)(alkyl)aminoalkyl, (alkoxy)aminoalkyl, benzyl or heterocyclic ring substituted methyl;

R$_{4g}$ is loweralkyl, cycloalkylmethyl or benzyl;

R$_{5g}$ is OH or NH$_2$; and

Z$_g$ is

<chemical structure: CH connected to CH$_2$-G$_g$ ring with M$_g$-T$_g$-E$_g$; or CH(OH)CH$_2$-Q$_g$-R$_{49g}$> wherein M$_g$ is O, S or NH, T$_g$ is C=O, C=S, S, S(O), S(O)$_2$ or CH$_2$, E is O, S, NR$_{6g}$ wherein R$_{6g}$ is hydrogen, loweralkyl, hydroxyalkyl, hydroxy, alkoxy, amino, or alkylamino, or E$_g$ is CR$_{6g}$R$_{42g}$ wherein R$_{6g}$ is as defined above and R$_{42g}$ is hydrogen or loweralkyl or E$_g$ is C=CR$_{43g}$R$_{44g}$ wherein R$_{43g}$ and R$_{44g}$ are independently selected from hydrogen and loweralkyl, G$_g$ is absent, CH$_2$, or NR$_{11g}$ wherein R$_{11g}$ is hydrogen or loweralkyl, with the proviso that when G$_g$ is NR$_{11g}$ then R$_{6g}$ is loweralkyl or hydroxyalkyl, Q$_g$ is CR$_{45g}$R$_{46g}$ wherein R$_{45g}$ and R$_{46g}$ are independently selected from hydrogen and loweralkyl or Q$_g$ is C=CR$_{47g}$R$_{48g}$ wherein R$_{47g}$ and R$_{48g}$ are independently selected from hydrogen and loweralkyl, and R$_{49g}$ is -CH$_2$OH, carboxy, alkoxycarbonyl or -CONR$_{50g}$R$_{51g}$ wherein R$_{50g}$ is hydrogen or loweralkyl and R$_{51g}$ is hydrogen, loweralkyl, aminoalkyl, alkylaminoalkyl, dialkylaminoalkyl or alkoxyalkyl; and <chemical structure (8): A$_h$-CH(R$_{1h}$)-W$_h$-U$_h$-CH(R$_{3h}$)-C(=O)-N(R$_{5h}$)-CH(R$_{6h}$)-N(H)-CH(R$_{5h}$)-C(=O)-N(H)-R$_{5h}$> wherein A$_h$ is hydrogen, loweralkyl, arylalkyl, -OR$_{20h}$ or -SR$_{20h}$ wherein R$_{20h}$ is hydrogen, loweralkyl or aminoalkyl, -NR$_{21h}$R$_{22h}$ wherein R$_{21h}$ and R$_{22h}$ are independently selected from hydrogen, loweralkyl, aminoalkyl, cyanoalkyl and hydroxyalkyl; or A$_h$ is <chemical structure: R$_{23h}$-C(=O)-B$_h$- or R$_{23h}$-S(=O)$_2$-B$_h$-> wherein $B_h$ is NH, alkylamino, S, O, $CH_2$, $NHCH_2$ or CHOH; and $R_{23h}$ is loweralkyl, cycloalkyl, aryl, arylalkyl, alkoxy, alkenyloxy, hydroxyalkoxy, dihydroxyalkoxy, arylalkoxy, arylalkoxyalkyl, amino, alkylamino, dialkylamino, (hydroxyalkyl)(alkyl)amino, ((dialkylamino)alkyl)(alkyl)amino, (dihydroxyalkyl)(alkyl)amino, N-protected aminoalkyl, alkylaminoalkyl, aminoalkyl, (N-protected)(alkyl)aminoalkyl, dialkylaminoalkyl, (heterocyclic)alkyl, or a substituted or unsubstituted heterocyclic;

$W_h$ is C=O or CHOH;

$U_h$ is $CH_2$ or $NR_{2h}$, wherein $R_{2h}$ is hydrogen or loweralkyl, provided that when $W_h$ is CHOH then $U_h$ is $CH_2$;

$R_{1h}$ is loweralkyl, cycloalkylalkyl, benzyl, 4-methoxybenzyl, 4-hydroxybenzyl, halobenzyl, (1-naphthyl)methyl, (2-naphthyl)methyl, (4-imidazolyl)methyl, (alpha,alpha)-dimethylbenzyl, 1-benzyloxyethyl, phenethyl, phenoxy, thiophenoxy or L anilino, provided that when $R_{1h}$ is phenoxy, thiophenoxy or anilino, then $B_h$ is $CH_2$ or CHOH or $A_h$ is hydrogen;

$R_{3h}$ is loweralkyl, loweralkenyl, ((alkoxy)alkoxy)alkyl, carboxyalkyl, (thioalkoxy)alkyl, benzyl or heterocyclic ring substituted methyl;

$R_{5h}$ is hydrogen or loweralkyl;

$R_{6h}$ is loweralkyl, cycloalkylmethyl, or benzyl; or pharmaceutically acceptable salts or esters thereof.

The term "loweralkyl" as used herein refers to straight or branched chain alkyl radicals containing from 1 to 7 carbon atoms including but not limited to methyl, ethyl, n-propyl, iso-propyl, n-butyl, iso-butyl, sec-butyl, n-pentyl, 2-methylbutyl, 2,2-dimethylpropyl, n-hexyl, 2-methyl-pentyl, 2,2-dimethylbutyl, n-heptyl, 2-methylhexyl and the like.

The term "cycloalkyl" as used herein refers to an aliphatic ring having 3 to 7 carbon atoms.

The term "cycloalkylalkyl" as used herein refers to a cycloalkyl residue appended to a loweralkyl radical and includes but is not limited to cyclohexylmethyl and cyclopentylmethyl.

The term "arylalkyl" as used herein refers to an unsubstituted or substituted aromatic ring, substituted with one, two or three substituents selected from loweralkoxy, loweralkyl, amino, loweralkylamino, hydroxy, halogen, mercapto, nitro, thioalkoxy, carboxaldehyde, carboxyl, carboalkoxy and carboxamide; appended to a loweralkyl radical, including but not limited to benzyl, 1- and 2-naphthylmethyl, halobenzyl, and alkoxybenzyl.

The term "phenylalkyl" as used herein refers to a phenyl group appended to a loweralkyl radical, including, but not limited to benzyl, phenethyl and the like.

The term "(substituted phenyl)alkyl" as used herein refers to a substituted phenyl group appended to a loweralkyl radical wherein the phenyl ring is substituted with one, two or three substituents chosen from the group loweralkoxy, loweralkyl, amino, loweralkylamino, hydroxy, halo, mercapto, nitro, thioalkoxy, carboxaldehyde, carboxy, carboalkoxy and carboxamide, including, but not limited to halobenzyl, alkoxybenzyl and the like.

The term "naphthylalkyl" as used herein refers to a naphthyl group appended to a loweralkyl radical, including, but not limited to 1-naphthylmethyl, 2-naphthylmethyl and the like.

The term "(substituted naphthyl)alkyl" as used herein refers to a substituted naphthyl group appended to a loweralkyl radical wherein the naphthyl ring is substituted with one, two or three substituents chosen from the group loweralkoxy, loweralkyl, amino, loweralkylamino, hydroxy, halo, mercapto, nitro, thioalkoxy, carboxaldehyde, carboxy, carboalkoxy and carboxamide, including, but not limited to halonaphthylmethyl, alkoxynaphthylmethyl and the like.

The term "(heterocyclic)alkyl" as used herein refers to an unsubstituted or substituted heterocyclic ring as defined below appended to a loweralkyl radical, including, but not limited to imidazolylmethyl, thiazolylmethyl and the like.

The term "hydroxyalkyl" as used herein refers to -OH appended to a loweralkyl radical.

The term "alkoxyalkyl" as used herein refers to an alkoxy group appended to a loweralkyl radical.

The term "arylalkoxyalkyl" as used herein refers to an arylalkoxy appended to a loweralkyl radical.

The term "phenylalkoxyalkyl" as used herein refers to a phenylalkoxy group appended to a loweralkyl radical, including, but not limited to phenylmethoxymethyl and the like.

The term "(substituted phenyl)alkoxyalkyl" as used herein refers to a (substituted phenyl)alkoxy group appended to a loweralkyl radical, including, but not limited to 4-chlorophenylmethoxymethyl.

The term "naphthylalkoxyalkyl" as used herein refers to a naphthylalkoxy group appended to a loweralkyl radical, including, but not limited to 1-naphthylmethoxymethyl and the like.

The term "(substituted naphthyl)alkoxyalkyl" as used herein refers to a (substituted naphthyl)alkoxy group appended to a loweralky radical, including, but not limited to halonaphthylmethoxymethyl and the like.

The term "thioalkoxyalkyl" as used herein refers to a thioalkoxy group appended to a loweralkyl radical.

The term "((alkoxy)alkoxy)alkyl" as used herein refers to an alkoxy group appended to an alkoxy group which is appended to a loweralkyl radical, including, but not limited to methoxymethoxymethyl and the like.

The term "polyalkoxyalkyl" as used herein refers to a polyalkoxy residue appended to a loweralkyl radical, including, but not limited to methoxyethoxymethoxymethyl and the like.

The term "aminoalkyl" as used herein refers to $-NH_2$ appended to a loweralkyl radical.

The term "alkylaminoalkyl" as used herein refers to $-NHR_{70}$ appended to a loweralkyl radical, wherein $R_{70}$ is a loweralkyl radical.

The term "dialkylaminoalkyl" as used herein refers to a dialkylamino appended to a loweralkyl radical.

The term "aminocycloalkyl" as used herein refers to an $-NH_2$ appended to a cycloalkyl radical.

The term "N-protected aminoalkyl" as used herein refers to $-NHR_{71}$ appended to a loweralkyl group, wherein $R_{71}$ is an N-protecting group.

The term "(N-protected)(alkyl)amino alkyl" as used herein refers to $NR_{71}R_{72}$ which is appended to a loweralkyl radical, wherein $R_{71}$ is defined as above and $R_{72}$ is a loweralkyl group.

The term "alkoxycarbonylalkyl" as used herein refers to $R_{73}COR_{74}-$, wherein $R_{73}$ is an alkoxy group and $R_{74}$ is a loweralkyl radical.

The term "carboxyalkyl" as used herein refers to a carboxylic acid group (-COOH) appended to a loweralkyl radical.

The term "cyanoalkyl" as used herein refers to -CN appended to a loweralkyl radical.

The term "azidoalkyl" as used herein refers to -N$_3$ appended to a loweralkyl radical.

The term "(alkoxy)aminoalkyl" as used herein refers to an alkoxy group appended to an amino group which in turn is appended to a loweralkyl radical.

The term "(alkoxy)(alkyl)aminoalkyl" as used herein refers to an -NR$_{75}$R$_{76}$ group appended to a loweralkyl radical wherein R$_{75}$ is an alkoxy group and R$_{76}$ is a loweralkyl group.

The term "loweralkylsulfinylalkyl" as used herein refers to a R$_{77}$S(O)- group appended to a loweralkyl radical wherein R$_{77}$ is a loweralkyl group.

The term "loweralkylsulfonylalkyl" as used herein refers to a R$_{78}$S(O)$_2$- group appended to a loweralkyl radical wherein R$_{78}$ is a loweralkyl group.

The term "phenylthioalkyl" as used herein refers to a R$_{79}$S- group appended to a loweralkyl radical wherein R$_{79}$ is a phenyl group.

The term "(substituted phenyl)thioalkyl" as used herein refers to a R$_{80}$S- group appended to a loweralkyl radical wherein R$_{80}$ is a substituted phenyl group.

The term "naphthyl thioalkyl" as used herein refers to a R$_{81}$S- group appended to a loweralkyl radical wherein R$_{81}$ is a naphthyl group.

The term "(substituted naphthyl)thioalkyl" as used herein refers to a R$_{82}$S- group appended to a loweralkyl radical wherein R$_{82}$ is a substituted naphthyl group.

The term "phenylsulfonylalkyl" as used herein refers to a R$_{83}$S(O)$_2$- group appended to a loweralkyl radical wherein R$_{83}$ is a phenyl group The term "(substituted phenyl)sulfonylalkyl" as used herein refers to a R$_{84}$S(O)$_2$- group appended to a loweralkyl radical wherein R$_{84}$ is a substituted phenyl group.

The term "naphthylsulfonylalkyl" as used herein refers to a R$_{85}$S(O)$_2$- group appended to a loweralkyl group wherein R$_{85}$ is a naphthyl group.

The term "(substituted naphthyl)sulfonylalkyl" as used refers to a R$_{86}$S(O)$_2$- group appended to a loweralkyl group wherein R$_{86}$ is a substituted naphthyl group.

The term "carboxyalkoxyalkyl" as used herein refers to a carboxylic acid group (-COOH) appended to an alkoxy group which is appended to a loweralkyl radical.

The term "alkoxycarbonylalkoxyalkyl" as used herein refers to an alkoxycarbonyl group (R$_{87}$CO- wherein R$_{87}$ is an alkoxy group) appended to an alkoxy group which is appended to a loweralkyl radical.

The term "(amino)carboxyalkyl" as used herein refers to a loweralkyl radical to which is appended a carboxylic acid group (-COOH) and an amino group (-NH$_2$).

The term "((N-protected)amino)carboxyalkyl" as used herein refers to a loweralkyl radical to which is appended a carboxylic acid group (-COOH) and -NHR$_{88}$ wherein R$_{88}$ is an N-protecting group.

The term "(alkylamino)carboxyalkyl" as used herein refers to a loweralkyl radical to which is appended a carboxylic acid group (-COOH) and an alkylamino group.

The term "((N-protected)alkylamino)-carboxyalkyl" as used herein refers to a loweralkyl radical to which is appended a carboxylic acid group (-COOH) and an -NR$_{89}$R$_{90}$ wherein R$_{89}$ is as defined above and R$_{90}$ is a loweralkyl group.

The term "(dialkylamino)carboxyalkyl" as used herein refers to a loweralkyl radical to which is appended a carboxylic acid group (-COOH) and -NR$_{91}$R$_{92}$ wherein R$_{91}$ and R$_{92}$ are independently selected from loweralkyl.

The term "(amino)alkoxycarbonylalkyl" as used herein refers to a loweralkyl radical to which is appended an alkoxycarbonyl group as defined above and an amino group (-NH$_2$).

The term "((N-protected)amino)alkoxycarbonylalkyl" as used herein refers to a loweralkyl radical to which is appended an alkoxycarbonyl group as defined above and -NHR$_{93}$ wherein R$_{93}$ is as defined above.

The term "(alkylamino)alkoxycarbonylalkyl" as used herein refers to a loweralkyl radical to which is appended an alkoxycarbonyl group as defined above and an alkylamino group as defined above.

The term "((N-protected)alkylamino)-alkoxycarbonylalkyl" as used herein refers to a loweralkyl radical to which is appended an alkoxycarbonyl group as defined above and -NR$_{94}$R$_{95}$ wherein R$_{94}$ is an N-protecting group and R$_{95}$ is a loweralkyl group.

The term "(dialkylamino)alkoxycarbonylalkyl" as used herein refers to a loweralkyl radical to which is appended an alkoxycarbonyl group as defined above and -NR$_{96}$R$_{97}$ wherein R$_{96}$ and R$_{97}$ are independently selected from loweralkyl.

The term "carboxyalkylamino" as used herein refers to -NHR$_{98}$ wherein R$_{98}$ is a carboxyalkyl group.

The term "alkoxycarbonylalkylamino" as used herein refers to -NHR$_{99}$ wherein R$_{99}$ is an alkoxycarbonylakyl group.

The term "(amino)carboxyalkylamino" as used herein refers to -NHR$_{100}$ wherein R$_{100}$ is an (amino)carboxyalkyl group.

The term "((N-protected)amino)carboxyalkylamino" as used herein refers to -NHR$_{101}$ wherein R$_{101}$ is an ((N-protected)amino)carboxyalkyl group.

The term "(alkylamino)carboxyalkylamino" as used herein refers to -NHR$_{102}$ wherein R$_{102}$ is an (alkylamino)carboxyalkyl group.

The term "((N-protected)alkylamino)carboxyalkylamino" as used herein refers to -NHR$_{103}$ wherein R$_{103}$ is an ((N-protected)alkylamino)carboxyalkyl group.

The term "(dialkylamino)carboxyalkylamino" as used herein refers to -NHR$_{104}$ wherein R$_{104}$ is a (dialkylamino)carboxyalkyl group.

The term "(amino)alkoxycarbonylalkylamino" as used herein refers to -NHR$_{105}$ wherein R$_{105}$ is an (amino)alkoxycarbonylalkyl group.

The term "((N-protected)amino)alkoxycarbonylalkylamino" as used herein refers to -NHR$_{106}$ wherein R$_{106}$ is an ((N-protected)amino)alkoxycarbonylalkyl group.

The term "(alkylamino)alkoxycarbonylalkylamino" as used herein refers to -NHR$_{107}$ wherein R$_{107}$ is an (alkylamino)alkoxycarbonylalkyl group.

The term "((N-protected)alkyl-amino)alkoxycarbonylalkylamino" as used herein refers to -NHR$_{108}$ wherein R$_{108}$ is an ((N-protected)alkylamino)alkoxycarbonylalkyl group.

The term "(dialkylamino)alkoxycarbonylalkylamino" as used herein refers to -NHR$_{109}$ wherein R$_{109}$ is a (dialkylamino)alkoxycarbonyl-alkyl group.

The term "alkylidene" as used herein refers to a straight or branched chain alkyl radical which is attached via a carbon-carbon double bond and includes but is not limited to methylidene, ethylidene, 1-propylidene, 1-butylidene, 1-pentylidene, 2-propylidene, 2- butylidene, 2-pentylidene, 3-pentylidene, 3-hexylidene, 3-heptylidene and 4-heptylidene.

The term "alkylidene oxide" as used herein refers to an epoxide moiety which is derived from an alkylidene group.

The term "amino" as used herein refers to an $-NH_2$ substituent.

The term "alkylamino" as used herein refers to $-NHR_{110}$, wherein $R_{110}$ is a loweralkyl group.

The term "dialkylamino" as used herein refers to $-NR_{111}R_{112}$, wherein $R_{111}$ and $R_{112}$ are independently selected from loweralkyl groups.

The term "arylalkylamino" as used herein refers to $R_{113}NH-$, wherein $R_{113}$ is an arylalkyl residue.

The term "arylalkyl(alkyl)amino" as used herein refers to $R_{114}R_{115}N-$, wherein $R_{114}$ is an arylalkyl residue and $R_{115}$ is a loweralkyl residue.

The term "phenylalkylamino" as used herein refers to a phenylalkyl group appended to an amino radical, including, but not limited to benzylamino and the like.

The term "(substituted phenyl)alkylamino" as used herein refers to a (substituted phenyl)alkyl group appended to an amino radical, including, but not limited to 4-chlorobenzylamino and the like.

The term "napthylalkylamino" as used herein refers to a naphthylalkyl group appended to an amino radical, including, but not limited to 1-naphthylmethylamino and the like.

The term "(substituted naphthyl)alkylamino" as used herein refers to a (substituted naphthyl)alkyl group appended to an amino radical.

The term "(phenylalkyl)(alkyl)amino" as used herein refers to $R_{116}R_{117}N-$, wherein $R_{116}$ is a phenylalkyl residue and $R_{117}$ is a loweralkyl residue.

The term "((substituted phenyl)alkyl)-(alkyl)amino" as used herein refers to $R_{118}R_{119}N-$ wherein $R_{118}$ is a (substituted phenyl)alkyl group and $R_{119}$ is a loweralkyl group.

The term "(naphthylalkyl)(alkyl)amino" as used herein refers to $R_{120}R_{121}N-$ wherein $R_{120}$ is a naphthylalkyl group and $R_{121}$ is a loweralkyl group.

The term "((substituted naphthyl)alkyl)-(alkyl)amino" as used herein refers to $R_{122}R_{123}N-$ wherein $R_{122}$ is a (substituted naphthyl)alkyl group and $R_{123}$ is a loweralkyl group.

The term "aminoalkylamino" as used herein refers to $R_{124}NH-$ where $R_{124}$ is an aminoalkyl residue.

The term "dialkylamino(alkyl)amino" as used herein refers to $R_{125}R_{126}N-$, wherein $R_{125}$ is a dialkylamino residue appended to a loweralkyl residue and $R_{126}$ is a loweralkyl residue.

The term "((dialkylamino)alkyl)(alkyl)amino" as used herein refers to $-NR_{127}R_{128}$ wherein $R_{127}$ is a dialkylamino residue appended to a loweralkyl residue and $R_{128}$ is a loweralkyl residue.

The term "(hydroxyalkyl)(alkyl)amino" as used herein refers to $-NR_{129}R_{130}$ wherein $R_{129}$ is a hydroxyalkyl group and $R_{130}$ is a loweralkyl group.

The term "(di hydroxyalkyl)(alkyl)amino" as used herein refers to a loweralkyl group which is disubstituted with -OH radicals appended to an amino group, which amino group also has appended another loweralkyl group.

The term "di-(hydroxyalkyl)amino" as used herein refers to $R_{131}R_{132}N-$, wherein $R_{131}$ and $R_{132}$ are hydroxyalkyl residues.

The term "alkoxyalkyl(alkyl)amino" as used herein refers to $R_{133}R_{134}N-$, wherein $R_{133}$ is a loweralkyl group and $R_{134}$ is an alkoxyalkyl group.

The term "di-(alkoxyalkyl)amino" as used herein refers to $R_{135}R_{136}N-$, wherein $R_{135}$ and $R_{136}$ are alkoxy residues appended to loweralkyl residues.

The term "di-(polyalkoxyalkyl)amino" as used herein refers to $R_{137}R_{138}N-$, wherein $R_{137}$ and $R_{138}$ are polyalkoxy residues appended to loweralkyl residues.

The term "((polyalkoxy)alkyl)(alkyl)amino" as used herein refers to $R_{139}R_{140}N-$, wherein $R_{139}$ is a polyalkoxy residue appended to a loweralkyl radical and $R_{140}$ is a loweralkyl residue.

The term "((heterocyclic)alkyl)(alkyl)amino" as used herein refers to $-NR_{141}R_{142}$ wherein $R_{141}$ is a heterocyclicalkyl group and $R_{142}$ is a loweralkyl group.

The term "(heterocyclicalkyl)amino" as used herein refers to $-NHR_{143}$ wherein $R_{143}$ is a heterocyclic alkyl group.

The term "(heterocyclic)(alkyl)amino" as used herein refers to $-NR_{144}R_{145}$ wherein $R_{144}$ is a substituted or unsubstituted heterocyclic group and $R_{145}$ is a loweralkyl group.

The term "(alkylaminoalkyl)(alkyl)amino" as used herein refers to $-NR_{146}R_{147}$ wherein $R_{146}$ is an alkylaminoalkyl group and $R_{147}$ is a loweralkyl group.

The term "(dialkylaminoalkyl)(alkyl)amino" as used herein refers to $-NR_{148}R_{149}$ wherein $R_{148}$ is a dialkylaminoalkyl group and $R_{149}$ is a loweralkyl group.

The term "((alkoxy)(alkyl)aminoalkyl)-(alkyl)amino" as used herein refers to $-NR_{150}R_{151}$ wherein $R_{150}$ is $-NR_{152}R_{153}$ appended to a loweralkyl radical wherein $R_{52}$ is an alkoxy group and $R_{153}$ is a loweralkyl group and $R_{151}$ is a loweralkyl group.

The term "((alkoxy)aminoalkyl)(alkyl)amino" as used herein refers to $-NR_{154}R_{155}$ wherein $R_{154}$ is $-NHR_{156}$ appended to a loweralkyl group and wherein $R_{156}$ is an alkoxy group and $R_{155}$ is a loweralkyl group.

The term "loweralkylcarbonyl" as used herein refers to $R_{157}C(O)-$ wherein $R_{157}$ is a loweralkyl group, including, but not limited to acetyl, propionyl and the like.

The terms "alkoxy" and "thioalkoxy" as used herein refer to $R_{158}O-$ and $R_{158}S-$, respectively, wherein $R_{158}$ is a loweralkyl group.

The term "alkenyloxy" as used herein refers to $R_{159}O-$, wherein $R_{159}$ is an alkyl group of 1 to 7 carbon atoms which contains at least one carbon-carbon double bond.

The term "hydroxyalkoxy" as used herein refers to -OH appended to an alkoxy radical.

The term "dihydroxyalkoxy" as used herein refers to an alkoxy radical which is disubstituted with -OH radicals.

The term "arylalkoxy" as used herein refers to an aryl group appended to an alkoxy radical.

The term "alkylaryloxy" as used herein refers to $R_{160}O-$ wherein $R_{160}$ is an alkylaryl group.

The term "phenylalkoxy" as used herein refers to a phenyl group appended to an alkoxy radical, including, but not limited to benzyloxy and the like.

The term "(substituted phenyl)alkoxy" as used herein refers to a substituted phenyl group appended to an alkoxy radical, including, but not limited to 4-chlorobenzyloxy and the like.

The term "naphthylalkoxy" as used herein refers to a naphthyl group appended to an alkoxy radical.

The term "(substituted naphthyl)alkoxy" as used herein refers to a substituted naphthyl group appended to an alkoxy radical.

The term "polyalkoxy" as used herein refers to $R_{161}O-$, wherein $R_{161}$ is a straight or branched chain containing 1-5, $C_m-O-C_{m'}$ linkages where m and m' are independently 1 to 3.

The terms "halo" or "halogen" as used herein refer to Cl, Br, F or I substituents.

The term "haloalkyl" as used herein refers to a loweralkyl radical substituted with a halogen, including, but not limited to fluoromethyl, 2-chloroethyl and the like.

The term "polyhaloalkyl" as used herein refers to a loweralkyl radical substituted with two or more halogens, including, but not limited to trifluoromethyl, 2,2-dichloroethyl and the like.

The term "halobenzyl" as used herein refers to a halo substituent appended to the phenyl ring of a benzyl radical.

The term "halophenyl" as used herein refers to a halo substituent appended to a phenyl radical.

The term "aryl" as used herein refers to an unsubstituted or substituted aromatic ring, substituted with one, two or three substituents selected from loweralkoxy, loweralkyl, amino, loweralkylamino, hydroxy, halogen, mercapto, nitro, thioalkoxy, carboxaldehyde, carboxyl, carboalkoxy and carboxamide, including but not limited to phenyl, halophenyl, loweralkylphenyl, naphthyl and aromatic heterocylics.

The term "substituted phenyl" as used herein refers to a phenyl ring substituted with one, two or three substituents chosen from the group loweralkoxy, loweralkyl, amino, loweralkylamino, hydroxy, halo, mercapto, nitro, thioalkoxy, carboxaldehyde, carboxy, carboalkoxy and carboxamide, including, but not limited to halophenyl, loweralkylphenyl, alkoxyphenyl and the like.

The term "substituted naphthyl" as used herein refers to a naphthyl ring substituted with one, two or three substituents chosen from the group loweralkoxy, loweralkyl, amino, loweralkylamino, hydroxy, halo, mercapto, nitro, thioalkoxy, carboxaldehyde, carboxy, carboalkoxy and carboxamide, including, but not limited to halonaphthyl, alkoxynaphthyl and the like.

The term "alkylaryl" as used herein refers to a loweralkyl group appended to an aryl radical.

The term "heterocylcic group" or "heterocyclic" as used herein refers to any 5-, or 6-membered ring containing from one to three heteroatoms selected from the group consisting of nitrogen, oxygen, and sulfur; wherein the 5-membered ring has 0 to 2 double bonds and the 6-membered ring has 0 to 3 double bonds; wherein the nitrogen and sulfur heteroatoms may optionally be oxidized, wherein the nitrogen heteroatom may optionally be quaternized, and including any bicyclic group in which any of the above heterocyclic rings is fused to a benzene ring. Heterocyclics in which nitrogen is the heteroatom are preferred. Fully saturated heterocyclics are also preferred. Preferred heterocyclics are: pyrryl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl.

Saturated heterocyclics may be unsubstituted, monosubstituted or disubstituted with hydroxy, oxo, amino, alkylamino, dialkylamino, alkoxy, polyalkoxy, loweralkyl, haloalkyl or polyhaloalkyl. Unsaturated heterocyclics may be unsubstituted or monosubstituted with hydroxy, amino, alkylamino, dialkylamino, loweralkyl, haloalkyl or polyhaloalkyl.

The most preferred heterocyclics are as follows:

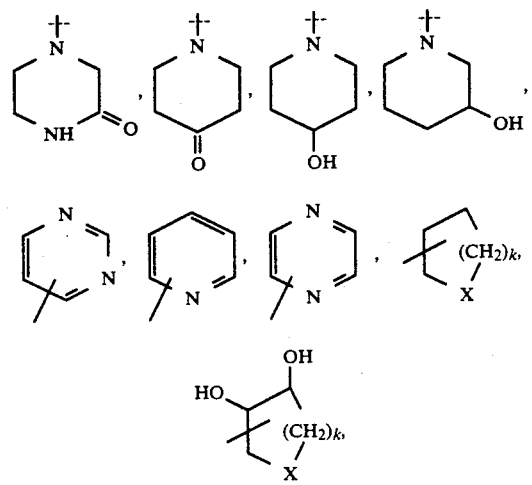

wherein k is 1 or 2 and X is N, NH, O, or S, provided that X is the point of connection only when X is N, wherein Y is NH, N-loweralkyl, O, S, or $SO_2$, or

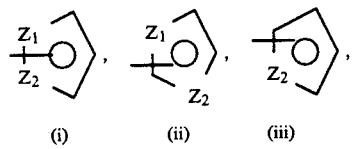

(i)   (ii)   (iii)

wherein the symbols (i), (ii) and (iii) represent 5-membered heterocycles containing one or more heteroatoms and containing 2 double bonds; wherein $Z_1$ is N, O, or S and not the point of connection and $Z_2$ is N when it is the point of connection and NH, O or S when it is not the point of connection.

The term "N-protecting group" or "N-protected" as used herein refers to those groups intended to protect the N-terminus of an amino acid or peptide or to protect an amino group against undesirable reactions during synthetic procedures or to prevent the attack of exopeptidases on the compounds or to increase the solubility of the compounds and includes but is not limited to sulfonyl, acyl, acetyl, pivaloyl, t-butyloxycarbonyl (Boc), carbonylbenzyloxy (Cbz), benzoyl or an L- or D-aminoacyl residue, which may itself be N-protected similarly.

The term "O-protecting group" as used herein refers to a substituent which protects hydroxyl groups against undesirable reactions during synthetic procedures and includes but is not limited to substituted methyl ethers, for example methoxymethyl, benzyloxymethyl, 2-methoxyethoxymethyl, 2-(trimethylsilyl)ethoxymethyl, benzyl and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates.

The terms "lipophilic or aromatic amino acid side chains" as used herein refer to amino acid side chains selected from the group isobutyl, isopropyl, sec-butyl, benzyl, p-methoxybenzyl, imidazole-4-yl-methyl, p hydroxybenzyl, 1- and 2-naphthylmethyl, (pyrazolyl)-methyl, (thiazolyl)methyl, cyclohexylmethyl, (3-indolyl)methyl, $CH_3SCH_2$- and the like. General references to amino acid side chains in both the description and claims herein is to be taken as reference to such, whether naturally occurring in proteins or not, and to both D- and L- forms.

The terms "Ala", "His", "Leu", "Phe", "Tyr", "Cys", "Gly", "Lys", "Sar" and "Pro" as used herein refer to alanine, histidine, leucine, phenylalanine, tyrosine, cysteine, glycine, lysine, sarcosine and proline, respectively. In general, the amino acid abbreviations follow the IUPAC-IUB Joint Commission on Biochemical Nomenclature for amino acids and peptides (Eur. J. Biochem. 1984, 158, 9–31).

The chiral centers of the novel renin inhibiting compounds of the invention may have either the "R" or "S" configuration. The terms "S" and "R" configuration are as defined by the IUPAC 1974 Recommendations for Section E, Fundamental Stereochemistry, Pure Appl. Chem. (1976) 45, 13–30.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfate, glucoheptonate, glycerophosphate, hemislufate, heptonate, hexanoate, fumarate, hydrochloride, hydrobromide, hydroiodide, 2-hydroxy ethanesulfate, lactate, maleate, methanesulfonate, nicotinate, 2-naphthaleneslufonate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

The compounds of the present invention can also be used in the form of esters. Examples of such esters include a hydroxyl substituted compound of the invention which has been acylated with a blocked or unblocked amino acid residue, a phosphate function, or a hemisuccinate residue. The amino acid esters of particular interest are glycine and lysine; however, other amino acid residues can also be used. These esters serve as prodrugs of the compounds of the present invention and serve to increase the solubility of these substances in the gastrointestinal tract. The preparation of the pro-drug esters is carried out by reacting a hydroxyl-substituted compound of the invention with an activated amino acyl, phosphoryl or hemisuccinyl derivative. The resulting product is then deprotected to provide the desired pro drug ester.

The compositions of the invention are administered as topical or systemic pharmaceutical compositions.

The compositions of the invention are preferably administered as topical pharmaceutical compositions suitable for ophthalmic administration, in a pharmaceutically acceptable vehicle such as pharmaceutically acceptable sterile aqueous or nonaqueous solutions, suspensions, emulsions, ointments and solid inserts.

Examples of suitable pharmaceutically acceptable vehicles are water, propylene glycol and other pharmaceutically acceptable alcohols, sesame or peanut oil and other pharmaceutically acceptable vegetable oils, petroleum jelly, water soluble ophthalmologically acceptable non toxic polymers such as methyl cellulose, carboxymethyl cellulose salts, hydroxyethyl cellulose, hydroxypropyl cellulose; acrylates such as polyacrylic acid salts; ethylacrylates; polyacrylamides; natural products such as gelatin, alginates, pectins, tragacanth, karaya, agar, acacia; starch derivatives such as starch acetate, hydroxyethyl starch ethers, hydroxypropyl starch; as well as other synthetic derivatives such as polyvinyl alcohol, polyvinyl pyrrolidone, polyvinyl methyl ether, polyethylene oxide, carbopol and xantham gum; and mixtures of these polymers. Such compositions may also contain adjuvants such as buffering, preserving, wetting, emulsifying, and dispersing agents. Suitable preserving agents include antibacterial agents such as quaternary ammonium compounds, phenylmercuric salts, benzyl alcohol, phenyl ethanol; and antioxidants such as sodium metabisulfite, butylated hydroxyanisole and butylated hydroxytoluene. Suitable buffering agents include borate, acetate, gluconate and phosphate buffers.

The pharmaceutical compositions of the invention may also be in the form of a solid insert. A solid water soluble or water swellable polymer such as dextran, hydroxyloweralkyl dextran, carboxymethyl dextran, hydroxyloweralkyl cellulose, loweralkyl cellulose, carboxymethyl cellulose, polyvinyl alcohol, dextrin, starch, polyvinyl pyrrolidone and polyalkylene glycols may be used as the carrier for the drug.

Dosage levels of the active compound in the compositions may be varied so as to obtain a desired therapeutic response to a particular composition. Generally, the active compound will be administered as an isotonic aqueous solution of from 0.00001 to 1.0 (w/v) percent concentration. More preferably the active compound will be administered as an isotonic aqueous solution of from 0.00001 to 0.1 (w/v) percent concentration. The total daily dose range for a renin inhibitor in a topical ophthalmological composition is 100 micrograms to 10 milligrams per day.

The term "controlling intraocular pressure" as used herein means the regulation, attenuation and modulation of increased intraocular tension. The term also means that the decrease, in the otherwise elevated intraocular pressure, obtained by the methods and compositions of the invention is maintained for a significant period of time as, for example, between consecutive doses of the composition of the invention.

The novel renin inhibiting compounds of the invention may be the only active ingredient for controlling intraocular pressure in the methods and compositions of the invention or may be used in combination with other ingredients which control intraocular pressure such as beta adrenergic antagonist compounds. The term "beta-adrenergic antagonist" as used herein means a compound which by binding to beta-adrenergic plasma membrane receptors reduces or eliminates sympathetic activity or blocks the effects of exogenously administered catecholamines or adrenergic drugs. Examples of beta-adrenergic antagonists are atenolol, metopropol, nadolol, propranolol, timolol, labetalol, betaxolol, carteolol and dilevalol and pharmaceutically acceptable salts thereof. Most preferably the beta-adrenergic antagonist is timolol.

As was previously stated, timolol is currently used for treating glaucoma or reducing and/or controlling intraocular pressure, but it has a number of adverse side effects. Accordingly, administration of a composition comprising a combination of a beta-adrenergic antagonist and a novel renin inhibiting compound of the invention could produce a reduction in intraocular pressure equivalent to that produced by a beta-adrenergic antagonist alone, but at a reduced dose level of the beta-adrenergic antagonist. This will result in a reduced level of the beta-adrenergic antagonist related adverse side effects.

The combination composition is administered as a single dosage form containing both the novel renin inhibitor and the beta-adrenergic antagonist. The beta adrenergic antagonist may comprise from 5 mg to about 125 mg of the composition of the invention. The preferred ranges of the components in the composition of the invention in unit dosage form are:

Renin inhibitor: 1 ng to 0.250 mg
Beta-adrenergic antagonist: 5 mg to 125 mg

When the beta-adrenergic antagonist and the novel renin inhibitor are administered as separate compositions the present invention relates to a kit comprising in two separate containers a pharmaceutically acceptable beta-adrenergic antagonist composition and a pharmaceutically acceptable novel renin inhibitor composition, in a single package. A preferred kit comprises a beta-adrenergic antagonist composition and a topical novel renin inhibitor composition. A most preferred kit comprises a topical ophthalmological beta-adrenergic antagonist composition and a topical ophthalmological novel renin inhibitor composition.

The novel renin inhibiting compounds of the invention may also be administered in combination with an angiotensin converting enzyme inhibiting compound. Examples of angiotensin converting enzyme inhibiting compounds are captopril and enalapril. As was previously mentioned, ACE inhibitors have some undesirable side effects. Accordingly, administration of an ACE inhibitor in combination with a renin inhibitor could produce a reduction in intraocular pressure greater than or equivalent to that of an ACE inhibitor alone, but at a reduced dose level of the ACE inhibitor. This will result in a reduced level of the ACE inhibitor related adverse side effects.

The combination composition is administered as a single dose form containing both the novel renin inhibitor and the angiotensin converting enzyme inhibitor. The ACE inhibitor may comprise from 5 ng to about 50 micrograms of the composition of the invention. The preferred ranges of the components in the composition of the invention in unit dosage form are:

Renin inhibitor: 1 ng to 0.250 mg
ACE inhibitor: 5 ng to 50 micrograms

When the ACE inhibitor and the novel renin inhibitor are administered as separate compositions the present invention relates to a kit comprising in two separate containers a pharmaceutically acceptable ACE inhibitor composition and a pharmaceutically acceptable novel renin inhibitor composition, in a single package. A preferred kit comprises an ACE inhibitor composition and a topical novel renin inhibitor composition. A most preferred kit comprises a topical ophthalmological ACE inhibitor composition and a topical novel renin inhibitor composition.

Dosage levels of the active compounds in the compositions of the invention may be varied so as to obtain a desired therapeutic response depending on the route of administration, severity of the disease and the response of the patient.

Topical, ophthalmic and systemic administration of steroidal antiinflammatory agents can cause an increase in intraocular pressure. The increase in intraocular pressure can be reduced by the administration of a novel renin inhibiting compound of the invention. Steroidal antiinflammatory agents include hydrocortisone, cortisone, prednisone, prednisolone, dexamethasone, methylprednisolone, triamcinolone, betamethasone, alclometasone, flunisolide, beclomethasone, clorocortolone, diflorasone, halcinonide, fluocinonide, fluocinolone, desoximetasone, medrysone, paramethasone, and fluorometholone, and their pharmaceutically acceptable salts and esters. Preferred steroidal antiinflammatory agents are hydrocortisone, prednisolone, dexamethasone, medrysone and fluorometholone and their pharmaceutically acceptable salts and esters. The novel renin inhibitor is administered after use of a steroidal antiinflammatory agent or at the same time, causing reduction and/or control of intraocular pressure.

Various combinations of a topical or oral or injectible dosage form of a steroidal antiinflammatory agent and a topical or oral dosage form of the novel renin inhibitor may be used. A preferred combination comprises a topical steroidal antiinflammatory and a topical novel renin inhibitor. More preferred is a topical ophthalmic dosage form comprising both a steroidal antiinflammatory and a novel renin inhibitor.

When the steroidal antiinflammatory agent and the novel renin inhibitor are administered as separate compositions the present invention relates to a kit comprising in two separate containers a pharmaceutically acceptable steroidal antiinflammatory agent composition and a pharmaceutically acceptable novel renin inhibitor composition, in a single package. A preferred kit comprises a steroidal antiinflammatory composition and a topical novel renin inhibitor composition. A most preferred kit comprises a topical ophthamological steroidal antiinflammatory composition and a topical ophthamological novel renin inhibitor composition.

The combination composition of the invention may contain from about 0.00001 to 1.0 (w/v) percent of the novel renin inhibitor for combined or separate topical administration. More preferably the amount of the novel renin inhibitor is about 0.00001 to 0.1 (w/v) percent of the composition. The amount of the novel renin inhibitor in a unit dosage form for topical administration to the eye is from about 5 ng to about 0.5 mg, preferably from about 5 ng to about 250 micrograms. The dose required will depend on the potency of the particular novel renin inhibitor, the severity of the intraocular pressure increase and the response of the individual patient.

The combination composition of the invention may contain from about 0.05 to 1.5 (w/v) percent of the steroidal antiinflammatory for combined or separate topical administration. The amount of the steroidal antiinflammatory in a unit dosage form for topical administration to the eye is from about 20 micrograms to about 600 micrograms. The dose required will depend on the potency of the particular steroidal antiinflammatory, the severity of the disease and the response of the individual patient.

When the steroidal antiinflammatory agent of the combination therapeutic method of the invention is administered other than ophthalmically, appropriate doses are well known in the art.

The compositions of the invention may include other therapeutic agents in addition to the novel renin inhibitor, and other agents which reduce and/or control intraocular pressure.

The foregoing may be better understood from the following examples which are presented for purposes of illustration and are not intended to limit the scope of the inventive concepts. In the examples that follow (4-morpholinyl)carbonyl-Phe-His amide of 2(S)-amino 1 cyclohexyl (3R),4(S)-dihydroxy-6-methylheptane is referred to as Compound I; H-((beta,beta-dimethyl)-beta-Ala)-(4-OCH3)Phe-His amide of 2(S) amino-1-cyclohexyl-3(R),4(S)-dihydroxy-6-methylheptane diacetic acid salt is referred to as Compound II; (1-(4-hydroxypiperidinyl)carbonyl)-Phe-His amide of 2(S)-amino-1-cyclohexyl-3(R),4(S)-dihydroxy-6-methylheptane is referred to as Compound III; (2R)-2-benzyl-3-((2-methoxyethoxy-methoxyethyl)methyl aminocarbonyl)propionyl-His amide of (2'S,1'R,5S)3-ethyl-5-(1'-hydroxy-2-amino-3-cyclohexylpropyl)-oxazolidin-2-one is referred to as Compound IV; H-((beta,beta-dimethyl)-beta-Ala)-(4-OCH3)Phe-His amide of 2(S)-amino-1-cyclohexyl-3(R),4(S)-dihydroxy-6-methylheptane is referred to as Compound V; Boc-Phe-His amide of 3-amino 4-cyclohexyl-1-cyclohexylmercapto-2-hydroxybutane is referred to as Compound VI; Boc-Phe-Histidinyl-4-amino-3-hydroxy-5-cyclohexylpentanoic acid amide of 2-methylbutylamine is referred to as Compound VII; Boc-Phe-His amide of (3S,4S)-1-(3-isobutylcarbonylamino)-3-hydroxy-4-amino-5-cyclohexylpentane is referred to as Compound VIII; Boc-Phe-His amide of (4S,5S)-N-(3-methylbutyl)-5-amino-6-cyclohexyl-1-hexen-4-ol-2-carboxamide is referred to as Compound IX; Boc-Phe-His amide (4-amino) of (2S,3R,4S)-1,4-diamino-2,3-dihydroxy-5-cyclohexylpentane is referred to as Compound X; Boc-Phe-His amide of (2S,4S,1'R,2'S)-2-(2-amino-7-cyclohexyl-4,5-dihydroxyheptan-2-oic acid sodium salt is referred to as Compound XI; Boc-Phe-His amide of (4S,5R,6S)-6-amino-7-cyclohexyl-4,5-dihydroxy-1-hepten-2-oic acid sodium salt is referred to as Compound XII; 4-Carboxybutyroyl-Phe-Leu amide of 2(S)-amino-1-cyclohexyl-3(R),4(S)-dihydroxy-6-methylheptane is referred to as Compound XIII; and (1(S)-(Ethoxycarbonyl)-ethyl)-Phe-His amide of 2(S)-amino-1-cyclohexyl-3(R),4(S)-dihydroxy-6-methylheptane is referred to as Compound XIV.

EXAMPLE 1 a. N-(2,2-Dimethyl-3-(N,N-dimethylamino)propyl-5-t-butyloxycarbonylamino-6-cyclohexyl-1-hexen-4-ol-2-carboxamide A solution of N-(2,2-dimethyl-3-(N,N-dimethylamino)propyl)-2-methylpropenamide (4.15 mmol) in 25 ml of dry tetrahydrofuran was cooled under an $N_2$ atmosphere to −78° C. and treated dropwise with 3.28 ml (8.5 mmol) of n-butyl-lithium in hexane. The resulting solution was warmed to 0° C. for 20 minutes, recooled to −78° C., and treated with 6.2 mL (6.2 mmol) of chlorotitanium triisopropoxide in hexane. After again warming to 0° C. for 5 minutes, the dark solution was recooled to −78° C. treated with a solution of N-t-butyloxycarbonylcyclohexylalaninal (670 mg, 2.3 mmol) in 5 ml of tetrahydrofuran, stirred for 5 minutes at −78° C., warmed to 0° C. for 20 minutes and quenched with saturated aqueous ammonium chloride. The resulting suspension was treated with ca. 50 ml of ether, stirred until the salts became white, extracted with two 100 ml portions of ether, dried over $MgSO_4$ and concentrated in vacuo to give a ca. 1:1 mixture of (4S,5S) and 4R,5S) products ($R_f$ 0.39, 1:1 methanol/chloroform) in 77% yield which were separated from remaining starting material by preparative thin layer chromatography using 1:1 methanol/chloroform. Further separation of diastereomers was not feasible. Mass spectrum: $M^+ = 453$.

b. N-(2,2-Dimethyl-3-(N,N-dimethylamino)propyl)-5-amino-6-cyclohexyl-1-hexen-4-ol-2-carboxamide dihydrochloride A solution of 45 mg (0.1 mmol) of the resultant compound of Example 1a in ca. 0.1 mL of absolute ethanol was treated with 0.6 mL of 4M HCl in dioxane and allowed to stand at ambient temperature for 1.5 hours. After removal of the solvent in vacuo, the residue was treated twice with 0.5 mL of anhydrous ether followed each time by removal of the solvent in vacuo. The crude diamine dihydrochloride was used without further purification.

c. Boc-Phe-His amide of N-(2,2-dimethyl-3-(N,N-dimethylamino)propyl)-5-amino-6-cyclohexyl-1-hexen-4-ol-2-carboxamide A solution of 3.09 g (6.83 mmol) of the resultant compound of Example 1b, 2.75 g (6.83 mmol) of Boc-Phe-His-OH, and 3.27 g (24.2 mmol) of 1-hydroxy-benzotriazole in 20 mL of dimethylformamide was treated with 750 uL (6.83 mmol) of 4-methylmorpholine, cooled to −23 degrees C., and treated with 1.31 g (6.83 mmol) of 1-ethyl-3-(dimethylaminopropyl)carbodiimide hydrochloride. After being allowed to stir at −23° C. for ca. 2 hours and at ambient temperature for 14 hours, the solution was diluted with ethyl acetate, washed sequentially with aqueous $NaHCO_3$ and $H_2O$, dried ($MgSO_4$) and concentrated in vacuo. Separation by flash column chromatography using 2% methanol/2% isopropylamine in chloroform gave a 58% yield of the desired compound ($R_f$ 0.10, 2% methanol/2% isopropylamine in chloroform) as a mixture of stereoisomers. Mass spectrum. $(M+1)^+ = 738$. Anal. Calcd for $C_{40}H_{63}N_7O_6$: C, 65.10; H, 8.60; N, 13.28. Found: C, 65.97; H, 8.96; N, 13.37.

EXAMPLE 2 a. 2-t Butyloxycarbonylamino-1-cyclohexylbut-3-ene

To a stirred suspension of methyltriphenyl phosphonium bromide (10.97 g, 30.70 mmol) in anhydrous tetrahydrofuran (200 ml) at −78° C. (dry ice/acetone bath) under an argon atmosphere, was added n-butyl lithium (19.8 ml of a 1.55M hexane solution) dropwise over the course of 5 minutes. After 10 minutes, the −78° C. bath was replaced with a 0° C. bath for one half hour, at which time the resulting orange solution was cooled again to −78° C. The solution was then added dropwise by cannula to a stirred −78° C. solution of Boc cyclohexylalaninal (27.91 mmol) in anhydrous tetrahydrofuran (30 ml) over the course of one half hour. The mixture was then allowed to warm to room temperature during a 3 hour period after which water (150 ml) was added. Extraction with hexane (4×100 ml) provided a combined organic phase which was washed with brine (100 ml), dried ($Na_2SO_4$), and concentrated to give crude product. Chromatography with ether/hexane (1/9) provided the pure desired compound. Mass spectrum: $(M+H)^+ = 254$.

b. 3-t-Butyloxycarbonylamino-4-cyclohexyl-1,2-oxobutane

To a stirred solution of the resultant compound of Example 2a (2.0 mmol) in dichloromethane (20 ml) was added m-chloroperbenzoic acid (MCPBA, 1.51 g of 80% MCPBA, 7.0 mmol). After 68 hours the reaction mixture was cooled to 0° C., and 0° C. 10% $Na_2SO_3$ (5 ml) was added with stirring. After 15 minutes, the solid was filtered off and extracted with dichloromethane. The combined organic phase was washed sequentially with 0° C. 10% $Na_2SO_3$ (6 ml), saturate $NaHCO_3$ (2×6 ml), and water (5 ml). Drying ($MgSO_4$), filtering, and evaporating provided crude product which was chromatographed on 50 g of $SiO_2$ (hexane/ether, 3/1) to give the pure desired compound. Mass spectrum: $M^+ = 270$.

c. 3-t-Butyloxycarbonylamino-4-cyclohexyl-1-cyclohexylmercapto-2-hydroxybutane To a stirred solution of the resultant compound of Example 2b (0.87 mmol) in methanol (8.7 ml) was added cyclohexyl mercaptan (102 mg, 0.87 mmol) and triethylamine (88 mg, 0.87 mmol). The resultant solution was refluxed for 2 hours and then evaporated to give a residue which was chromatographed on 15 g of 40 um $SiO_2$ (7/3, hexane/ether) to give the desired compound. Mass spectrum: $M^+ = 385$.

d. 3-t-Butyloxycarbonylamino-4-cyclohexyl-1-cyclohexylsulfonyl-2-hydroxybutane Treating the resultant compound of Example 2c with 2.5 equivalents of 3-chloroperoxybenzoic acid in dichloromethane, gave the desired compound after chromotography. Mass spectrum: $(M+H)^+ = 418$.

e. 3-Amino-4-cyclohexyl-1-cyclohexylsulfonyl-2-hydroxybutane hydrochloride

To a stirred solution of approximately 0.25 mmol of the resultant compound of Example 2d in methanol was added methanolic HCl (10 ml of approximately 0.75M). After 8-12 hours, the solvent was evaporated, and the desired compound was used without further purification.

f. Boc-Phe-His amide of 3-amino-4-cyclohexyl-1-cyclohexylsulfonyl-2-hydroxybutane To a stirred −23° C. solution of Boc-Phe-His-OH (0.38 mmol) in anhydrous dimethylformamide (5 mL) was added a solution of the resultant compound of Example 2f (0.38 mmol) and N methylmorpholine (0.38 mmol) in dimethylformamide. Hydroxybenzotriazole (HOBT) and dicyclohexylcarbodiimide (DCC) were then added sequentially. After 2.5 hours, the mixture was allowed to warm to room temperature for 16 hours, at which time the mixture was filtered and evaporated to a residue which was partitioned between ethyl acetate (20 ml) and saturated $NaHCO_3$ (8 ml). The organic phase was then washed separately with saturated $NaHCO_3$ (8 ml) and brine (8 ml). Drying ($Na_2SO_4$) and evaporating provided a solid which was chromatographed on $SiO_2$ to give the desired compound.

Anal. Calcd. for $C_{36}H_{55}N_5O_7$ (0.5 $H_2O$): C, 60.82; H, 7.94; N, 9.85.

Found: C, 60.70; H, 8.21; N, 9.63.

EXAMPLE 3 a. 4-t-Butyloxycarbonylamino-3-hydroxy-6-methylheptanoic acid ethyl ester

To diisopropylamine (7.7 g, 0.077 mol) in dry tetrahydrofuran (26 mL) cooled to −20 degrees C. under argon was added dropwise n-butyllithium in hexane (1.46M, 52.4 mL, 0.077 mol). The solution was stirred 15 min, the temperature lowered to −78 degrees C. and dry ethyl acetate (6.7 g, 0.077 mol) added dropwise while maintaining the temperature below −75 degrees C. The solution was stirred 10 min and a precooled (−78 degrees C.) tetrahydrofuran solution of Boc-L-leucinal (11 g, 0.051 mol) was added. After 30 min, 2M HCl (40 mL) was added and the mixture was slowly warmed to 10 degrees C. and extracted with ether (3×200 mL). The combined ethereal extract was washed with saturated sodium chloride and dried with magnesium sulfate and filtered. Evaporation of the filtrate in vacuo gave 14 g of crude product which was purified by flash chromatography (20% ethyl acetate in hexane) to give 6 g of desired product.

$H^1$ NMR (300 MHz, $CDCl_3$, ppm). 0.93 (d, 6H), 1.27 (t, 3H), 1.3–1.75 (m, 3H), 1.44 (s, 9H), 2.50 (m, 2H), 3.35 (s, 1H), 3.63 (br m, 1H), 4.03 (br m, 1H), 4.18 (g, 2H), 4.75 (br d, 1H).

b. 4-t-Butyloxycarbonylamino-3-hydroxy-5-cyclohexylpentanoic acid ethyl ester (Boc-ACHPA ethyl ester)

Using the procedure of Example 3a, but replacing Boc-leucinal with Boc-cyclohexylalaninal gave the desired compound in 40% yield. Mass spectrum: $M^+ = 343$.

c. Boc-ACHPA-amide of methioninol 100 mg of Boc-ACHPA was coupled to one equivalent of methioninol using the standard mixed anhydride method (N-methyl morpholine/isobutylchloroformate) to give 100 mg of desired product. Mass spectrum: $m^+ = 432$. (The product was deprotected with 4N HCl to give the corresponding HCl salt).

d. Boc-Phe-His-ACHPA-amide of methioninol

The HCl salt of the resultant compound of Example 3c was coupled to Boc-Phe-His-OH (87 mg) using 1-(3-dimethylaminopropyl)-3-ethylcarbodiimide/1-hydroxybenzotriazole) to give 28 mg of the desired product. Mass spectrum: (M+H)+ =717.

e. Boc-Phe-His-ACHPA-amide of methioninol sulfone

To 20 mg of the resultant product of Example 3d in 2 mL of $CH_2Cl_2$ was added 10 mg of MCPBA. After 5 min, the product was isolated by $SiO_2$ column chromatography to give 7 mg of the desired product. Mass spectrum: (M+H)+ =749.

EXAMPLE 4

Boc-Phe-His amide of (3S,4S)-1-((((dimethylamino)-methyl)carbonyl) amino)-3-hydroxy-4-amino-5-cyclohexylpentane (3S,4S)-1-((((dimethylamino)-methyl)carbonyl)-amino)-3-hydroxy-4-amino-5-cyclohexylpentane is prepared and coupled to Boc-Phe-His-OH according to Rosenberg, J. Med. Chem. 30 1224 (1987) to give the product. Mass spectrum: (M+H)+ =670.4302.

EXAMPLE 5 a. Boc-Phe-Ala Amide of (2S)-Amino-1-cyclohexylbut-3-ene

2(S)-t-Butyloxycarbonylamino-1-cyclohexylbut-3-ene (310 mg. 1.22 mmol) was dissolved in 1M anhydrous HCl in anhydrous methanol (35 mL). After 22 hours, the solvent was evaporated to give 230 mg (99%) of the corresponding amine hydrochloride which was used without further purification.

To a stirred −13° C. solution of Boc-Phe-Ala (408 mg, 1.21 mmol) in dry THF (8 mL) containing N-methylmorpholine (122 mg, 1.21 mmol) was added isobutyl chloroformate (165 mg, 1.21 mmol) dropwise. After 3 minutes, a −13° C. solution of the above amine hydrochloride (230 mg, 1.21 mmol) in 1:1, THF:dimethyl formamide (DMF) (4 mL) containing N-methylmorpholine (122 mg) was added dropwise. The mixture was warmed to room temperature for 2 hours. Evaporation provided a residue which was partitioned between ethyl acetate (30 mL) and 0.1M $H_3PO_4$ (10 mL). The organic phase was washed with brine (10 mL), saturated $NaHCO_3$ (10 mL), and brine (10 mL). Drying, filtering, evaporating, and chromatographing (55 g $SiO_2$; 95:5, $CH_2Cl_2$:$CH_3OH$) gave the desired compound (462 mg, 81%).

b. Boc-Phe-His Amides of 3(S)-Amino-4-cyclohexyl-2(R,S)-hydroxy-1-t-butyldimethylsilyloxybutane 3(S)-t Butyloxycarbonylamino-4-cyclohexyl-1,2(R,S) dihydroxybutane (1.10 g, 3.82 mmol) was treated with anhydrous 1M HCl/$CH_3OH$ (80 mL) for 16 hours at which time evaporation and drying provided the corresponding amine hydrochloride (0.85 g, 100%).

To a suspension of the above hydrochloride salt (344 mg, 1.54 mmol) and imidazole (105 mg) in dichloromethane (15 mL) were added triethylamine (156 mg) and t-butyldimethylsilyl chloride (232 mg). The solvent was evaporated after 31 hours, and the residue was then re-dissolved in anhydrous dimethylformamide (DMF, 15 mL). Boc-Phe-His (619 mg) and 1-hydroxybenzotriazole (HOBT, 312 mg) were then added. After cooling the stirred solution to −23° C., 1,3-dicyclohexylcarbodiimide (DCC, 318 mg) was added. The mixture was warmed to room temperature 3 hours later. After 13 hours the solvent was evaporated in vacuo, and the residue was dissolved in ethyl acetate (40 mL), filtered, washed with saturated $NaHCO_3$ (2×10 mL) and brine (10 mL), and dried ($Na_2SO_4$). Filtration and evaporation provided a residue which was chromatographed on silica gel eluting with dichloromethane/methanol mixtures to give 441 mg (42%) of the desired product. Mass spectrum: (M+H)+ =686.

Anal. calcd. for $C_{36}H_{59}N_5O_6Si$: C, 63.0; H, 8.7; N, 10.2. Found: C, 62.8; H, 9.0; N, 9.9.

c. 2(S)-t-Butyloxycarbonylamino-1-cyclohexyl-6-methyl-hept-3-ene

To a stirred −78° C. solution of Boc-cyclohexylalanine methyl ester (40 g, 140 mmol) in anhydrous toluene (250 mL) was added diisobutylaluminum hydride (130 Mol %, 1.5M solution in toluene, 121.4 mL) at a rate to keep the internal temperature below −60° C. After stirring for an additional 20 minutes at −78° C., the aldehyde solution is used immediately as described below.

To a potassium hydride (35% dispersion in oil, 32.09 g) suspension in a 0° C. mixture of anhydrous THF/DMSO (1000 mL/200 mL) under dry $N_2$ was added 1,1,1,3,3,3-hexamethyldisilazane (209 Mol %, 49.07 g) dropwise. After stirring at 0° C. for 1 hour, the resulting solution was added via cannula to a 0° C. flask containing isopentyltriphenylphosphonium bromide (209 Mol %, 125.66 g). The mixture was stirred vigorously for 1 hour at which time it was cooled to −78° C. The −78° C. aldehyde solution prepared above was then added via cannula. After stirring at −78° C. for 15 minutes, the mixture was allowed to slowly warm to room temperature and then heated to 40° C. for 12 hours. The mixture was then cooled to room temperature and quenched with methanol (7.65 mL) followed by aqueous Rochelle salts (100 mL saturated solution and 500 mL $H_2O$). The mixture was then extracted with ethyl acetate (2×). The combined extracts were washed with water and brine. Drying ($MgSO_4$) and evaporating provided crude alkene which was chromatographed on silica gel (ether/hexane) to give 16.5 g (38%) of the desired compound as an 85:15 mixture of cis:trans isomers. Mp=53°-55° C. Mass spectrum: M+ =309.

Anal. calcd. for $C_{19}H_{35}NO_2$: C, 73.7; H, 11.4; N, 4.5. Found: C, 73.8; H, 11.4; N, 4.5.

d. 2(S)-t-Butyloxycarbonylamino-1-cyclohexyl 3,4-dihydroxy-6-methylheptane: The 3(R)4(S), 3(S)4(S), 3(R)4(R), and 3(S)4(R) Diastereomers To a solution of the resultant compound of Example 5c (8.50, 27.5 mmol) in dry THF (150 mL) were added $OsO_4$ (2.8 mL of a 2.5% solution in t-butanol and N-methylmorpholine N-oxide (9.28 g, 68.7 mmol). After 4 days the mixture was partitioned between ether (200 mL) and brine (100 mL). The aqueous layer was back-extracted with ether (2×100 mL), and the combined organic phase was washed with 10% $Na_2SO_3$, 0.1M $H_3PO_4$, and brine. Drying ($MgSO_4$) and evaporating provided a residue (10.81 g) which was chromatographed on silica gel to elute a 60% yield of the 4 diols in the following order.

3(R),4(S) Mass spectrum: (M+H)+ =344. Anal. calcd. for $C_{19}H_{37}NO_4$: C, 66.4; H, 10.9; N, 4.1. Found: C, 66.4; H, 10.8; N, 3.9.

3(S),4(S) Mass spectrum: (M+H)+ =344. Anal. calcd. for $C_{19}H_{37}NO_4$: C, 66.4; H, 10.9; N, 4.1. Found: C, 66.4; H, 11.1; N, 4.0.

3(R),4(R) Mass spectrum: (M+H)+ =344.

3(R),4(R) Mass spectrum: (M+H)+ =344. Anal. calcd. for C C, 66.4; H, 10.9; N, 4.1. Found: C, 66.0; H, 10.7; N, 4.0.

e. Boc-Phe-His Amide of 2(S)-Amino-1-cyclohexyl-3(R),4(S)-dihydroxy-6-methylheptane The 3(R),4(S) diastereomer of Example 5d was deprotected with HCl/methanol, and the resulting product was coupled to Boc-Phe-His using 1-hydroxybenzotriazole and 1,3-dicyclohexylcarbodiimide according to the procedure of Example 5b. The desired product was obtained in 40-60% yield, Mass spectrum: (M+H)+ =6.8.

Anal calcd. for $C_{34}H_{53}N_5O_6 H_2O$: C, 63.2; H, 8.6; N, 10.8. Found: C, 63.2; H, 8.4; N, 10.5.

f. Boc-His Amide of 2(S)-Amino-1-cyclohexyl-3(R),4(S)-dihydroxy-6-methylheptane The procedure of Example 5e was followed except Boc-Phe-His was replaced with Boc His. Mass spectrum: (M)+ =480.

Anal. calcd. for $C_{25}H_{44}N_4O_5 3/4H_2O$: C, 60.8; H, 9.1; N, 11.3. Found: C, 60.9; H, 9.2; N, 11.0.

g. TBA-CHA-His Amide of 2(S)-Amino-1-cyclohexyl-3(R),4(S)-dihydroxy-6-methylheptane The resultant compound of Example 5f was deprotected with HCl/methanol, and the resulting product was coupled to t-butylacetyl-cyclohexylalanine (TBA-CHA) using the DCC/HOBT method of Example 5b. High resolution mass spectrum calcd. for $C_{35}H_{61}N_5O_5$, (M+H) 632.4751. Found: 632.4759.

h. Cbz-beta-Ala-Phe-His Amide of 2(S)-Amino-1-cyclohexyl-3(R),4(S)-dihydroxy-6-methylheptane Using the procedure of Example 5g, but replacing TBA-CHA with Cbz-beta-Ala-Phe gave the desired compound. Mass spectrum: (M+H)+ =733. Anal. calcd. for $C_{40}H_{56}N_6O_7$: C, 65.5; H, 7.7; N, 11.5. Found: C, 65.2; H, 7.7; N, 11.2.

i. H-beta-Ala-Phe-His Amide of 2(S) Amino-1-cyclohexyl-3(R),4(S)-dihydroxy-6-methylheptane Diacetic Acid Salt The resultant compound of Example 5h (1.00 g, 1.36 mmol) in acetic acid (14 mL) was hydrogenated at 1 atmosphere with 10% Pd/C (0.50 g) for 3 h. Filtration, extraction of the catalyst with acetic acid, and evaporation of the combined acetic acid solutions gave a residue which was dissolved in water (25 mL) and lyophilized to provide 891 mg (91%) of the desired product. Mass spectrum: (M+H)+ =599 (free base). Anal. calcd. for $C_{36}H_{58}N_6O_9 1/2 H_2O$): C, 59.4; H, 8.1; N, 11.5. Found: C, 59.3; H, 8.0; N, 11.2.

j. 3-Benzyloxycarbonylamino-3-methylbutanoic Acid

A solution of 2,2-dimethyl-3-carbomethyoxypropionic acid (LeMaul, Bull. Soc. Chim. Fr., 828 (1965)), 20 g, 0.125 mol, diphenylphosphorylazide (34.3 g, 0.125 mol) and triethylamine was heated in toluene (150 mL) at 100° C. for 2 h. After cooling to 5° C., the toluene solution was washed successively with 0.5M HCl, aqueous NaHCO₃ and brine. Evaporation of the dried solution gave a residue which was chromatographed on silica gel eluting with 60/40 hexane- ether. There was obtained 13 g of methyl 3-isocyanato-3-methylbutanoate as a mobile liquid. A solution of this material in toluene (20 mL) was treated with benzyl alcohol (13 mL) and the resulting mixture heated at reflux for 40 h. Evaporation of the toluene left a residue which was dissolved in methanol (125 mL) and then treated with a solution of NaOH (6.6 g, 0.165 mol) in 22 mL of water. After 5 h, the reaction mixture was partially evaporated, washed with ether and acidified with 6N HCl. Extraction with methylene chloride and evaporation gave 21 g of the desired product. NMR (300 MHz, CDCl₃): 1.42 (s, 6H), 2.78 (s, 2H), 5.08 (s, 2H).

k. CBZ-((beta,beta-di-Me)-beta-Ala)-Phe-OCH₃

A 4.0 g sample of 3-benzyloxycarbonylamino-3-methyl-butanoic acid was coupled to phenylalanine methyl ester hydrochloride (3.43 g) using the mixed anhydride procedure described in Example 5a. Purification of the crude product by flash chromatography eluting with 65/35 ether-hexane gave an 86% yield of product. NMR (300 MHz, CDCl₃): 1.32 (s, 3H), 1.34 (s, 3H), 2.46 (d, 1H), 2.63 (d, 1H), 2.98 (dd, 1H), 3.09 (dd, 1H), 3.70 (s, 3H), 4.86 (dd, 1H), 4.97 (d, 1H), 5.2 (d, 1H), 5.3 (s, 1H), 6.13 (d, 1H).

l. Cbz-(beta,beta-di-Me)-beta-Ala)-Phe-OH

To a 0° C. solution of Cbz-((beta,beta-di-Me)-beta-Ala)-Phe-OMe (1.5 g, 3.63 mmol) in dioxane (15 mL) was added a solution of lithium hydroxide (0.174 g, 4.15 mmol) in water (7.5 mL). After stirring for 1 h at 0°-5° C., the reaction mixture was diluted with cold water and extracted 2× with ether. The aqueous portion was acidified with 6N HCl and extracted with ether. The organic extract was washed with brine and evaporated to give an 87% yield of product as a viscous liquid.

m. Cbz-((beta,beta-di-Me)-beta-Ala)-Phe-His Amide of 2(S)-Amino-1-cyclohexyl-3(R),4(S)-dihydroxy-6-methylheptane Using the procedure of Example 5g, but replacing TBA-CHA with Cbz-((beta,beta-di-Me)-beta-Ala)-Phe- gave the desired compound. Mass spectrum: (M+H)+ =761. Anal. calcd. for $C_{42}H_{60}N_6O_7$ 1/4H₂O: C, 65.5; H, 8.0; N, 10.9. Found: C, 65.5; H, 7.9; N, 11.0.

n. H-((beta,beta-di-Me)-beta-Ala)-Phe-His Amide of 2(S) Amino-1-cyclohexyl-3(R),4(S)-dihydroxy-6-methylheptane Diacetic Acid Salt Using the procedure of Example 5i, but replacing the resultant compound of Example 5h with the resultant compound of Example 5m gave the desired product. Mass spectrum: (M+H)+ =627 (free base). Anal. calcd. for $C_{38}H_{62}N_6O_9.H_2O$: C, 59.7; H, 8.4; N, 11.0. Found: C, 59.5; H, 8.4; N, 11.3.

o. H-((beta,beta-di-Me)-beta-Ala)-(4-OCH₃)Phe-His Amide of 2(S)-Amino-1-cyclohexyl-3(R),4(S)-dihydroxy-6-methylheptane Diacetic Acid Salt Using the procedures of Examples 5m and 5n, but replacing Cbz-((beta,beta-di-Me) beta Ala)-Phe-with Cbz-((beta,beta-di-Me)-beta-Ala)-(OCH₃)Phe gave the desired product. (M+H)+ =657 (free base).

EXAMPLE 6 a. 4(S)-t-Butyloxycarbonylamino-5-cyclohexyl-3(R,S)-hydroxy-1-pentene

To a stirred −78° C. solution of Boc-cyclohexylalanine methyl ester (10.2 g, 35.8 mmol) in dry toluene (60 ml) was added diisobutylaluminum hydride (34 ml of a 1.5M solution in toluene). After 30 min., vinyl magnesium bromide (108 ml of 1M solution in tetrahydrofuran (THF)) was added. After stirring for 15 hours at 0° C., the mixture was carefully quenched with methanol, treated with Rochelle Salts (22 ml of saturated aqueous solution in 140 ml H₂O), and filtered. After extracting the solids 5 times with ethyl acetate, the extracts and filtrate were combined and the organic phase was washed with brine, dried, filtered and evaporated to an oil (10.2 g). Chromatography on silica gel eluting with hexane/ethyl acetate mixtures provided 6.1 g (60%) of the desired product.

Anal calcd. for C₁₆H₂₉NO₃ 1/4H₂O: C, 66.8; H, 10.3; N, 4.9. Found: C, 66.9; H, 10.2; N, 4.7.

b. 4(S)-Cyclohexylmethyl-5(R,S)-vinyl-2-oxazolidinone

The resultant product of Example 6a (2.80 g, 9.88 mmol) in dry dimethylformamide (DMF) (50 ml) was added to a stirred suspension of NaH (593 mg of a 60% dispersion in oil, 14.8 mmol, hexane washed) in dry DMF (50 ml). After 3 hours, the mixture was quenched (750 ml water+100 ml brine) and extracted with ether (5×100 ml). The combined organic phase was washed with brine (3×50 ml), dried (MgSO₄), filtered and evaporated to an oil (2.23 g). The NMR spectrum of the crude product revealed an 82:18 mixture of 5 S:5 R diastereomers. Silica gel chromatography gave 80% recovery of pure diastereomers. 5S:

Anal. calcd. for C₁₂H₁₉NO₂: C, 68.9; H, 9.1; N, 6.7. Found: C, 68.4; H, 9.2; N, 6.5. Mass spectrum (M+1)+ =210. 5 R: Mass spectrum: (M+1)+ =210.

c. (3S,4S)-3-Hydroxy-4-amino-5-cyclohexyl-1-pentene

To the resultant 5S-diasteriomer from Example 6b (2.06 g, 9.84 mmol) in dioxane (180 mL) and water (120 mL) was added barium hydroxide octahydrate (6.24 g, 19.8 mmol). The mixture was refluxed for 18 hours, cooled, filtered, concentrated, taken up in water and extracted with ethyl acetate which was dried over Na₂SO₄ and evaporated to afford 1.64 g (91%) of the desired product, m.p. 59°-61° C.

Anal. calcd. for C₁₁H₂₁NO: C, 72.08; H, 11.55; N, 7.64. Found: C, 71.67; H, 11.68; N, 7.36.

d. (3S,4S)-3-Hydroxy4-tert-butoxycarbonylamino-5-cyclohexyl-1-pentene

To the resultant compound from Example 6c (1.62 g, 8.84 mmol) in methylene chloride (20 mL) was added di-tert-butyldicarbonate (1.93 g, 8.84 mmol). The mixture was stirred for 14 hours, diluted with ethyl acetate, washed sequentially with 0.5M H₃PO₄, saturated NaHCO₃ solution and brine, then dried over Na₂SO₄ and evaporated to afford 2.51 g (100%) of the desired compound.

e. (3S,4S)-3-tert-Butyldimethylsilyloxy-4-tert-butoxycarbonylamino-5-cyclohexyl-1-pentene To the resultant compound from Example 6d (0.264 g, 0.932 mmol) in DMF (4 mL) was added tert-butyldimethylsilyl chloride (0.300 g, 1.99 mmol) and imidazole (0.269 g, 3.95 mmol). The mixture was stirred at room temperature for 12 hours, poured into ethyl acetate and washed sequentially with 0.5M H₃PO₄, saturated NaHCO₃ solution and brine, then dried over Na₂SO₄ and evaporated to afford 0.355 g (96%) of the desired compound. Mass spectrum: (M+H)+ =398.

f. (2RS,3R,4S)-3-tert-Butyldimethylsilyloxy-4-tert-butoxycarbonylamino-5-cyclohexyl-1,2-oxopentane The resultant compound from Example 6e (0.355 g, 0.893 mmol) in methylene chloride (8 mL) was treated with m-chloroperbenzoic acid (0.758 g, 3.51 mmol) and stirred at ambient temperature for 14 hours. The mixture was concentrated, dissolved in ethyl acetate, washed sequentially with cold 10% aqueous Na₂SO₃ then dried over Na₂SO₄ and evaporated to afford 0.374 g (100%) of the desired compound. Mass spectrum: (M+H)+ =404.

g. (2RS,3R,4S)-3-Hydroxy-4 tert-butoxycarbonylamino-5-cyclohexyl-1,2-oxopentane The resultant compound from Example 6f (2.10 g, 5.07 mmol) was treated with 1M tetrabutylammonium fluoride in tetrahydrofuran (10 mL). The mixture was stirred at 0° C. for 1 hour, poured into ethyl acetate, washed with water and brine, then dried over Na₂SO₄ and evaporated. Chromatography on silica gel (0.5% methanol in chloroform) afforded 1.13 g (74%) of the desired compound. Mass spectrum: (M+H)+ =300.

h. (2S,3R,4S)-1-Azido-2,3-dihydroxy-4-tert-butoxycarbonylamino-5-cyclohexylpentane The resultant compound from Example 6g (1.12 g, 3.74 mmol), ammonium chloride (0.374 g, 6.98 mmol) and sodium azide (0.580 g, 8.92 mmol) were refluxed in methanol (25 mL) for 12 hours. The mixture was concentrated, then taken up in ethyl acetate, washed with water and brine, dried over Na₂SO₄ and evaporated. Chromatography on silica gel (20% ether in hexane) afforded 0.461 g (36%) of the desired compound followed by 0.323 g (25%) of the 4-R isomer. M.p. (4S-Diasteriomer): 93°-94° C. Mass spectrum (4R-Diasteriomer): (M+H)+ =343.

i. (2S,3R,4S)-1-Amino-2,3-dihydroxy4-tertbutoxycarbonylamino-5-cyclohexylpentane The resultant compound from Example 6h (107 mg, 0.313 mmol) and 10% palladium on carbon (110 mg) in methanol (10 mL) were stirred under a hydrogen atmosphere for 18 hours. The mixture was filtered and evaporated to afford 94.6 mg (96%) of the desired compound. Mass spectrum: (M+H)+ =317.

j. (2S,3R,4S)-1-(3-Methylbutylcarbonylamino)-2,3-dihydroxy-4-tert-butyloxycarbonylamino-5-cyclohexylpentane To the resultant compound from Example 6i (94.6 mg, 0.299 mmol) in methylene chloride (5 mL) at 0° C. was added 4-methylpentanoyl chloride (52 ul, 0.37 mmol) and triethylamine (71 ul, 0.51 mmol). The mixture was stirred at 0° C. for 90 min, diluted with ethyl acetate, washed sequentially with 0.5M H solution, 2M NaOH solution and brine, and then dried over $Na_2SO_4$ and evaporated to afford 0.118 g (95%) of the desired compound, m.p. 179°–183° C.

Exact mass calcd. for $C_{22}H_{43}N_2O_5$: 415.3172. Found: 415.3166.

k. Boc-Phe-His Amide of (2S,3R,4S)-1-(3-Methylbutylcarbonylamino)-2,3-dihydroxy-4-amino-5-cyclohexylpentane The resultant compound from Example 6j (57.0 mg, 0.138 mmol) was stirred in 4M HCl/dioxane (1.5 mL) for 1 hour and evaporated. The residue was dissolved in dimethylformamide (0.9 mL) and treated with N-methyl-morpholine (33 ul, 0.30 mmol).

To Boc-Phe-His-OH (59.1 mg, 0.147 mmol) and 1-hydroxybenzotriazole (58.0 mg, 0.429 mmol) in dimethylformamide (0.8 mL) at −23° C. was added 1-(3-dimethylaminopropyl)-3-ethylcarbodiimide hydrochloride (EDAC, 28.7 mg, 0.150 mmol). After stirring at −23° C. for 1 hour, the amine solution was added and the reaction was stirred at −23° C. for 2 hours then at room temperature for 12 hours. The mixture was poured into saturated $NaHCO_3$ solution and extracted with ethyl acetate which was washed with water and brine, then dried over $Na_2SO_4$ and evaporated. Chromatography of the residue on silica gel (3% methanol in chloroform) afforded 21.5 mg (22%) of the desired compound, m.p. 194°–196° C.

l. Boc-His Amide of (2S,3R,4S)-1-Azido-2,3-dihydroxy-4-amino-5-cyclohexylpentane Using the procedure of Example 6k with the resultant compound from Example 6h and using Boc-His-OH rather than Boc-Phe-His-OH afforded the desired compound. Mass spectrum: $(M+H)^+ = 657$.

m. Isobutyryl(phenylmethyl)alanine-His Amide of (2S,3R,4S) 1-Azido 2,3-dihydroxy-4-amino-5-cyclohexylpentane Using the procedure of Example 6k with the resultant compound from Example 6l and using isobutyryl(phenylmethyl)alanine rather than Boc-Phe-His-OH gave the desired compound.

Exact mass calcd. for $C_{31}H_{47}N_8O_5 (M+H)$: 611.3669. Found: 611.3649.

EXAMPLE 7 a. Boc-Valine-(2S)-Methylbutylamide

A mixture of Boc Val OH (2.6 g, 12 mmol) and S-2-methylbutylamine (0.86 g. 9.86 mmol) in 25 ml anhydrous DMF was added with 1-hydroxy-benzotriazole monohydrate (2 g, 14.8 mmol) and dicyclohexylcarbodiimide (2 g, 9.7 mmol) at 0° C. The mixture was stirred at 0°–5° C. for 3 h and then at room temperature for 12 h. DMF was evaporated off under reduced pressure. The resulting residue was partitioned between $CHCl_3$ and $NaHCO_3$ solution. The organic layer was separated, dried ($MgSO_4$) and evaporated to crude product which was recrystallized from EtOAc to afford 1.8 g (63.8%) of desired product.

mp, 153°–155° C., m/e $(M+H)^+$, 287; $H^1NMR$ ($CDCl_3$) PPM, 0.8–1 (m, 12H), 1.45 (s,9H), 3.15 (m,2H), 3.8 (m,1H).

b. N-((2S)-2-Amino-3-cyclohexyl)-propyl valine-(2S)-methylbutylamide dihydrochloride or cyclohexylala-reduced valine-(2S)-methylbutylamide, dihydrochloride Boc-Valine-(2S)-Methylbutylamide (1.3 g, 4.54 mmol was stirred for 1 h at ambient temperature in 4M HCl/dioxane (30 ml). The mixture was evaporated with ether chasers and the residue was taken up into 2-propanol (25 ml). To this solution at 0° C. were added anhydrous NaOAc (0.755 g, 9.1 mmol) and then Boc-cyclohexylalanal (Roger, J. Med. Chem., 28, 1779 (1985)) (1.17 g, 4.6 mmol). The mixture was stirred at 0°–5° C. for ¼ h and at ambient temperature for 16 h. The mixture was filtered, and the filtrate was evaporated to residue. The crude product was partitioned between $CHCl_3$ and $NaHCO_3$ solution. The organic layer was separated, washed with $H_2O$, dried and evaporated to solid which was recrystallized from EtOAc to afford analytically pure product. After deprotection (as above) the desired product gave 580 mg (32.2% overall yield).

mp, 247°–250° C.; m/e $(M+H)^+$, 326; $H^1NMR$ ($CDCl_3$) PPM, 0.9 (m,9H), 1.1 (d,3H), 1.2–1.5 (m,16H), 4.4 (m,1H).

c. Boc Phenylalanyl-histidyl cyclohexylala-reduced valine-(2S)methylbutylamide To cyclohexylala-reduced valine-(2S)-methylbutylamide dihydrochloride (38.8 mg, 0.097 mmol) in 4 ml of anhydrous DMF at 5° C. was added triethylamine (19.7 mg, 1.95 mmol). The mixture was stirred at 0°–5° C. for ¼ h, Boc-Phe-His-OH (48 mg, 0.12 mmol), 1-hydroxybenzotriazole monohydrate (20 mg, 0.15 mmol) and then dicyclohexylcarbodiimide (20 mg, 0.1 mmol) were added. The mixture was stirred at the same temperature for 2 h and at ambient temperature for 16 h. DMF was evaporated off under reduced pressure and the resulting residue was partitioned between $CHCl_3$ and $NaHCO_3$ solution. The organic layer was separated, washed with $H_2O$, dried and evaporated to crude product which was chromatographed on silica gel eluting with 10% $CH_3OH$ in $CHCL_3$ to afford 28 mg (40.5%) of purified product.

mp, 88°–90° C.; m/e $(M+H^+, 710; H^1NMR (CDCl_3)$ PPM, 0.9 (m,9H), 1.1 (d,3H), 1.4 (s,9H), 2.1 (m,2H), 2.5 (m,2H), 2.89 (m,2H), 3.15 (m,2H), 4.1 (m,1H), 4.2 (m,1H), 4.6 (m,1H), 6.85 (s,1H), 7.3 (m,5H), 7.5 (s,1H).

EXAMPLE 8 a. 4(S)-t-Butyloxycarbonylamino-5-cyclohexyl-3(R,S)-hydroxyl-1-pentene

To a stirred −78° C. solution of Boc-cyclohexylalanine methyl ester (10.2 g, 35.8 mmol) in dry toluene (60 ml) was added diisobutylaluminum hydride (34 ml of a 1.5M solution in tetrahydrofuran (THF). After stirring for 15 h at 0° C., the mixture was carefully quenched with methanol, treated with Rochelle salts (22 ml of saturated aqueous solution in 140 ml $H_2O$), and extracts and filtrate were combined and the organic phase was washed with brine, dried, filtered and evaporated to an oil (10.2 g). Chromatography on silica gel eluting with hexane/ethyl acetate mixtures provided 6.1 g (60%) of the desired product.

Anal. calcd. for $C_{16}H_{29}NO_3 \cdot \frac{1}{4}H_2O$: C, 66.8; H, 10.3; N, 4.9.

Found: C, 66.9; H, 10.2; N, 4.7.

b. 4(S)-Cyclohexylmethyl-5(R,S)-vinyl-2-oxazolidinone

The resultant product of Example 8a (2.80 g, 9.88 mmol) in dry dimethylformamide (DMF) (50 ml) was added to a stirred suspension of NaH (593 mg of a 60% dispersion in oil, 14.8 mmol, hexane washed) in dry DMF (50 ml). After 3 h, the mixture was quenched (750 ml water+100 ml brine) and extracted with ether (5×100 ml). The combined organic phase was washed with brine (3×50 ml), dried (MgSO4), filtered and evaporated to an oil (2.23 g). The NMR spectrum of the crude product revealed an 82:18 mixture of 5S:5R diastereomers. Silica gel chromatography gave 80% recovery of pure diastereomers. 5S:

Anal. calcd. for $C_{12}H_{19}NO_2$: C, 68.9; H, 9.1; N, 6.7.

Found: C, 68.4; H, 9.2; N, 6.5. Mass spectrum: $(M+1)^+ = 210$. 5R: Mass spectrum: $(M+1)^+ = 210$.

c. (3S,4S)-3-Hydroxy-4-amino-5-cyclohexyl-1-pentene

To the resultant 5S -diasteriomer from Example 8b (2.06 g, 9.84 mmol) in dioxane (180 ml) and water (120 ml) was added barium hydroxide octahydrate (6.24 g, 19.8 mmol). The mixture was refluxed for 18 h, cooled, filtered, concentrated, taken up in water and extracted with ethyl acetate which was dried over Na2SO4 and evaporated to afford 1.64 g (91%) of the desired product, m.p.: 59°-61° C.

Anal. calcd for $C_{11}H_{21}NO$: C, 72.08; H, 11.55; N, 7.64.

Found: C, 71.67; H, 11.68; N, 7.26.

d. (3S,4S)-3-Hydroxy-4-tert-butyloxycarbonylamino-5-cyclohexyl-1-pentene

To the resultant compound from Example 8c (1.62 g, 8.84 mmol) in methylene chloride (20 ml) was added di-tert-butyldicarbonate (1.93 g, 8.84 mmol). The mixture was stirred for 14 h, diluted with ethyl acetate, washed sequentially with 0.5M H3PO4, saturated NaHCO3 solution and brine, then dried over Na2SO4 and evaporated to afford 2.51 g (100%) of the desired compound.

e. (3S,4S)-3-Methoxyethoxymethoxy-4-tertbutyloxycarbonylamino-5-cyclohexyl-1-pentene To the resultant compound from Example 8d (2.51 g, 8.84 mmol) in methylene chloride (20 ml) was added diisopropyl ethylamine (4.60 ml, 26.4 mmol) and methoxyethoxy chloromethane (3.00 ml, 26.3 mmol). After stirring at room temperature for 24 h the mixture was concentrated, diluted with ethyl acetate, washed with 0.5M H3PO4, saturated NaHCO3 solution, then brine, dried over Na2SO4, and evaporated. Chromatography on silica gel with ethyl acetate/hexane mixtures afforded 2.63 g (80%) of the desired product as an oil. EI-MS: $M^+ = 371$.

f. (2RS,3R,4S)-3-Methoxyethoxymethoxy-4-tertbutyloxycarbonylamino -5-cyclohexyl-1,2-oxopentane To the resultant compound from Example 8e (5.41 g, 14.56 mmol) in methylene chloride (50 ml) was added chloroperbenzoic acid (6.28 g). After stirring at room temperature for 60 h the mixture was concentrated, diluted with ethyl acetate, washed with cold 1:1 15% aqueous Na2SO3 solution/saturated NaHCO3 solution (2×200 ml), saturated NaHCO solution (3×100 ml) then brine (1×100 ml), dried over Na2SO4, and evaporated to afford 4.57 g (81%) product as an oil. EI-MS: $M^+ = 387$.

g. (2'S,1'R,5S)-3-Ethyl-5-(1'-methoxyethoxymethoxy-2'-tert-butyloxycarbonylamino-3'-cyclohexylpropyl)oxazolidin-2-one To the resultant compound from Example 8f (310 mg, 0.80 mmol) in isopropanol (5 ml) was added ethyl amine (200 mg, 4 mmol). The mixture was heated at 70° C. for 48 h, evaporated and dissolved in methylene chloride (5 ml). To this solution was added triethylamine (0.34 ml, 2.4 mmol) and phosgene in toluene (0.1 ml, 1.2 mmol, 12.5% solution). After 2 h the mixture was diluted with ethyl acetate, washed with 0.5M H3PO4, saturated NaHCO3 solution then brine, dried over Na2SO4 and evaporated. Chromatography of the residue on silica gel with 1:1 ethyl acetate/hexane provided 14.3 mg (4%) of the 5R isomer followed by 63.0 mg (17%) of the desired 5S isomer, both as oils.

5S-Isomer: $^1$H-NMR (CDCl3, TMS) 4.83 (d,1H), 4.80 (d,1H), 4.58 (m,1H), 3.49 (s,3H), 1.43 (s,9H), 1.15 (t,3H).

5R-Isomer: MS $(M+H)^+ = 459$.

h. N-Benzyloxycarbonyl-2-aminoethanol

To ethanolamine (9.0 ml, 149 mmol) in methylene chloride (100 ml) at 0° C. was added benzyl chloroformate (10.0 ml, 70 mmol). The mixture was stirred at 0° C. for 30 min, then at room temperature for 1 h, poured into ethyl acetate, washed with 2M HCl, saturated NaHCO3 solution, and brine, then dried over Na2SO4 and evaporated to provide 12.91 g (94%) of the desired compound as a white solid. $^1$H-NMR (CDCl3,TMS) 7.47 (m,5H), 5.11 (s,2H), 3.73 (m,2H), 3.38 (m,2H).

i. 1-Methoxymethoxy-2-benzyloxycarbonylaminoethane

To the resultant compound from Example 8h (12.91 g, 66.1 mmol) in methylene chloride (100 ml) was added diisopropylethylamine (24.0 ml, 138 mmol) and chloromethylmethylether (10.0 ml, 132 mmol). After 4 h the mixture was evaporated, dissolved in ethyl acetate, washed with 0.5M H3PO4, saturated NaHCO3 solution, and brine, then dried over Na2SO4, and evaporated to afford 15.27 g (97%) of the desired product as an oil. $^1$H-NMR (CDCl3, TMS) 7.47 (m,5H), 5.12 (s,2H), 4.62 (s,2H), 3.62 (m,2H), 3.42 (m,2H), 3.35 (s,3H).

j. 1-Methoxymethoxy-2-aminoethane

The resultant compound from Example 8i (7.60 g, 31.2 mmol) and 10% palladium on carbon (3 g) in methanol (60 ml) were stirred under a hydrogen atmosphere for 24 h. The mixture was filtered, evaporated and distilled to afford 2.02 g (60%) of the desired product as an oil. b.p. 60°-70° C., 45 mm; $^1$H-NMR (CDCl3, TMS) 4.65 (s,2H), 3,56 (t,3H), 3.37 (s,3H), 2.88 (t,3H).

k. Boc-His Amide of (2'S,1'R,5S)-3-Ethyl-5-(1'-hydroxy-2'-amino-3'-cyclohexylpropyl)-oxazolidin-2-one The resultant compound from Example 8g (2.23 g, 4.87 mmol) was stirred for 1 h in 4.5M ethanolic HCl (15 ml). The solvent was evaporated with ether and toluene chasers and the residue was dissolved in dimethylformamide (25 ml) and treated with Boc-His-OH (1.37 g, 5.36 mmol) and 1-hydroxybenzotriazole (1.98 g, 14.6 mmol). The mixture was cooled to $-23°$ C. and N-methylmorpholine (600 ul, 5.46 mmol) was added followed by 1-(3-dimethylaminopropyl)-3-ethylcarbodiimide (1.05 g, 5.46 mmol). The mixture was stirred at $-23°$ C. for 2 h and at room temperature 16 h, and then was poured into saturated $NaHCO_3$ solution and extracted into ethyl acetate which was washed with water and brine, then dried over $Na_2SO_4$ and evaporated. Chromatography of the residue on silica gel with 4% methanol in chloroform provided 1.785 g (72%) of the desired product as a white solid. $^1H$-NMR ($CDCl_3$, TMS) 7.58 (s,1H), 6.89 (s,1H). 6.26 (m,1H), 4.39 (m,1H), 4.40 (m,1H), 3.30 (m,2H). 3.16 (dd,1H). 3.01 (dd,1H), 1.47 (s,9H), 1.17 (t,3H).

l. Boc-Leu Amide of (2'S,1'R,5S)-3-Ethyl-5-(1'-hydroxy-2'-amino-3-cyclohexylpropyl)-oxazolidin-2-one The resultant compound from Example 8g (131 mg, 0.285 mmol) was stirred for 1 h in 4.5M ethanolic HCl (2 ml). The solvent was evaporated with ether and toluene chasers and the residue was taken up in methylene chloride (4 ml) and treated with N-methylmorpholine (65 ul, 0.59 mmol). To Boc-Leu-OH (81.6 mg, 0.327 mmol) in methylene chloride (2 ml) at $-10°$ C. was added N methylmorpholine (40 ul, 0.34 mmol) then isobutyl chloroformate (45 ul, 0.34 mmol). After 3 min the amine solution was added, the reaction was stirred at $-10°$ C. for 15 min and then at room temperature for 2 h. The mixture was poured into ethyl acetate which was washed with 0.5M $H_3PO_4$, saturated $NaHCO_3$ solution, and brine, then dried over $Na_2SO_4$ and evaporated to provide 140 mg (100%) of the desired product as a solid. $^1H$-NMR ($CDCl_3$, TMS) 6.72 (d,1H), 4.75 (d,1H), 4.30 (m,1H), 4.08 (m,1H), 3.80 (m,1H), 3.61 (m,3H), 3.31 (m,2H), 1.45 (s,9H), 1.17 (t,3H), 0.97 (t,6H).

m. (4R)-3-(3-Phenylpropionyl)-4-(2-propyl)-oxazolidine-2-one

To a stirred solution of 4-(2-propyl)-oxazolidine-2-one in anhydrous tetrahydrofuran (250 ml) under a nitrogen atmosphere at $-78°$ C. were added in a dropwise fashion a solution of n-butyllithium in hexane (50 ml, 77.4 mmol) over 5 to 10 min. After stirring an additional 20 min at $-78°$ C. 3-phenylpropionyl chloride (12.7 ml, 85.2 mmol) was added neat. The reaction was warmed to room temperature and stirred 1 to 2 h. The reaction was quenched by adding 100 ml of saturated aqueous ammonium chloride and the volatiles removed by rotary evaporation. The resulting aqueous residue was extracted three times with ether and the combined organic phases were washed with brine, dried ($Na_2SO_4$), filtered and concentrated in vacuo. Recrystallization from hexanes/ethyl acetate provided the title compound (16.6 g, 82%). m.p. =86.5° to 87.5° C. Mass spectrum: $(M+NH_4)^+=279$, $(M+H)^+=262$.

n. (4R)-3-((2R)-3-t-butyloxycarbonyl-2-benzylpropionyl)-4-(2-propyl)-oxazolidine-2-one To a stirred solution of the product resulting from Example 8m (2.28 g, 8.72 mmol), in anhydrous tetrahydrofuran (30 ml) under a nitrogen atmosphere at $-78°$ C. was added a solution of sodium hexamethyldisilylamide (9.6 ml, 9.59 mmol) in tetrahydrofuran. After stirring for 30 min at $-78°$ C., t-butyl bromoacetate (2.21 g, 11.34 mmol) was added in anhydrous tetrahydrofuran and the resulting solution stirred 1 h at $-78°$ C. The reaction was quenched by adding 20 ml of saturated aqueous ammonium chloride and partitioned between water and ether. The aqueous layer was drawn off and extracted with ether. The combined organic phases were washed with 10% aqueous HCL, saturated aqueous $NaHCO_3$, and brine, dried ($Na_2SO_4$), filtered, and concentrated in vacuo. Recrystallization from acetone/hexanes provided the desired purified product (2.59 g, 79%). m.p.=167°-168° C. Mass spectrum: $(M+NH_4)^+=393$, $(M+H)^+=376$.

o. Benzyl-(2R)-3-t-butyloxycarbonyl-2-benzylpropionate

To a stirred solution of dry benzyl alcohol (0.55 ml, 5.33 mmol) in anhydrous tetrahydrofuran (18 ml) under a nitrogen atmosphere at 0° C. was added a hexane solution of N-butyllithium (2.58 ml; 4.00 mmol). To this solution was added the product from Example 8n in anhydrous tetrahydrofuran (10 ml). After stirring 1 h at 0° C. the reaction was quenched by adding excess saturated aqueous ammonium chloride. The volatiles were removed by rotary evaporation and the resulting aqueous reside extracted two times with ether. The combined organic layers were washed with brine, dried ($Na_2SO_4$), filtered, and concentrated in vacuo provided an oil which was purified by chromatography on $SiO_2$ (15% ethyl acetate/hexanes) to provide the desired product (0.89 g, 94%) as a colorless oil. Mass spectrum: $(M)^+=354$.

p. Benzyl-(2R)-3-carboxy-2-benzylpropionate

The product from Example 8o (0.52 g, 1.47 mmol) was dissolved in a 1:1 (v:v) solution (6 ml) of trifluoroacetic acid and dichloromethane and stirred at room temperature for 1 h. The volatiles were removed in vacuo to provide the title compound (0.437 g, 100%) as an oil which crystallized on standing. The unpurified material was of sufficient purity to employ in subsequent steps. Mass spectrum: $(M)^+=298$.

q. Benzyl-(2R)-2-benzyl-3-(N-morpholinocarbamoyl)-propionate

The product from Example 8p (0.438 g, 1.47 mmol), diphenylphosphoryl azide (317 ul, 1.47 mmol), and triethylamine (2.05 ul, 1.47 mmol) in dry benzene (6 ml) were refluxed for 3 to 5 h to provide a solution of the derived isocyanate which was cooled to 0° C. and treated with morpholine (141 ul, 1.62 ml). The cooling bath was removed and the reaction stirred for 1 h. The reaction mixture was poured into 10% aqueous HCl and extracted two times with ether. The combined organic layers were washed successively with saturated aqueous $NaHCO_3$ and brine, dried ($Na_2SO_4$), filtered and concentrated in vacuo to provide the unpurified product. The desired product (0.403 g, 72%) was obtained in pure form after chromatography on SiO$_2$ (3% methanol/chloroform) as a thick oil which formed an amorphous solid on standing. Mass spectrum: (M)$^+$ =382. NMR (300 MHz, CDCl$_3$, ppm, TMS as internal standard) 7.12–7.40 (m,10H), 5.18 (AB; J-12.6 Hz; 2H), 4.8 (dd; J=5.7 Hz; 1H), 3.59 (d,d; J=6.0, 6.0 Hz; 4H), 3.55 (d,d,d; J=3.0, 6.0, 14.4 Hz; 1H), 3.37 (d,d,d; J=5.4, 8.4, 14.4 Hz; 1H), 3.13 (d,d; J=6.0, 6.0 Hz; 4H), 2.8–3.10 (m,3H).

r. (2R)-2-Benzyl-3-(morpholinocarbamoyl)-propionic Acid

The product from Example 8q (0.315 g, 0.86 mmol) was dissolved in ethyl acetate (5 ml) and syringed into a flask charged with 10% Pd/C (0.3 g). The resulting suspension was exposed to 1 atm of gaseous hydrogen for 2 to 4 h. The catalyst was removed by filtration through a celite pad. The filtrate was evaporated in vacuo to provide the desired compound (0.21 g, 88%) as a cream colored foam which was employed without further purification. Mass spectrum: (M+H)$^+$ =278.

s. 2-N-methyl-benzyloxycarbonylaminoethanol

Using the procedure of Example 8h and replacing ethanolamine with N-methylethanolamine provided the desired product. $^1$H-NMR (CDCl$_3$, TMS) 7.36 (m,5H), 3.78 (m,2H), 3.47 (m,2H), 5.14 (s,2H), 3.01 (s,3H).

t. 1-Methoxyethoxymethoxy-2-(N-methylbenzyloxycarbonylamino)ethane

Using the procedure of Example 8i with the resultant compound from Example 8s and replacing chloromethyl methyl ether with 2-methoxyethoxy methylchloride gave the desired compound, b.p. 150°–170° C. (0.3 mm).

u. 1-Methylamino-2-methoxyethoxymethoxyethane

Using the procedure of Example 8j with the resultant compound from Example 8t gave the desired product, b.p. 130°–140° C. (45 mm).

v. Benzyl (2R)-2-Benzyl-3-(N-Methyl-N-2-methoxyethoxymethoxyethylaminocarbonyl)propionate Using the procedure of Example 8l with the resultant compounds from Example 8p and Example 8u gave the desired product.
Anal. calcd. for C$_{25}$H$_{33}$NO$_6$: C, 67.70; H, 7.50; N, 3.16.
Found: C, 67.79; H, 7.12; N, 3.15.

w. 2(R)-2-Benzyl-3-(N-Methyl-N-2-methoxyethoxymethoxyethylaminocarbonyl) propionic Acid Using the procedure of Example 8r with the resultant compound from Example 8v gave the desired product. $^1$H-NMR (CDCl,TMS) 7.27 (m,5H), 4.70, 4.55 (m, total 2H), 3.40,3.41 (s, total 3H), 2.97, 2.93 (s, total 3H).

x. (2R)-2-Benzyl-3-((2-methoxyethoxymethoxyethyl) methylaminocarbonyl)propionyl-His Amide of (2'S,1'R,5S)3-Ethyl-5-(1'-hydroxy-2'-amino-3'-cyclohexylpropyl) oxazolidin-2-one Using the procedure of Example 8k with the resultant compound from Example 8k and replacing Boc-His-OH with the resultant compound from Example 8w provided the desired compound, melting point 57°–60° C.

Anal calcd. for c$_{38}$H$_{58}$N$_6$O$_9$.H$_2$O: C, 59.98; H, 7.95; N, 11.04.
Found: C, 60.17; H, 7.94; N, 10.79.

EXAMPLE 9 a. ((4-Morpholinyl)carbonyl)-Phe-methyl ester.

A suspension of L-phenylalanine methyl ester hydrochloride (6 g) in toluene (125 mL) was heated to 100 degrees C. while phosgene gas was bubbled into the reaction mixture. After approximately 1½ to 2 h, the mixture became homogeneous. The passage of phosgene was continued for an additional 15 min, keeping the temperature at 90°–100 degrees C. The toluene was then evaporated and the residue chased several times with benzene. A 6.5 g (0.03167 mol) sample of alpha-isocyanato -L-phenylalanine methyl ester was dissolved in 50 mL of methylene chloride and cooled to 0 degrees C. Morpholine (2.76 mL, 0.03167 mol) dissolved in 5 mL of methylene chloride was added dropwise. After 10 min at 0°–5 degrees C., the reaction mixture was distributed between 0.5N HCl and methylene chloride. The organic layer was washed with aqueous NaHCO$_3$ and dried over MgSO$_4$. Evaporation of the solvent gave 7 g of product after trituration with hexane, mp 90–91 degrees C.

b. (4-Morpholinyl)carbonyl)-Phe

Using the procedure of Example 5l gave the title compound in 89% yield.

c. ((4-Morpholinyl)carbonyl)-Phe-His Amide of 2(S)-Amino-1-cyclohexyl-3(R),4(S)-dihydroxy-6-methylheptane.

Using the procedure of Example 5g, but replacing TBA-CHA with ((4-morpholinyl)carbonyl)-Phe, gave the desired compound. Mass spectrum: (M+H)$^+$ =641.

EXAMPLE 10

(1-(4-Hydroxypiperidinyl)carbonyl) Phe-His Amide of 2(S)-Amino-1-cyclohexyl-3(R),4(S)-dihydroxy-6-methylheptane.

Using the procedures of Example 9, but replacing morpholine with4-hydroxypiperidine gave the desired compound in 56% yield.

EXAMPLE 11 a. 2(S)-t-Butyloxycarbonylamino-1-cyclohexylbut-3-ene

A 0° C. solution of potassium hexamethyl disilazide (22.9 mmol in 115 mL of 5:1, tetrahydrofuran (THF): dimethyl sulfoxide (DMSO) was added dropwise to triphenylmethylphosphonium iodide (24.81 mmol). After stirring at 0° C. for 1 hour, the solution was cooled to −78° C. and a solution of Boc-cyclohexylalaninal [4.90 g, 19.08 mmol, prepared by Swern oxidation (Mancuso, A. J.; Huang, S.-L.; and Swern, D., *J. Org. Chem.* 1978, 43, 2480) of Boc-cyclohexylalaninol] in dry THF (95 mL) was added. After stirring at -78° C. for 1 hour, the mixture was allowed to warm to room temperature. The reaction mixture was quenched with aqueous ammonium chloride and extracted with ether (2×300 mL). The combined organic phase was washed with 10% HCl (200 mL), saturated NaHSO$_3$ (2×200 mL), H$_2$O (2×200 mL), saturated NaHCO$_3$ (2×200 mL), and brine (200 mL), dried (MgSO$_4$), filtered, and evaporated. The residue was purified by chromatography (40 m SiO$_2$; ether:hexane, 15:85) to give the desired compound in 60% yield. Mass spectrum: (M+H)$^+$=254.

b. Boc-Phe-Ala Amide of (2S)-Amino-1-cyclohexylbut-3-ene

The resultant compound of Example 11a (310 mg, 1.22 mmol) was dissolved in 1M anhydrous HCl in anhydrous methanol (35 mL). After 22 hours, the solvent was evaporated to give 230 mg (99%) of the corresponding amine hydrochloride which was used without further purification.

To a stirred −13° C. solution of Boc-Phe-Ala (408 mg, 1.21 mmol) in dry THF (8 mL) containing N-methylmorpholine (122 mg, 1.21 mmol) was added isobutyl chloroformate (165 mg, 1.21 mmol) dropwise. After 3 minutes, a −13° C. solution of the above amine hydrochloride (230 mg, 1.21 mmol) in 1:1, THF:dimethyl formamide (DMF) (4 mL) containing N-methylmorpholine (122 mg) was added dropwise. The mixture was warmed to room temperature for 2 hours. Evaporation provided a residue which was partitioned between ethyl acetate (30 mL) and 0.1M H$_3$PO$_4$ (10 mL). The organic phase was washed with brine (10 mL), saturated NaHCO$_3$ (10 mL), and brine (10 mL). Drying, filtering, evaporating, and chromatographing (55 g SiO$_2$; 95:5, CH$_2$Cl$_2$CH$_3$OH) gave the desired compound (462 mg, 81%).

c. 2(S)-t-Butyloxycarbonylamino-1-cyclohexyl-6-methyl-hept-3-ene

To a stirred −78° C. solution of Boc-cyclohexylalanine methyl ester (40 g, 140 mmol) in anhydrous toluene (250 mL) was added diisobutylaluminum hydride (130M %, 1.5M solution in toluene, 121.4 mL) at a rate to keep the internal temperature below −60° C. After stirring for an additional 20 minutes at −78° C., the aldehyde solution is used immediately as described below.

To a potassium hydride (35% dispersion in oil, 32.09 g) suspension in a 0° C. mixture of anhydrous THF/DMSO (1000 mL/200 mL) under dry N$_2$ was added 1,1,1,3,3,3-hexamethyldisilazane (209M %, 49.07 g) dropwise. After stirring at 0° C. for 1 hour, the resulting solution was added via cannula to a 0° C. flask containing isopentyltriphenylphosphonium bromide (209 M %, 125.66 g). The mixture was stirred vigorously for 1 hour at which time it was cooled to −78° C. The −78° C. aldehyde solution prepared above was then added via cannula. After stirring at −78° C. for 15 minutes, the mixture was allowed to slowly warm to room temperature and then heated to 40° C. for 12 hours. The mixture was then cooled to room temperature and quenched with methanol (7.65 mL) followed by aqueous Rochelle salts (100 mL saturated solution and 500 mL H$_2$O). The mixture was then extracted with ethyl acetate (2×). The combined extracts were washed with water and brine. Drying (MgSO$_4$) and evaporating provided crude alkene which was chromatographed on silica gel (ether/hexane) to give 16.5 g (38%) of the desired compound as an 85:15 mixture of cis:trans isomers. Mp=53°–55° C. Mass spectrum: M$^+$=309.

Analysis calculated for C$_{19}$H$_{35}$NO$_2$: C, 73.7; H, 11.4; N, 4.5. Found: C, 73.8; H, 11.4; N, 4.5.

d. 2(S)-t-Butyloxycarbonylamino-1-cyclohexyl-3,4-dihydroxy-6-methylheptane: The 3(R)4(S), 3(S)4(S), 3(R)4(R), and 3(S)4(R) Diastereomers To a solution of the resultant compound of Example 13 (8.50, 27.5 mmol) in dry THF (150 mL) were added OsO$_4$ (2.8 mL of a 2.5% solution in t-butanol and N-methylmorpholine N-oxide (9.28 g, 68.7 mmol). After 4 days the mixture was partitioned between ether (200 mL) and brine (100 mL). The aqueous layer was back-extracted with ether (2×100 mL), and the combined organic phase was washed with 10% Na$_2$SO$_3$, 0.1M H$_3$PO$_4$, and brine. Drying (MgSO$_4$) and evaporating provided a residue (10.81 g) which was chromatographed on silica gel to elute a 60% yield of the 4 diols in the following order.

3(R),4(S) Mass spectrum: (M+H)$^+$=344. Anal calcd. for C$_{19}$H$_{37}$NO$_4$: C, 66.4; H, 10.9; N 4.1. Found: C, 66.4; H, 10.8; N, 3.9.

3(S),4(S) Mass spectrum: (M+H)$^+$=344. Anal. calcd. for C$_{19}$H$_{37}$NO$_4$: C, 66.4; H, 10.9; N, 5.1. Found: C, 66.4; H, 11.1; N, 4.0.

3(R),4(R) Mass spectrum: (M+H)$^+$=344.

3(S),4(R) Mass spectrum: (M+H)$^+$=344. Anal. calcd. for C$_{19}$H$_{37}$NO$_4$ C, 66.4; H, 10.9; N, 4.1. Found: C, 66.0; H, 10.7; N, 4.0.

e. Boc-Phe-Ala Amide of 2(S)-Amino-1-cyclohexyl-3(R),4(S)-dihydroxy-6-methylheptane Using the procedure of 11b, but replacing the resultant compound of Example 11a with the 3(R),4(S) diastereomer of Example 11d gave the desired compound. Mass spectrum: (M-H)$^+$=560.

Anal. calcd. for C$_{321}$H$_{51}$N$_3$O$_6$: C, 66.3; H, 9.1; N, 7.5. Found: C, 66.0; H, 9.2; N, 7.3.

f. H-(4-OCH$_3$)Phe-Leu Amide of 2(S)-Amino-1-cyclohexyl-3(R),4(S)-dihydroxy-6-methylheptane.

Using the procedure of Example 33, but replacing Boc-Phe-Ala with Cbz-(3-I,4-OCH$_3$)Phe-Leu provided the protected iodinated product. Deprotection and de-iodination was achieved by hydrogenating 0.59 g in methanol (150 mL) with NaOAc.3H$_2$O (0.40 g), 2.5% Rh/BaSO$_4$ (1.5 g), 20% Pd/C (0.29 g) at 4 atmospheres H$_2$ for 2.5 h. Filtration and evaporation provided a residue which was partitioned between ethyl acetate and sat. aq. NaHCO$_3$. The organic layer was washed with dilute Na$_2$S$_2$O$_3$ and brine, dried, filtered, and evaporated to give a solid. Recrystallization from CH$_2$Cl$_2$/hexane provided 260 mg (65%) of the desired compound. HRMS: M$^+$ Calcd for C$_{30}$H$_{52}$N$_3$O$_5$: 534.3907. Measured: 534.3925.

g. H-Phe-Leu Amide of 2(S)-Amino-1-cyclohexyl-3(R),4(S)-dihydroxy-6-methylheptane.

Following the procedure of Example 11f, but replacing Cbz-(3-I,4-OCH$_3$)Phe-Leu with Cbz-Phe-Leu and omitting NaOAc.3H$_2$O and 2.5% Rh/BaSO$_4$ in the reduction step, provided the desired compound. Mass spectrum: (M+H)$^+$=504. Anal. Calcd for C$_{29}$H$_{49}$N$_3$O$_4$: C, 69.1; H, 9.8; N, 8.3. Found: C, 69.0; H, 10.1; N, 8.3.

h. 4-Carboxybutyroyl-Phe-Leu Amide of 2(S)-Amino-1-cyclohexyl-3(R),4(S)-dihydroxy-6-methylheptane To the resultant compound of Example 11g (0.5 g, 0.99 mmol) dissolved in dimethylformamide (10 ml), was added glutaric anhydride (0.11 g, 0.99 mmol). After stirring the reaction mixture for 24 h at room temperature, the solvent was evaporated and the resulting residue was partitioned between ethyl acetate and water. The organic phase was washed (brine) and dried ($Na_2SO_4$). Filtering and evaporation provided crude material which was chromatographed ($CH_3OH:CH_2Cl_2$, 5:95–10:90) to give 0.39 g of the desired compound, m.p. 195°–198° C. Mass spectrum: $(M+H)^+ = 618$. Anal. Calcd. for $C_{34}H_{55}N_3O_7H_2O$: C, 64.23; H, 9.04; N, 6.61. Found: C, 64.36; H, 8.76; N, 6.56.

EXAMPLE 12 a. 3(S)-t-Butyloxycarbonylamino-4-cyclohexyl-1,2(R,S)-dihydroxybutane

To a stirred solution of 2(S) t-butyloxycarbonylamino-1-cyclohexylbut-3-ene (1.00 g, 3.95 mmol) in THF (20 mL) were added $OsO_4$ solution (1.2 mL of a 2.5 W/V % solution in t-butanol) and N-methylmorpholine N-oxide (1.07 g, 7.90 mmol). After 24 hours, the mixture was partitioned between ether (50 mL) and brine (25 mL). The layers were separated, and the organic phase was extracted with ether (3×25 mL). The combined organic phase was washed with 10% $Na_2SO_3$ (4×10 mL), 1.0M H (2×8 mL), and brine (15 mL). Drying and evaporating provided the desired product as an oil (1.14 g, 100%). $^1$H-NMR shows a 1:1 mixture of diastereomers (NH 4.43 and 4.56 ppm).

b. Boc-Phe-His Amides of 3(S)-Amino-4-cyclohexyl-2(R,S)-hydroxy-1-t-butyldimethylsilyloxybutane The resultant compound of Example 12a (1.10 g, 3.82 mmol) was treated with anhydrous 1M HCl/$CH_3OH$ (80 mL) for 16 hours at which time evaporation and drying provided the corresponding amine hydrochloride (0.85 g, 100%).

To a suspension of the above hydrochloride salt (344 mg, 1.54 mmol) and imidazole (105 mg) in dichloromethane (15 mL) were added triethylamine (156 mg) and t-butyldimethylsilyl chloride (232 mg). The solvent was evaporated after 31 hours, and the residue was then re-dissolved in anhydrous dimethylformamide (DMF, 15 mL). Boc-Phe-His (619 mg) and 1-hydroxybenzotriazole (HOBT, 312 mg) were then added. After cooling the stirred solution to −23° C., 1,3-dicyclohexylcarbodiimide (DCC, 318 mg) was added. The mixture was warmed to room temperature 3 hours later. After 13 hours the solvent was evaporated in vacuo, and the residue was dissolved in ethyl acetate (40 mL), filtered, washed with saturated $NaHCO_3$ (2×10 mL) and brine (10 mL), and dried ($Na_2SO_4$). Filtration and evaporation provided a residue which was chromatographed on silica gel eluting with dichloromethane/methanol mixtures to give 441 mg (42%) of the desired product.

Mass spectrum: $(M+H)^+ = 686$.

Analysis calculated for $C_{36}H_{59}N_5O_6Si$: C, 63.0; H, 8.7; N, 10.2. Found: C, 62.8; H, 9.0; N, 9.9.

c. (1(S)-(Ethoxycarbonyl)-ethyl)-Phe-benzyl ester

A mixture of ethyl pyruvate (4.17 g, 36 mmol), Phe-benzyl ester p toluenesulfonic acid salt (14.4 g, 34 mmol) and NaOAc (5.53 g, 67 mmol) in 200 ml of absolute ethanol was stirred at 0° C. for 30 min. NaCNBH$_3$ (2.19 g, 34.7 mmol) in 200 ml of absolute ethanol was added dropwise over one hour. After the addition was complete, the reaction mixture was stirred at room temperature for 36 h. The mixture was filtered and the filtrate was evaporated under reduced pressure. The resulting oil was chromatographed, eluting with ethyl acetate/hexane (1:4), to afford 3.5 g of less polar diastereomer and 1.5 g of more polar diastereomer (the desired product). Mass spectrum (more polar isomer): $(M+H)^+ = 365$. NMR (CDCl$_3$): 0.9 (6H, g), 1.1 (3H, t), 1.2 (3H, d), 1.4–1.7 (11H, m), 4.1 (2H, m), 6.8 (1H, s), 7.3 (5H, m), 7.5 (1H, s).

d. (1(S)-(Ethoxycarbonyl)-ethyl)-Phe-His Amide of 2(S)-Amino-1-cyclohexyl-3(R),4(S)-dihydroxy-6-methylheptane The more polar diastereomer isolated in Example 12c (700 mg, 1.97 mmol) was hydrogenated with 10% Pd/C at 4 atmospheres of H$_2$ in ethanol for several hours. The mixture was filtered and the filtrate was evaporated under reduced pressure. The resultant crude product of the reduction (130 mg, 0.49 mmol) was coupled to the His Amide of (S)-Amino-1-cyclohexyl-3(R),4(S)-dihydroxy-6-methylheptan e dihyrochloride (190 mg, 0.42 mmol), following the procedure of Example 12b. The product was chromatographed, eluting with 5% methanol/chloroform, to afford 120 mg of the desired product, m.p. 84°–86° C. Mass spectrum: $(M+H)^+ = 628$. NMR (CDCl$_3$); 0.9 (6H, g), 1.1 (3H, t), 1.2 (3H, d), 1.4–1.7 (11H, m), 4.1 (2H, m), 6.8 (1H, s), 7.3 (5H, m), 7.5 (1H, s).

EXAMPLE 13 a. 4(S)-t-Butyloxycarbonylamino-5-cyclohexyl-3(R,S)-hydroxyl-1-pentene

To a stirred −78° C. solution of Boc-cyclohexylalanine methyl ester (10.2 g, 35.8 mmol) in dry toluene (60 ml) was added diisobutylaluminum hydride (34 ml of a 1.5M solution in toluene). After 30 min, vinyl magnesium bromide (108 ml of 1M solution in tetrahydrofuran (THF)) was added. After stirring for 15 h at 0° C., the mixture was carefully quenched with methanol, treated with Rochelle salts (22 ml of saturated aqueous solution in 140 ml H$_2$O), and filtered. After extracting the solids 5 times with ethyl acetate, the extracts and filtrate were combined and the organic phase was washed with brine, dried, filtered and evaporated to an oil (10.2 g). Chromatography on silica gel eluting with hexane/ethyl acetate mixtures provided 6.1 g (60%) of the desired product.

Anal. Calcd. for $C_{16}H_{29}NO_3 1/4 H_2O$: C, 66.8; H, 10.3; N, 4.9.

Found: C, 66.9; H, 10.2; N, 4.7.

b. 4(S)-Cyclohexylmethyl-5(R,S)-vinyl-2-oxazolidinone.

The resultant product of Example 13a (2.80 g, 9.88 mmol) in dry dimethylformamide (DMF) (50 ml) was added to a stirred suspension of NaH (593 mg of a 60% dispersion in oil, 14.8 mmol, hexane washed) in dry DMF (50 ml). After 3 h, the mixture was quenched (750 ml water+100 ml brine) and extracted with ether (5×100 ml). The combined organic phase was washed with brine (3×50 ml), dried (MgSO4), filtered and evaporated to an oil (2.23 g). The NMR spectrum of the crude product revealed an 82:18 mixture of 5S:5R diastereomers. Silica gel chromatography gave 80% recovery of pure diastereomers. 5S:

Anal. Calcd. for $C_{12}H_{19}NO_2$: C, 68.9; H, 9.1; N, 6.7. Found: C, 68.4; H, 9.2; N, 6.5. Mass spectrum: $(M+1)^+ = 210$. 5R: Mass spectrum: $(M+1)^+ = 210$.

c. (3S,4S)-3-Hydroxy-4-amino-5-cyclohexyl-1-pentene.

To the resultant 5S diasteriomer from Example 13b (2.06 g, 9.84 mmol) in dioxane (180 ml) and water (120 ml) was added barium hydroxide octahydrate (6.24 g, 19.8 mmol). The mixture was refluxed for 18 h, cooled, filtered, concentrated, taken up in water and extracted with ethyl acetate which was dried over $Na_2SO_4$ and evaporated to afford 1.64 g (91%) of the desired product, m.p.: 59°-61° C.

Anal. Calcd. for $C_{11}H_{21}NO$: C, 72.08; H, 11.55; N, 7.64.

Found: C, 71.67; H, 11.68; N, 7.36.

d. (3S,4S)-3 Hydroxy-4 tert-butyloxycarbonylamino-5-cyclohexyl-1-pentene.

To the resultant compound from Example 13c (1.62 g, 8.84 mmol) in methylene chloride (20 ml) was added di-tert-butyldicarbonate (1.93 g, 8.84 mmol). The mixture was stirred for 14 h, diluted with ethyl acetate, washed sequentially with 0.5M $H_3PO_4$, $Na_2SO_4$ and evaporated to afford 2.51 g (100%) of the desired compound.

e. (3S,4S)-3-Methoxyethoxymethoxy-4-tertbutyloxycarbonylamino-5-cyclohexyl-1-pentene.

To the resultant compound from Example 13d (2.51 g, 8.84 mmol) in methylene chloride (20 ml) was added diisopropyl ethylamine (4.60 ml, 26.4 mmol) and methoxyethoxy chloromethane (3.00 ml, 26.3 mmol). After stirring at room temperature for 24 h the mixture was concentrated, diluted with ethyl acetate, washed with 0.5M $H_3PO_4$, saturated $NaHCO_3$ solution, then brine, dried over $Na_2SO_4$, and evaporated. Chromatography on silica gel with ethyl acetate/hexane mixtures afforded 2.63 g (80%) of the desired product as an oil. EI-MS: $M^+ = 371$.

f. (2RS,3R,4S)-3-Methoxyethoxymethoxy-4-tertbutyloxycarbonylamino-5-cyclohexyl-1,2-oxopentane.

To the resultant compound from Example 13e (5.41 g, 14.56 mmol) in methylene chloride (50 ml) was added 3-chloroperbenzoic acid (6.28 g). After stirring at room temperature for 60 h the mixture was concentrated, diluted with ethyl acetate, washed with cold 1:1 15% aqueous $Na_2SO_3$ solution/saturated $NaHCO_3$ solution (2×200 ml), saturated $NaHCO_3$ solution (3×100 ml) then brine (1×100 ml), dried over $Na_2SO_4$, and evaporated to afford 4.57 g (81%) product as an oil. EI-MS: $M^+ = 387$.

g. (2'S,1'R,5S)-3-Ethyl-5-(1'-methoxyethoxymethoxy-2'-tert-butyloxycarbonylamino -3'-oxazolidin-2-one.

To the resultant compound from Example 13f (310 mg, 0.80 mmol) in isopropanol (5 ml) was added ethyl amine (200 mg, 4 mmol). The mixture was heated at 70° C. for 48 h, evaporated and dissolved in methylene chloride (5 ml). To this solution was added triethylamine (0.34 ml, 2.4 mmol) and phosgene in toluene (1.0 ml, 1.2 mmol, 12.5% solution). After 2 h the mixture was diluted with ethyl acetate, washed with 0.5M $H_3PO_4$, saturated $NaHCO_3$ solution then brine, dried over $Na_2SO_4$ and evaporated. Chromatography of the residue on silica gel with 1:1 ethyl acetate/hexane provided 14.3 mg (4%) of the 5R isomer followed by 63.0 mg (17%) of the desired 5S isomer, both as oils.

5S-Isomer: $^1$H-NMR (CDCl3) delta 4.83 (d,1H), 4.80 (d,1H), 4.58 (m,1H), 3.49 (s,3H), 1.43 (s,9H), 1.15 (t,3H).

5R Isomer: MS $(M+H)^+ = 459$.

h. Boc-His Amide of (2'S,1'R,5S)-3-Ethyl 5-(1'-hydroxy-2-amino-3-cyclohexylpropyl -oxazolidin-2-one.

The resultant compound from Example 13 g (2.23 g, 4.87 mmol) was stirred for 1 h in 4.5M ethanolic HCl (15 ml). The solvent was evaporated with ether and toluene chasers and the residue was dissolved in dimethylformamide (25 ml) and treated with Boc-His-OH (1.37 g, 5.36 mmol) and 1-hydroxybenzotriazole (1.98 g, 14.6 mmol). The mixture was cooled to −23° C. and N-methylmorpholine (600 microliters, 5.46 mmol) was added followed by 1-(3-dimethylaminopropyl)-3-ethylcarbodiimide (1.05 g, 5.46 mmol). The mixture was stirred at −23° C. for 2 h and at room temperature 16 h, and then was poured into saturated $NaHCO_3$ solution and extracted into ethyl acetate which was washed with water and brine, then dried over $Na_2SO_4$ and evaporated. Chromatography of the residue on silica gel with 4% methanol in chloroform provided 1.785 g (72%) of the desired product as a white solid. $^1$H-NMR (CDCl3, TMS) delta 7.58 (s,1H), 6.89 (s,1H), 6.26 (m,1H), 4.39 (m,1H), 4.13 (m,1H), 4.40 (m,1H), 3.30 (m,2H), 3.16 (dd,1H), 3.01 (dd,1H), 1.47 (s,9H), 1.17 (t,3H).

i. 3-(t-Butyloxycarbonyl)-4-(cyclohexylmethyl)-2,2-dimethyl-5-vinyloxazolidine.

The procedure of S. Thaisrivong (J. Med. Chem. 1987, 30, 976) was employed. A solution of 40 g of the resultant compound of Example 13a and 102 g of 2-methoxypropene in 250 ml of dichloromethane was stirred at room temperature. Solid pyridinium p-toluenesulfonate (PPTS) (177 g) was added slowly to the reaction mixture. After addition was complete, the reaction was stirred for 1 h and neutralized by addition of solid sodium bicarbonate. The solids were filtered and the filtrate was concentrated. Flash chromatography on silica gel gave 57 g of the desired compound. IR (CDCl3) 1690 (C=0 carbamate) cm$^{-1}$; $^1$H NMR (CDCl3) delta 5.95 (m,1H), 5.32 (m,1H), 5.20 (dt,1H), 4.27 (dd,1H), 1.47 (s,9H).

Anal. Calcd. for $C_{19}H_{33}NO_3$: C, 70.55; H, 10.28; N, 4.33.

Found: C, 70.47; H, 10.27; N, 4.09.

j. 3-(t-Butyloxycarbonyl)-4-(cyclohexylmethyl)-2,2-dimethyloxazolidine-5-carboxaldehyde.

A solution of 10 g of the resultant compound of Example 13i in 150 ml of 2:1 dichloromethane:methanol was cooled in an dry ice acetone bath. Ozone was bubbled through the solution until a blue color persisted (1 h). Dry nitrogen was then bubbled through the reaction mixture to remove excess dissolved ozone. The reaction mixture was cannulated into a suspension of 8 g zinc dust, 8 ml glacial acetic acid, 200 ml water, and 200 ml of methanol cooled to −45° C. After 5 min the bath was removed and the mixture allowed to warm to room temperature overnight. 100 ml of saturated sodium chloride was added and the entire reaction mixture extracted with two 300 ml portions of dichloromethane. The combined dichloromethane extracts were decanted, dried (MgSO$_4$), filtered, and evaporated. The crude aldehyde was purified by flash chromatography (1:4) ethyl acetate:hexane to give 9.7 g of the desired compound as a mixture of diastereomers (3:1 trans:cis) as judged by the integrated resonances of the two aldehyde protons. IR (CDCl$_3$) 1735 (C=O aldehyde), 1690 (C=O carbamate) cm$^{-1}$; $^1$H NMR (CDCl$_3$) delta 9.83 (s,1H,CHO), 9.73 (d,1H,CHO cis diastereomer), 4.14 (m,1H), 1.46 (s,9H).

Anal. Calcd. for $C_{18}H_{31}NO_4$: C, 66.43; H, 9.60; N, 4.30.

Found: C, 65.27; H, 9.79; N, 4.20.

Equilibration of Aldehyde Isomers

A suspension of 25 g of the above aldehyde in 300 ml of methanol and powdered potassium carbonate (10.7 g) was stirred at room temperature for 6 h. The reaction mixture was cooled in an ice-water bath and treated with 9.3 g of glacial acetic acid for 5 min. A solution of 0.5M sodium dihydrogen phosphate (300 ml) was added to the mixture. After 30 min, the solution was concentrated to one-half the volume under reduced pressure and extracted with ether (600 ml). The combined ether extracts were dried (MgSO$_4$), filtered, and concentrated. The aldehyde was purified by flash chromatography using (1:4) ethyl acetate:hexane to give 19.5 g of the desired compound as an 8:1 mixture of trans:cis diastereomers.

k. (5S,4′S,5′R)-5-(3-(t-Butyloxycarbonyl)-4-(cyclohexylmethyl) -2,2-dimethyloxazolidin-5-yl)-3-methylenedihydrofuran-2(4H)-one.

A solution of 16.52 g (51 mmol) of the resultant compound of Example 13j in 15 ml of anhydrous tetrahydrofuran was treated with 3.98 g (61 mmol) of freshly activated zinc dust. With vigorous stirring, the mixture was treated with 10 g (56 mmol) of methyl 2-(bromomethyl)acrylate at a rate which maintained the temperature at 50°-60° C. Upon completion of the addition, the mixture was stirred at 50° C. for 1 h. After being allowed to cool, the mixture was poured into 100 ml of cold 1M HCl and extracted with dichloromethane (3×100 ml). The combined organic layers were washed successively with saturated aqueous NaHCO$_3$ and H$_2$O, dried over Na$_2$SO$_4$, and concentrated. Silica gel chromatography using 9:1 hexane:ethyl acetate provided 10.83 g (61%) of the desired compound. $^1$H NMR (CDCl$_3$) delta 0.8-2.0 (br envelope), 1.49 (s,9H), 1.54 (s,3H), 1.57 (s,3H), 2.93 (ddt,J=18,6,3Hz,1H), 3.05 (m,1H), 3.70 (m,1H), 4.07 (m,1H), 4.47 (ddd,J=13,9,6Hz,1H), 5.70 (br t,J=3Hz,1H), 6.28 (t,J=3Hz,1H). Mass spectrum: (M+H)$^+$=394.

Anal. Calcd. for $C_{22}H_{35}NO_5$: C, 67.15; H, 8.96; N, 3.56.

Found: C, 67.66; H, 9.11; N, 3.60.

(3S,5S,4′S,5′R)-5-(3-(t-Butyloxycarbonyl)-4-(cyclohexylmethyl) -2,2-dimethyloxazolidin-5-yl)-3-methyldihydrofuran-2(3H)-one.

A mixture of 8.03 g (20 mmol) of the resultant compound of Example 13k and 0.81 g of 10% palladium on carbon in 200 ml of ethyl acetate was shaken under 4 atmospheres of H$_2$. After filtration, concentration of the filtrate gave 7.58 g (94%) of the desired compound. $^1$H NMR (CDCl$_3$) delta 0.8-2.0 (br envelope), 1.31 (s,3H), 1.48 (s,9H), 1.54 (s,3H), 1.58 (s,3H), 2.57 (m,1H), 2.68 (m,1H), 3.74 (m,1H), 4.04 (m,1H), 4.31 (ddd,J=13,9,6Hz,1H). Mass spectrum: (M+H)$^+$=396.

m. Boc-Phe-His Amide of (5S,1′R,2′S)-5-(2-Amino-3-cyclohexyl-1-hydroxy) -3-methylenedihydrofuran-2(4H)-one.

Using the procedure of Example 13h with the resultant compound of Example 13k and using Boc-Phe-His-OH in place of Boc-His-OH gave the desired compound, mp 171°-173° C. Mass spectrum: (M+H)$^+$=638.

Anal. Calcd. for $C_{34}H_{47}N_5O_7$ 1.5 H$_2$O: C, 61.43; H, 7.58; N, 10.53.

Found: C, 61.14; H, 7.28; N, 10.40.

n. Boc-Phe-His Amide of (3S,5S,1′R,2′S)-5-(2-Amino-3-cyclohexyl-1-hydroxy) -3 methyldihydrofuran-2-(3H)-one.

Using the procedure of Example 13h with the resultant compound of 131 and using Boc-Phe-His-OH in place of Boc-His-OH gave the desired compound, mp 129°-130° C. Mass spectrum: (M+H)$^+$=640.

Anal. Calcd. for $C_{34}H_{49}N_5O_7$ 1.75 H$_2$O: C, 60.83; H, 7.88; N, 10.43.

Found: C, 60.69; H, 7.42; N, 10.27.

o. Boc-Phe-His Amide of (4S,5R,6S)-6-Amino-7-cyclohexyl-4,5-dihydroxy-1-hepten-2-oic Acid Sodium Salt.

A solution of 32 mg (0.50 mmol) of the resultant compound of Example 13m in 1 ml of tetrahydrofuran and 0.5 ml of H$_2$O was cooled to 0° C. and treated with 0.05 ml (0.15 mmol) of 3 N NaOH. The resulting solution was stirred at 0° C. for 3 h, and concentrated to dryness. The residue was washed with ethyl acetate and dried in vacuo to give the desired compound, mp 198°-200° C. Mass spectrum: (M+H)$^+$=678; (M−Na+2H)$^+$=656.

EXAMPLE 14

Boc-Phe-His Amide of (2S,4S,1′R,2′S)-2-(2 Amino-7-cyclohexyl -4,5-dihydroxyheptan-2-oic Acid Sodium Salt.

Using the procedure of Example 13o with the resultant compound of Example 13n gave the desired compound, mp 154°-155° C. Mass spectrum: (M−Na+2H)$^+$=658.

EXAMPLE 15 a. N (3-Methylbutyl)-5-t-butyloxycarbonylamino-6-cyclohexyl-1-hexen-4-ol-2-carboxamide A solution of N-(3 methylbutyl)-2-methyl propenamide (643 mg, 4.15 mmol) in 25 ml of dry tetrahydrofuran was cooled under an N$_2$ atmosphere to −78° C. and treated dropwise with 3.28 ml (8.5 mmol) of n-butyllithium in hexane. The resulting solution was warmed to 0° C. for 20 minutes, recooled to −78° C. and treated with 6.2 mL (6.2 mmol) of chlorotitanium triisopropoxide in hexane. After again warming to 0° C. for 5 minutes, the dark solution was recooled to −78° C. treated with a solution of N-t-butyloxycarbonyl cyclohexylalaninal (670 mg, 2.3 mmol) in 5 ml of tetrahydrofuran, stirred for 5 minutes at −78° C., warmed to 0° C. for 20 minutes and quenched with saturated aqueous ammonium chloride. The resulting suspension was treated with ca. 50 ml of ether, stirred until the salts became white, extracted with two 100 ml portions of ether, dried over MgSO$_4$ and concentrated in vacuo. The crude mixture was separated by flash column chromatography using 4:1 chloroform/ethyl acetate to give 249 mg (25%) of the (4S,5S) product ($R_f$ 44), 292 mg (31%) of the (4R,5S) product ($R_f$ 0.36, 3:2 chloroform/ethyl acetate) and 184 mg (20%) of a ca. 1:1 mixture of the two products. Mass spectrum: M$^+$=410.

b. (4S,5S) N-(3-Methylbutyl)-5-amino-6-cyclohexyl-1-hexen-4-ol-2-carboxamide hydrochloride The (4S,5S) diastereomer from Example 15a (31.5 mg, 0.077 mmol) was treated with 0.5 mL of a 4M solution of HCl in dioxane and allowed to stand at ambient temperature for 1 hour. After removal of the solvent in vacuo, the residue was treated twice with 0.5 mL of anhydrous ether followed each time by removal of the solvent in vacuo. The crude amine hydrochloride was used without further purification.

c. Boc-Phe-His amide of (4S,5S)-N-(3-methylbutyl)-5-amino-6-cyclohexyl-1-hexen-4-ol-2-carboxamine A solution of 52 mg (0.13 mmol) of Box-Phe-His OH and 52 mg (0.39 mmol) of 1-hydroxybenzotriazole monohydrate in 0.6 mL of dimethylformamide was cooled to −23° C., treated with 25 mg (0.13 mmol) of 1-ethyl-3-(dimethylaminopropyl)-carbodiimide hydrochloride, and allowed to stir for 1 hour. A solution of 0.13 mmol of the resultant compound of Example 15b and 29 microliters (0.25 mmol) of 4-methylmorpholine in 0.6 mL of dimethylformamide was subsequently added, and the resulting solution was stirred at −23° C. for 3 hours and at ambient temperature for 16 h. After dilution with 10 mL of ethyl acetate, the solution was washed sequentially with 1 mL of saturated aqueous NaHCO$_3$ and 1 mL of H$_2$O, dried over MgSO$_4$, and concentrated in vacuo. Purification by flash column chromatography using 10% methanol in chloroform gave 49 mg (55%) of the desired compound ($R_f$ 0.20, 10% methanol in chloroform) which was recrystallized from tetrahydrofuran/hexane, m.p. 178°–180° C. (dec). Mass spectrum: M+694. Anal. Calcd for C$_{38}$H$_{38}$H$_6$O$_6$0.5 H$_2$O: C, 64.84; H, 8.45; N, 11.94. Found: C, 65.16, H, 8.64; N, 11.89.

EXAMPLE 16 a. 4(S)-t-Butyloxycarbonylamino-5-cyclohexyl 3(R,S)-hydroxy-1-pentene

To a stirred −78° C. solution of Boc-cyclohexylalanine methyl ester (10.2 g, 35.8 mmol) in dry toluene (60 ml) was added diisobutylaluminum hydride (34 ml of a 1.5M solution in toluene). After 30 min., vinyl magnesium bromide (108 ml of 1M solution in tetrahydrofuran (THF)) was added. After stirring for 15 hours at 0° C., the mixture was carefully quenched with methanol, treated with Rochelle salts (22 ml of saturated aqueous solution in 140 ml H$_2$O), and filtered. After extracting the solids 5 times with ethyl acetate, the extracts and filtrate were combined and the organic phase was washed with brine, dried, filtered and evaporated to an oil (10.2 g). Chromatography on silica gel eluting with hexane/ethyl acetate mixtures provided 6.1 g (60%) of the desired product.

Anal. calcd. for C$_{16}$H$_{29}$NO$_3$ 1/4H$_2$O; C, 66.8; H, 10.3; N, 4.9. Found: C, 66.9; H, 10.2; N, 4.7.

b. 4(S)-Cyclohexylmethyl-5(R,S)-vinyl-2-oxazolidinone

The resultant product of Example 16a (2.80 g, 9.88 mmol) in dry dimethylformamide (DMF) (50 ml) was added to a stirred suspension of NaH (593 mg of a 60% dispersion in oil, 14.8 mmol, hexane washed) in dry DMF (50 ml). After 3 hours, the mixture was quenched (750 ml water+100 ml brine) and extracted with ether (5×100 ml). The combined organic phase was washed with brine (3×50 ml), dried (MgSO$_4$), filtered and evaporated to an oil (2.23 g). The NMR spectrum of the crude product revealed an 82:18 mixture of 5 S:5 R diastereomers. Silica gel chromatography gave 80% recovery of pure diastereomers. 5 S:

Anal. calcd. for C$_{12}$H$_{19}$NO$_2$; C, 68.9; H, 9.1; N, 6.7. Found: C, 68.4; H, 9.2; N, 6.5.

Mass spectrum: (M+1)$^+$ =210. 5R: Mass spectrum: (M+1)$^1$ 210.

c. (3S,4S)-3-Hydroxy-4-amino-5-cyclohexyl-1-pentene

To the resultant 5S diasteriomer from Example 16b (2.06 g, 9.84 mmol) in dioxane (180 mL) and water (120 mL) was added barium hydroxide octahydrate (6.24 g, 19.8 mmol). The mixture was refluxed for 18 hours, cooled, filtered, concentrated, taken up in water and extracted with ethyl acetate which was dried over Na$_2$SO$_4$ and evaporated to afford 1.64 g (91%) of the desired product, m.p. 59°–61° C.

Anal. calcd. for C$_{11}$H$_{21}$NO; C, 72.08; H, 11.55; N, 7.64. Found: C, 71.67; H, 11.68; N, 7.36.

d. (3S,4S)-3-Hydroxy-4-tert-butoxycarbonylamino-5-cyclohexyl-1-pentene

To the resultant compound from Example 16c (1.62 g, 8.84 mmol) in methylene chloride (20 mL) was added di-tert-butyldicarbonate (1.93 g, 8.84 mmol). The mixture was stirred for 14 hours, diluted with ethyl acetate, washed sequentially with 0.5M H$_3$PO$_4$, saturated NaHCO$_3$ solution and brine, then dried over Na$_2$SO$_4$ and evaporated to afford 2.51 g (100%) of the desired compound.

e. (3S,4S)-3-tert-Butyldimethylsilyloxy-4-tertbutoxycarbonylamino-5-cyclohexyl-1-pentene To the resultant compound from Example 16d (0.264 g, 0.932 mmol) in DMF (4 mL) was added tert-butyldimethylsilyl chloride (0.300 g, 1.99 mmol) and imidazole (0.269 g, 3.95 mmol). The mixture was stirred at room temperature for 12 hours, poured into ethyl acetate and washed sequentially with 0.5M H$_3$PO$_4$, saturated NaHCO$_3$ solution and brine, then dried over Na$_2$SO$_4$ and evaporated to afford 0.355 g (96%) of the desired compound. Mass spectrum: (M+H)$^+$ =398.

f. (2RS,3R,4S)-3-tert-Butyldimethylsilyloxy-4-tert-butoxycarbonylamino-5-cyclohexyl-1,2-oxopentane The resultant compound from Example 16e (0.355 g, 0.893 mmol) in methylene chloride (8 mL) was treated with m chloroperbenzoic acid (0.758 g, 3.51 mmol) and stirred at ambient temperature for 14 hours. The mixture was concentrated, dissolved in ethyl acetate, washed sequentially with cold 10% aqueous $Na_2SO_3$ solution, saturated $NaHCO_3$ solution and brine, and then dried over $Na_2SO_4$ and evaporated to afford 0.374 g (100%) of the desired compound. Mass spectrum: $(M+H)^+ = 404$.

g. (2RS,3R,4S)-3-Hydroxy-4-tert-butoxycarbonylamino-5-cyclohexyl-1,2-oxopentane The resultant compound from Example 16f (2.10 g, 5.07 mmol) was treated with 1M tetrabutylammonium fluoride in tetrahydrofuran (10 mL). The mixture was stirred at 0° C. for 1 hour, poured into ethyl acetate, washed with water and brine, then dried over $Na_2SO_4$ and evaporated. Chromatography on silica gel (0.5% methanol in chloroform) afforded 1.13 g (74%) of the desired compound. Mass spectrum: $(M+H)^+ = 300$.

h. (2S,3R,4S)-1-Azido-2,3-dihydroxy-4-tertbutoxycarbonylamino-5-cyclohexylpentane The resultant compound from Example 16g (1.12 g, 3.74 mmol), ammonium chloride (0.374 g, 6.98 mmol) and sodium azide (0.580 g, 8.92 mmol) were refluxed in methanol (25 mL) for 12 hours. The mixture was concentrated, then taken up in ethyl acetate, washed with water and brine, dried over $Na_2SO_4$ and evaporated. Chromatography on silica gel (20% ether in hexane) afforded 0.461 g (36%) of the desired compound followed by 0.323 g (25%) of the 4-R isomer. M.p. (4S-Diasteriomer): 93°–94° C. Mass spectrum: (4R-Diasteriomer): $(M+H)^+ = 343$.

i. Boc-Phe-His-OH Amide of (2S,3R,4S)-1-Azido-2,3-dihydroxy-4-amino-5-cyclohexylpentane The resultant compound from Example 16h (53.0 mg, 0.155 mmol) was stirred in 4M HCl/diozane for 1 hour and evaporated. The residue was taken up in tetrahydrofuran (3 mL), treated with N-methylmorpholine (18 1, 0.16 mmol) and cooled to 0° C.

To Boc-Phe-His OH (0.172 mmol) in tetrahydrofuran (2 mL) at −12° C. was added N-methylmorpholine (19 1, 0.17 mmol) followed by isobutylchloroformate (22 1, 0.17 mmol). After 3 minutes the amine solution was added and the mixture was stirred for 15 minutes at −12° C. and 2 hours at room temperature. The mixture was diluted with ethyl acetate and washed sequentially with 0.5M $H_3PO_4$, saturated $NaHCO_3$ solution and brine, then dried over $Na_2SO_4$ and evaporated. Chromatography of the residue on silica gel (3% methanol in chloroform) afforded 86.8 mg (100%) of the desired compound.

j. Boc-Phe-His Amide (4-amino) of (2S,3R,4S)-1,4-Diamino-2,3-dihydroxy-5-cyclohexylpentane A solution of the resultant compound from Example 16i (0.106 mmol) in methanol (4 ml) was hydrogenated at atmospheric pressure (10% Pd/C) for 16 hours. Filtration and evaporation provided the desired compound.

EXAMPLE 17 a. (3S,4S)-1-(2 Methylpropylcarbonylamino)-3-hydroxy-4-t-butyloxycarbonylamino-5-cyclohexylpentane To (3S,4S)-1-amino-3-hydroxy-4-t-butyloxycarbonylamino-5-cyclohexylpentane (30.8 mg, 0.102 mmol) in dry methylene chloride (3 mL) at 0° C. was added 3-methyl-butyroyl chloride (0.123 mmol) and triethylamine (20.0 microliters, 0.143 mmol). The mixture was stirred at 0° C. for 1 hour, evaporated, taken up in methanol (3 mL) and treated with 1M NaOH (1 mL). After stirring for 1 hour, the mixture was diluted with ether, washed sequentially with 0.5M $H_3PO_4$, saturated $NaHCO_3$ solution, and brine, and then dried over $Na_2SO_4$ and evaporated to afford the desired product.

b. Boc-Phe-His Amide of (3S,4S)-1-(2-Methylpropylcarbonylamino)-3-hydroxy-4-amino-5-cyclohexylpentane (3S,4S)-1-(2-Methylpropylcarbonylamino)-3-hydroxy -4-t-butyloxycarbonylamino-5-cyclohexylpentane (0.0672 mmol) was stirred in 4M HCl/dioxane (1.5 mL) for 1 hour, and evaporated. The residue was dissolved in dry tetrahydrofuran (3 mL), treated with N-methylmorpholine (8.5 microliters, 0.077 mmol), and cooled to −12° C.

To Boc-Phe-His-OH (0.082 mmol) in dry tetrahydrofuran (3 mL) was added N methylmorpholine (9.1 microliters, 0.083 mmol). The mixture was cooled to −12° C. and treated with isobutylchloroformate (10.6 microliters, 0.081 mmol. After stirring for 3 minutes the amine solution was added and the reaction was stirred for 15 minutes at −12° C. and 2 hours at room temperature. The mixture was diluted with ethyl acetate which was washed sequentially with 0.5M $H_3PO_4$, saturated $NaHCO_3$ solution, and brine, then dried over $Na_2SO_4$ and evaporated to a white solid. Trituration with ether afforded the desired product as a white solid.

EXAMPLE 18 a. Boc-Phe-His-Sta amide of benzylamine

To the amine hydrochloride of Boc-Sta amide of benzylamine (100 mg. 0.34 mmole) in 4 mL of dimethyl formamide (DMF) was addedtriethylamine (47 uL, 0.34 mmole). The solution was cooled to 0° C. and Boc-Phe-His-OH was added (136 mg, 0.34 mmole), followed by 1-hydroxybenzotriazole (70 mg, 0.51 mmole) and then dicyclohexylcarbodiimide (72 mg, 0.34 mmole). The solution was stirred at 0° C. for 8 hours and then at room temperature for 4 hours. The solution was filtered and the solvent was evaporated under vacuum. The residual solid was dissolved in ethyl acetate (50 mL) and washed with saturated sodium bicarbonate and then saturated sodium chloride solution, dried with $MgSO_4$, filtered and the solvent evaporated in vacuo. The crude product was purified by silica gel column (8% MeOH:92% $CH_2Cl_2$) and 110 mg. (50%) of product was obtained. m.p. 169°–170° C. Mass spectrum: $M+ = 648$. Anal. calcd. for $C_{35}H_{48}N_6O_6$: C 64.79; H 7.46; N 12.95. Found: C 64.56; H 7.40; N 12.81.

b. Boc-Phe-His ACHPA amide of 2-methylbutylamine

Using the procedure of Example 18a, but using the amine hydrochloride of Boc-ACHPA amide of 2-methylbutylamine gave the desired compound.

EXAMPLE 19 a. 3 t-Butyloxycarbonylamino-5-methylhex-1-ene

To a stirred suspension of methyltriphenyl phosphonium bromide (10.97 g, 30.70 mmol) in anhydrous tetrahydrofuran (200 ml) at −78° C. (dry ice/acetone bath) under an argon atmosphere, was added n butyl lithium (19.8 ml of a 1.55M hexane solution) dropwise over the course of 5 minutes. After 10 minutes, the −78° C. bath was replaced with a 0° C. bath for one half hour, at which time the resulting orange solution was cooled again to −78° C. The solution was then added dropwise by cannula to a stirred −78° C. solution of Boc-leucinal (6.00 g, 27.91 mmol) in anhydrous tetrahydrofuran (30 ml) over the course of one-half hour. The mixture was then allowed to warm to room temperature during a 3 hour period after which water (150 ml) was added. Extraction with hexane (4×100 ml) provided a combined organic phase which was washed with brine (100 ml), dried ($Na_2SO_4$, and concentrated to give crude 3-t-butyloxycarbonylamino-5-methylhex-1-ene (6.5 g). Chromatography with ether/hexane (1/9) provided pure 3-t-butyloxycarbonyl-amino-5 methylhex-1-ene (3.71 g, 60%). Mass spectrum: EI, $M^+ - 57 = 156$; CI, $(M+H)^+ = 214$.

b. 3-t-Butyloxycarbonylamino-5-methyl- 1,2-oxohexane

To a stirred solution of 3-t-butyloxycarbonylamino-5-methylhex-1-ene (0.43 g, 2.0 mmol) in dichloromethane (20 ml) was added m-chloroperbenzoic acid (MCPBA, 1.51 g of 80% MCPBA, 7.0 mmol). After 68 hours the reaction mixture was cooled to 0° C., and 0° C. 10% $Na_2SO_3$ (5 ml) was added with stirring. After 15 minutes, the solid was filtered off and extracted with dichloromethane. The combined organic phase was washed sequentially with 0° C. 10% $Na_2SO_3$ (6 ml), saturated $NaHCO_3$ (2×6 ml), and water (5 ml). Drying ($MgSO_4$), filtering, and evaporating provided crude 3-t-butyloxycarbonylamino-5-methyl-1,2-oxohexane (0.42 g) which was chromatographed on 50 g of $SiO_2$ (hexane/ether, 3/1) to give pure 3-t-butyloxycarbonyl-amino-5-methyl-1,2-oxohexane (0.27 g, 59%). Mass spectrum: $M^+ = 229$.

c. 3-t-Butyloxycarbonylamino-1-cyclohexyl-mercapto-2-hydroxy-5-methylhexane

To a stirred solution of 3-t-butyloxycarbonylamino-5 methyl 1,2-oxohexane (200 mg, 0.87 mmol) in methanol (8.7 ml) was added cyclohexyl mercaptan (102 mg, 0.87 mmol) and triethylamine (88 mg, 0.87 mmol). The resultant solution was refluxed for 2 hours and then evaporated to give a residue which was chromatographed on 15 g of 40 m $SiO_2$ (7/3, hexane/ether) to give 281 mg (94%) of 3-t-butyloxy-carbonylamino-1-cyclohexyl-mercapto-2-hydroxy-5-methylhexane. Mass spectrum: $M^+ 345$.

Analysis Calcd.: C, 62.6; H, 10.2; N, 4.0.
Found: C, 62.9; H, 10.4; N, 3.9.

d. 3-Amino-1-cyclohexylmercapto-2-hydroxy-5-methylhexane hydrochloride

To a stirred solution of approximately 0.25 mmol of the resultant compound of Example 19c in methanol was added methanolic HCl (10 ml of approximately 0.75M). After 8–12 hours, the solvent was evaporated, and the desired compound was used without further purification.

e. Boc-His Amide of 3-amino-1-cyclohexylmercapto-2-hydroxy-5-methylhexane

To a stirred suspension of Boc-His OH (72 mg, 0.28 mmol) in dry dimethylformamide (3 ml) at −23° C. was added a solution of 3-amino-1-cyclohexylmercapto-2-hydroxy-5-methylhexane hydrochloride (derived from 98 mg, 0.28 mmol, of 3-t-butyloxycarbonylamino-1-cyclohexylmercapto-2-hydroxy-5-methylhexane using the procedure of Example 19d) in dry dimethylformamide (2 ml) containing N-methylmorpholine (29 mg, 0.28 mmol). Hydroxybenzotriazole (HOBT, 58 mg, 0.43 mmol) and N,N'-dicyclohexylcarbodiimide (DCC, 59 mg, 0.28 mmol) were then added sequentially. After 2 hours the mixture was allowed to warm to room temperature. After 22 hours the mixture was filtered, evaporated, and partitioned between ethyl acetate (18 ml) and saturated $NaHCO_3$ (6 ml). The layers were separated, and the organic phase was washed with brine (5 ml), dried ($Na_2SO_4$), filtered, and evaporated to a solid which was chromatographed on $SiO_2$ (9/1, dichloromethane/methanol) to give 86 mg (63%) of the desired compound. Mass spectrum: $(M+H)^+ = 483$.

f. 2-t-Butyloxycarbonylamino-1-cyclohexylbut-3-ene

Using the procedure of Example 19a, but replacing Boc-leucinal with Boc-cyclohexylalaninal, gave the desired compound. Mass spectrum: $(M+H)^+ = 254$.

g. 3 t-Butyloxycarbonylamino-4-cyclohexyl-1,2-oxobutane

Using the procedure of Example 19b with the resultant compound of Example 19f, gave the desired compound. Mass spectrum: $(M+H)^+ = 270$.

h. 3-t-Butyloxycarbonylamino-4-cyclohexyl-1-cyclohexylmercapto-2-hydroxybutane Using the procedure of Example 19c with the resultant compound of Example 19g, gave the desired compound. Mass spectrum: $M^+ = 385$.

i. 3-Amino-4-cyclohexyl-1-cyclohexylmercapto-2-hydroxybutane hydrochloride

Using the procedure of Example 19d with the resultant compound of Example 19h, gave the desired compound.

j. Boc-Phe-His Amide of 3-Amino-4-cyclohexyl-1-cyclohexylmercapto-2-hydroxybutane Using the procedure of Example 19e (replacing Boc-His-OH with Boc-Phe-His-OH) employing the resultant compound of Example 19i, gave the desired compound.

effect of Renin Inhibiting Compounds on Rabbit Plasma Renin a. Method The effect of the compounds on renin was assessed in a rabbit plasma system at pH 7.4. The amount of angiotensin I produced by incubating the plasma for 2 h at 37° was measured in the absence of and in the presence of 3 concentrations of test compound. The concentration causing 50% inhibition of the formation of angiotensin I, the $IC_{50}$, was calculated from a semi log plot of the concentration versus the percent inhibition.

b. Results Inhibition of Rabbit Plasma Renin at pH 7.4

| Compound | $IC_{50}$, M × $10^{-6}$ |
|---|---|
| I | 0.062 |
| II | 0.062 |
| III | 0.016 |
| IV | 0.14 |

The results obtained show that the compounds are potent inhibitors of rabbit renin in the micromolar and submicromolar concentration range.

Effects of Topically Administered Renin Inhibiting Compounds on Intraocular Pressure of Rabbits a. Method The antiglaucoma activity of the compounds was tested by measuring the effect on intraocular pressure in rabbits as described by Tinjum, A. M., Acta Ophthalmologica, 50, 677 (1972). Male albino, New Zealand rabbits were placed in restraining devices and the intraocular pressure was measured with an applamatic tonometer. Exactly 0.1 ml of an isotonic saline solution containing a test compound was instilled into the conjuctival sac and the intraocular pressure was measured at 5, 15, 30, 60, 90, 120 and 180 minutes afterwards. The results obtained show that the compounds of the invention are able to reduce intraocular pressure in vivo.

| Treatment[a] | Mean Intraocular Pressure in mmHg Minutes after Administration | | | | | | | |
|---|---|---|---|---|---|---|---|---|
|  | 0 | 5 | 15 | 30 | 60 | 90 | 120 | 180 |
| Vehicle | 18.9 | — | 18.8 | 17.6 | 19.1 | 20.4 | 22.3 | — |
| Pilocarpine | 17.6 | 14.4 | 13.0 | 11.9 | 13.0 | 12.6 | 16.4 | 17.7 |
| Timolol | 16.2 | 12.1 | 9.9 | 11.9 | 10.6 | 12.4 | 13.3 | 14.5 |
| Compound I | 19.0 | 18.2 | 16.5 | 12.2 | 13.9 | 15.1 | 16.8 | 20.4 |
| Compound II | 18.4 | 15.0 | 13.5 | 13.2 | 13.4 | 17.1 | 19.0 | 17.2 |
| Compound III | 19.1 | 15.5 | 12.4 | 13.9 | 14.9 | 16.3 | 17.8 | 18.2 |
| Compound IV | 18.2 | 14.5 | 13.0 | 13.3 | 14.2 | 16.3 | 14.9 | 16.2 |
| Compound XIII | 19.5 | 17.6 | 17.2 | 15.6 | 16.4 | 16.3 | 17.5 | 15.3 |
| Compound XIV | 21.0 | 16.8 | 14.0 | 15.1 | 14.6 | 16.4 | 17.9 | 19.6 |
| Vehicle | 20.1 | 21.4 | 19.6 | 19.5 | 17.8 | 20.0 | 21.6 | 21.3 |
| Compound VI | 21.0 | 16.5 | 16.5 | 15.2 | 14.7 | 21.7 | 22.4 | 19.9 |
| Compound VII | 19.7 | 17.2 | 13.8 | 14.3 | 14.8 | 19.3 | 21.1 | 22.7 |
| Compound VIII | 19.4 | 17.0 | 16.5 | 15.4 | 18.4 | 21.2 | 20.5 | 21.9 |
| Compound IX | 22.2 | 22.5 | 18.1 | 15.8 | 19.5 | 22.4 | 24.3 | 24.2 |
| Compound X | 20.8 | 20.6 | 20.6 | 15.9 | 15.1 | 19.1 | 20.6 | 21.7 |
| Vehicle | 19.6 | 19.9 | 18.7 | 19.5 | 19.2 | 19.1 | 19.7 | 18.8 |
| Compound XI | 18.5 | 13.4 | 11.4 | 10.6 | 14.6 | 16.1 | 15.7 | 19.0 |
| Compound XII | 19.3 | 12.5 | 10.3 | 12.4 | 12.3 | 12.3 | 14.6 | 16.3 |

[a]All solutions contain 0.1% (w/v) compound except Timolol which contains 0.5% active substance.

Each value cited represents the average of 6 observations. All of the test compounds, including the standard references pilocarpine and timolol, caused maximum drops in intraocular pressure ranging from 4.2 to 7.0 mmHg, while the vehicle control caused only small, variable changes, the largest of which were increases in pressure 90 and 120 minutes after installation.

Dose Response Study of the Effects of Topically Administered Renin Inhibiting Compounds on Intraocular Pressure of Rabbits a. Method Using the method cited above, various topically administered doses of Compound V and timolol were studied.

b. Results

| Treatment | Mean Intraocular Pressure in mmHg Minutes after Administration | | | | | | | |
|---|---|---|---|---|---|---|---|---|
|  | CONTROL | 5 | 15 | 30 | 60 | 90 | 120 | 150 |
| Vehicle | 20.1 | 19.1 | 21.5 | 19.2 | 20.7 | 20.7 | 18.8 | 21.3 |
| Compound V 0.01% | 19.2 | 17.7 | 16.3 | 13.7 | 16.9 | 15.4 | 18.2 | 20.3 |
| Compound V 0.03% | 19.0 | 13.8 | 13.3 | 12.8 | 13.8 | 13.8 | 15.2 | 16.8 |
| Compound V 0.1% | 18.7 | 14.1 | 13.1 | 11.9 | 11.3 | 11.5 | 17.5 | 19.0 |
| Compound V 0.3% | 21.2 | 13.3 | 12.0 | 10.9 | 12.2 | 12.4 | 16.0 | 18.8 |
| Timolol 0.02% | 19.1 | 16.5 | 16.6 | 13.9 | 19.1 | 18.9 | 22.4 | 19.9 |
| Timolol 0.05% | 18.2 | 15.4 | 12.8 | 12.8 | 12.3 | 15.6 | 17.8 | 20.3 |
| Timolol 0.2% | 18.6 | 12.1 | 12.5 | 14.7 | 12.8 | 15.6 | 15.9 | 18.9 |
| Timolol 0.5% | 18.4 | 12.8 | 12.8 | 11.0 | 10.9 | 16.1 | 17.2 | 18.7 |

Each value cited represents the average of 6 observations. The contralateral eye in each rabbit was untreated. The results indicate that the intraocular pressure lowering effect of Compound V lasts 30 to 60 minutes longer than timolol at a dose one half that of timolol.

Effect of Topically Administered Compound V Alone and In Combination With Timolol On Intraocular Pressure of Rabbits a. Method Using the method cited above, topically administered doses of Compound V and timolol, alone and in combination, were studied.

b. Results

| Treatment | Mean Intraocular Pressure in mmHg Minutes after Administration | | | | | | | |
|---|---|---|---|---|---|---|---|---|
|  | CONTROL | 5 | 15 | 30 | 60 | 90 | 120 | 150 |
| Vehicle | 20.1 | 19.1 | 21.5 | 19.2 | 20.7 | 20.7 | 18.8 | 21.3 |
| Compound V 0.03% | 17.5 | 10.4 | 10.3 | 10.1 | 10.2 | 10.4 | 14.5 | 17.0 |

| Treatment | Mean Intraocular Pressure in mmHg Minutes after Administration | | | | | | | |
|---|---|---|---|---|---|---|---|---|
| | CONTROL | 5 | 15 | 30 | 60 | 90 | 120 | 150 |
| Timolol 0.05% | 16.8 | 10.2 | 11.0 | 10.1 | 9.9 | 13.9 | 14.5 | 17.0 |
| Compound V 0.03% and Timolol 0.05% | 18.5 | 10.9 | 10.5 | 9.5 | 11.6 | 14.0 | 14.7 | 15.3 |

Each value cited represents the average of 6 observations. The contralateral eye in each rabbit was untreated. The results indicate that the intraocular pressure lowering effect of a combination of Compound V and timolol has a longer duration of action than either compound when administered alone.

The foregoing is merely illustrative of the invention and is not intended to limit the invention to the disclosed methods and compositions. Variations and changes which are obvious to one skilled in the art are intended to be within the scope and nature of the invention which are defined in the appended claims.

What is claimed is:

1. A method for treating glaucoma or reducing and/or controlling intraocular pressure comprising administering to a patient in need a therapeutically effective amount of a renin inhibiting compound of the formula:

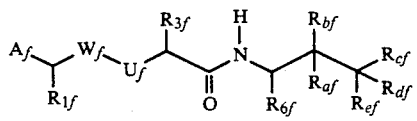

wherein $A_f$ is hydrogen, loweralkyl, arylalkyl, $-OR_{10f}$ or $-SR_{10f}$ wherein $R_{10f}$ is hydrogen, loweralkyl or aminoalkyl, $-NR_{11f}R_{12f}$ wherein $R_{11f}$ and $R_{12f}$ are independently selected from hydrogen, loweralkyl, aminoalkyl, cyanoalkyl, hydroxyalkyl, carboxyalkyl, alkoxycarbonylalkyl, (amino)carboxyalkyl, ((N-protected)amino)carboxyalkyl, (alkylamino)carboxyalkyl, ((N-protected)alkylamino)carboxyalkyl, (dialkylamino)carboxyalkyl, (amino)alkoxycarbonylalkyl, ((N-protected)amino)alkoxycarbonylalkyl, (alkyamino)alkoxycarbonylalkyl, ((N-protected)alkylamino)alkoxycarbonylalkyl and (dialkylamino)alkoxycarbonylalkyl; or $A_f$ is

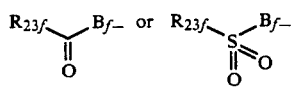

wherein $B_f$ is NH, alkylamino, S, O, $CH_2$ or CHOH and $R_{23f}$ is loweralkyl, cycloalkyl, aryl, arylalkyl, alkoxy, alkenyloxy, hydroxyalkoxy, dihydroxyalkoxy, arylalkoxy, arylalkoxyalkyl, amino, alkylamino, dialkylamino, (hydroxyalkyl)(alkyl)amino, (dihydroxyalkyl)(alkyl)amino, aminoalkyl, N-protected-aminoalkyl, alkylaminoalkyl, (N-protected)(alkyl)aminoalkyl, dialkylaminoalkyl, carboxyalkoxyalkyl, (alkoxycarbonyl)alkoxyalkyl, carboxyalkyl, carboxyalkylamino, alkoxycarbonylalkyl, alkoxycarbonylalkylamino, (amino)carboxyalkyl, (amino)carboxyalkylamino, ((N-protected)amino)carboxyalkyl, ((N-protected)amino)-carboxyalkyamino, (alkylamino)carboxyalkyl, (alkylamino)carboxyalkylamino, ((N-protected)alkylamino)-carboxyalkyl, ((N-protected)alkylamino)carboxyalkylamino, (dialkylamino)carboxyalkyl, (dialkylamino)carboxyalkylamino, (amino)alkoxycarbonylalkyl, (amino)alkoxycarbonylalkylamino, ((N-protected)amino)alkoxycarbonylalkyl, ((N-protected)amino)- alkoxycarbonylalkylamino, (alkylamino)alkoxycarbonylalkyl, (alkylamino)alkoxycarbonylalkylamino, ((N-protected)alkylamino)alkoxycarbonylalkyl, ((N-protected)alkylamino)alkoxycarbonylalkylamino, (dialkylamino)alkoxycarbonylalkyl, (dialkylamino)alkoxycarbonylalkylamino, aminocycloalkyl, aminoalkylamino, dialkylaminoalkyl(alkyl)amino, arylalkylamino, arylalkyl(alkyl)amino, alkoxyalkyl(alkyl)amino, (polyalkyoxy)alkyl(alkyl)amino, di-(alkoxyalkyl)amino, di-(hydroxyalkyl)amino, di-((polyalkoxy)alkyl)amino, polyalkoxy, (polyalkoxy)alkyl, (heterocyclic)alkyl or a substituted or unsubstituted heterocyclic wherein saturated heterocyclics may be unsubstituted, monosubstituted or disubstituted with hydroxy, oxo, amino, alkylamino, dialkylamino, alkoxy, polyalkoxy or loweralkyl; unsaturated heterocyclics may be unsubstituted or monosubstituted with hydroxy, amino, alkylamino, dialkylamino, alkoxy, polyalkoxy or loweralkyl;

$W_f$ is C=O or CHOH;

$U_f$ is $CH_2$ or $NR_{2f}$; provided that when $W_f$ is CHOH then $U_f$ is $CH_2$;

$R_{1f}$ is loweralkyl, cycloalkylmethyl, benzyl, 4-methoxybenzyl, halobenzyl, (1-naphthyl)methyl, (2-naphthyl)methyl, (4-imidazolyl)methyl, (alpha,alpha)-dimethylbenzyl, 1-benzyloxyethyl, phenethyl, phenoxy, thiophenoxy or anilino; provided that when $R_{1f}$ is phenoxy, thiophenoxy or anilino, then $B_f$ is $CH_2$ or CHOH or $A_f$ is hydrogen;

$R_{2f}$ is hydrogen or loweralkyl;

$R_{3f}$ is loweralkyl, loweralkenyl, ((alkoxy)alkoxy)loweralkyl, (thioalkoxy)alkyl, benzyl or heterocyclic ring substituted methyl;

$R_{6f}$ is loweralkyl, cycloalkylmethyl or benzyl;

$R_{af}$ is vinyl, formyl, hydroxymethyl or hydrogen;

$R_{df}$ is hydrogen or loweralkyl;

$R_{bf}$ and $R_{ef}$ are independently selected from OH and $NH_2$; and $R_{cf}$ is hydrogen, loweralkyl, vinyl or arylalkyl; or a pharmaceutically acceptable salt or ester thereof, in combination with a therapeutically effective amount of a beta-adrenergic antagonist compound.

2. The method of claim 1 wherein the beta-adrenergic antagonist compound comprises timolol.

3. The method of claim 1 wherein the beta-adrenergic antagonist compound and renin inhibiting compound are administered as separate compositions or the beta-adrenergic antagonist compound and the renin inhibiting compound are administered as components of the same composition.

4. The method of claim 1 wherein the renin inhibiting compound is H-((beta,beta-dimethyl)-beta-Ala)-(4-OCH₃)Phe-His amide of 2(S)-amino-1-cyclohexyl-3(R),4(S)-dihydroxy-6-methylheptane.

5. A composition for treating glaucoma or reducing and/or controlling intraocular pressure comprising a pharmaceutical vehicle suitable for topical ocular administration and a therapeutically effective amount of a renin inhibiting compound of the formula:

$$A_f \underset{R_{1f}}{\overset{R_{3f}}{\bigvee}} W_f - U_f \underset{O}{\overset{H}{\bigvee}} \underset{R_{6f}}{\overset{R_{bf}}{\bigvee}} \underset{R_{ef}}{\overset{R_{cf}}{\bigvee}} R_{df}$$

wherein $A_f$ is hydrogen, loweralkyl, arylalkyl, $-OR_{10f}$ or $-SR_{10f}$ wherein $R_{10f}$ is hydrogen, loweralkyl or aminoalkyl, $-NR_{11f}R_{12f}$ wherein $R_{11f}$ and $R_{12f}$ are independently selected from hydrogen, loweralkyl, aminoalkyl, cyanoalkyl, hydroxyalkyl, carboxyalkyl, alkoxycarbonylalkyl, (amino)carboxyalkyl, ((N-protected)amino)carboxyalkyl, (alkylamino)carboxyalkyl, ((N-protected)alkylamino)carboxyalkyl, (dialkylamino)carboxyalkyl, (amino)alkoxycarbonylalkyl, ((N-protected)amino)alkoxycarbonylalkyl, (alkyamino)alkoxycarbonylalkyl, ((N-protected alkylamino)alkoxycarbonylalkyl and (dialkylamino)alkoxycarbonylalkyl; or $A_f$ is $$R_{23f}\underset{O}{\overset{}{\bigvee}}B_f- \text{ or } R_{23f}\underset{O}{\overset{S}{\bigvee}}B_f-$$
$$\qquad\qquad\qquad\qquad O$$

wherein $B_f$ is NH, alkylamino, S, O, CH$_2$ or CHOH and $R_{23f}$ is loweralkyl, cycloalkyl, aryl, arylalkyl, alkoxy, alkenyloxy, hydroxyalkoxy, dihydroxyalkoxy, arylalkoxy, arylalkoxyalkyl, amino, alkylamino, dialkylamino, (hydroxyalkyl)(alkyl)amino, (dihydroxyalkyl)(alkyl)amino, aminoalkyl, N-protected-aminoalkyl, alkylaminoalkyl, (N-protected)(alkyl)aminoalkyl, dialkylaminoalkyl, carboxyalkoxyalkyl, (alkoxycarbonyl)alkoxyalkyl, carboxyalkyl, carboxyalkylamino, alkoxycarbonylalkyl, alkoxycarbonylalkylamino, (amino)carboxyalkyl, (amino)carboxyalkylamino, ((N-protected)amino)carboxyalkyl, ((N-protected)amino)carboxyalkyamino, (alkylamino)carboxyalkylo, (alkylamino)carboxyalkylamino, ((N-protected)alkylamino)carboxyalkyl, ((N-protected)alkylamino)carboxyalkylamino, (dialkylamino)carboxyalkyl, (dialkylamino)carboxyalkylamino, (amino)alkoxycarbonylalkyl, (amino)alkoxycarbonylalkylamino, ((N-protected)amino)alkoxycarbonylalkyl, ((N-protected)amino)- alkoxycarbonylalkylamino, (alkylamino)alkoxycarbonylalkyl, (alkylamino)alkoxycarbonylalkylamino, ((N-protected)alkylamino)- alkoxycarbonylalkyl, ((N-protected)alkylamino)alkoxycarbonyl- alkylamino, (dialkylamino)alkoxycarbonylalkyl, (dialkylamino)alkoxycarbonylalkylamino, aminocycloalkyl, aminoalkylamino, dialkylaminoalkyl(alkyl)amino, arylalkylamino, arylalkyl(alkyl)amino, alkoxyalkyl(alkyl)amino, (polyalkyoxy)-alkyl(alkyl)amino, di-(alkoxyalkyl)amino, di-(hydroxyalkyl)amino, di-((polyalkoxy)alkyl)amino, polyalkoxy, (polyalkoxy)alkyl, (heterocyclic)alkyl or a substituted or unsubstituted heterocyclic wherein saturated heterocyclics may be unsubstituted, monosubstituted or disubstituted with hydroxy, oxo, amino, alkylamino, dialkylamino, alkoxy, polyalkoxy or loweralkyl; unsaturated heterocyclics may be unsubstituted or monosubstituted with hydroxy, amino, alkylamino, dialkylamino, alkoxy, polyalkoxy or loweralkyl;

$W_f$ is C=O or CHOH;

$U_f$ is CH$_2$ or NR$_2$, provided that when $W_f$ is CHOH then $U_f$ is CH$_2$;

$R_{1f}$ is loweralkyl, cycloalkylmethyl, benzyl, 4-methoxybenzyl, halobenzyl, (1-naphthyl)methyl, (2-naphthyl)methyl, (4-imidazolyl)methyl, (alpha,alpha)-dimethylbenzyl, 1-benzyloxyethyl, phenethyl, phenoxy, thiophenoxy or anilino; provided that when $R_{1f}$ is phenoxy, thiophenoxy or anilino, then $B_f$ is CH$_2$ or CHOH or $A_f$ is hydrogen;

$R_{2f}$ is hydrogen or loweralkyl;

$R_{3f}$ is loweralkyl, loweralkenyl, ((alkoxy)alkoxy)loweralkyl, (thioalkoxy)alkyl, benzyl or heterocyclic ring substituted methyl;

$R_{6f}$ is loweralkyl, cycloalkylmethyl or benzyl;

$R_{af}$ is vinyl, formyl, hydroxymethyl or hydrogen;

$R_{df}$ is hydrogen or loweralkyl;

$R_{bf}$ and $R_{ef}$ are independently selected from OH and NH$_2$; and $R_{cf}$ is hydrogen, loweralkyl, vinyl or arylalkyl; or a pharmaceutically acceptable salt or ester thereof, in combination with a therapeutically effective amount of a beta-adrenergic antagonist compound.

6. The composition of claim 5 wherein the beta-adrenergic antagonist compound is timolol.

7. The composition of claim 5 wherein the renin inhibiting compound is H-((beta,beta-dimethyl)-beta-Ala)-(4-OCH$_3$)Phe-His amide of 2(S)-amino-1-cyclohexyl-3(R),4(S)-dihydroxy-6-methylheptane.

* * * * *

UNITED STATES PATENT AND TRADEMARK OFFICE
CERTIFICATE OF CORRECTION

PATENT NO. : 5,036,051

DATED : July 30, 1991

INVENTOR(S) : Herman H. Stein; Jacob J. Plattner

It is certified that error appears in the above-identified patent and that said Letters Patent is hereby corrected as shown below:

On Title Page, in Abstract, Column 2, Line 21, Replace "Ch2" with --$CH_2$--.

Column 60, line 17, replace "NR2" with --$NR_{2f}$--.

Signed and Sealed this

Sixteenth Day of March, 1993

Attest:

STEPHEN G. KUNIN

*Attesting Officer*     *Acting Commissioner of Patents and Trademarks*